US010154966B2

(12) United States Patent
Barnscheid et al.

(10) Patent No.: US 10,154,966 B2
(45) Date of Patent: Dec. 18, 2018

(54) TAMPER-RESISTANT DOSAGE FORM CONTAINING ONE OR MORE PARTICLES

(71) Applicant: GRÜNENTHAL GMBH, Aachen (DE)

(72) Inventors: Lutz Barnscheid, Mönchengladbach (DE); Anja Geißler, Stolberg (DE); Klaus Wening, Köln (DE); Jana Pätz, Bornheim (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/287,512

(22) Filed: May 27, 2014

(65) Prior Publication Data
US 2014/0356426 A1 Dec. 4, 2014

(30) Foreign Application Priority Data

May 29, 2013 (EP) .................................. 13169658
Mar. 20, 2014 (EP) .................................. 14160958

(51) Int. Cl.
| A61K 9/48 | (2006.01) |
| A61K 9/14 | (2006.01) |
| A61K 9/28 | (2006.01) |
| A61K 31/485 | (2006.01) |
| A61K 45/06 | (2006.01) |
| A61K 9/20 | (2006.01) |

(52) U.S. Cl.
CPC .............. *A61K 9/4891* (2013.01); *A61K 9/14* (2013.01); *A61K 9/146* (2013.01); *A61K 9/2081* (2013.01); *A61K 9/28* (2013.01); *A61K 31/485* (2013.01); *A61K 45/06* (2013.01)

(58) Field of Classification Search
CPC ... A61K 9/14; A61K 9/16; A61K 9/50; A61K 9/51
See application file for complete search history.

(56) References Cited

U.S. PATENT DOCUMENTS

| 3,332,950 | A | 7/1967 | Blumberg et al. |
| 3,370,035 | A | 2/1968 | Ogura et al. |
| 3,652,589 | A | 3/1972 | Flick et al. |
| 3,806,603 | A | 4/1974 | Gaunt et al. |
| 3,865,108 | A | 2/1975 | Hartop |
| 3,941,865 | A | 3/1976 | Miller et al. |
| 3,966,747 | A | 6/1976 | Monkovic et al. |
| 3,980,766 | A | 9/1976 | Shaw et al. |
| 4,002,173 | A | 1/1977 | Manning et al. |
| 4,014,965 | A | 3/1977 | Stube et al. |
| 4,070,494 | A | 1/1978 | Hoffmeister et al. |
| 4,070,497 | A | 1/1978 | Wismer et al. |
| 4,175,119 | A | 11/1979 | Porter |
| 4,200,704 | A | 4/1980 | Stanley et al. |
| 4,207,893 | A | 6/1980 | Michaels |
| 4,262,017 | A | 4/1981 | Kuipers et al. |
| 4,343,789 | A | 8/1982 | Kawata et al. |
| 4,353,887 | A | 10/1982 | Hess et al. |
| 4,404,183 | A | 9/1983 | Kawata et al. |
| 4,427,681 | A | 1/1984 | Munshi et al. |
| 4,427,778 | A | 1/1984 | Zabriskie |
| 4,457,933 | A | 7/1984 | Gordon et al. |
| 4,462,941 | A | 7/1984 | Lee et al. |
| 4,473,640 | A | 9/1984 | Combie et al. |
| 4,483,847 | A | 11/1984 | Augart |
| 4,485,211 | A | 11/1984 | Okamoto |
| 4,529,583 | A | 7/1985 | Porter |
| 4,599,342 | A | 7/1986 | La Hann |
| 4,603,143 | A | 7/1986 | Schmidt |
| 4,612,008 | A | 9/1986 | Wong et al. |
| 4,629,621 | A | 12/1986 | Snipes |
| 4,667,013 | A | 5/1987 | Reichle |
| 4,690,822 | A | 9/1987 | Uemura |
| 4,713,243 | A | 12/1987 | Schiraldi et al. |
| 4,744,976 | A | 5/1988 | Snipes et al. |
| 4,764,378 | A | 8/1988 | Keitn et al. |
| 4,765,989 | A | 8/1988 | Wong et al. |
| 4,774,074 | A | 9/1988 | Snipes |
| 4,774,092 | A | 9/1988 | Hamilton |
| 4,783,337 | A | 11/1988 | Wong et al. |
| 4,806,337 | A | 2/1989 | Snipes et al. |
| RE33,093 | E | 10/1989 | Schiraldi et al. |
| 4,880,585 | A | 11/1989 | Klimesch et al. |
| 4,892,778 | A | 1/1990 | Theeuwes et al. |
| 4,892,889 | A | 1/1990 | Kirk |
| 4,940,556 | A | 7/1990 | MacFarlane et al. |
| 4,954,346 | A | 9/1990 | Sparta et al. |
| 4,957,668 | A | 9/1990 | Plackard et al. |
| 4,957,681 | A | 9/1990 | Klimesch et al. |
| 4,960,814 | A | 10/1990 | Wu et al. |
| 4,992,278 | A | 2/1991 | Khanna |
| 4,992,279 | A | 2/1991 | Palmer et al. |
| 5,004,601 | A | 4/1991 | Snipes |
| 5,051,261 | A | 9/1991 | McGinty |
| 5,073,379 | A | 12/1991 | Klimesch et al. |
| 5,082,668 | A | 1/1992 | Wong et al. |
| 5,126,151 | A | 6/1992 | Bodor et al. |
| 5,139,790 | A | 8/1992 | Snipes |
| 5,145,944 | A | 9/1992 | Steinmann |
| 5,149,538 | A | 9/1992 | Granger et al. |

(Continued)

FOREIGN PATENT DOCUMENTS

| AR | 046994 A1 | 12/2004 |
| AR | 045353 A1 | 10/2005 |

(Continued)

OTHER PUBLICATIONS

R Moorman-Li, CA Motycka, LD Inge, JM Congdon, S Hobson, B Pokropski. "A Review of Abuse-Deterrent Opioids for Chronic Nonmalignant Pain." Pharmacy and Therapeutics, vol. 37 No. 7, Jul. 2012, pp. 412-421.*

(Continued)

*Primary Examiner* — Isaac Shomer
(74) *Attorney, Agent, or Firm* — Norris McLaughlin, P.A.

(57) ABSTRACT

The invention relates to a tamper-resistant pharmaceutical dosage form comprising one or more particles, wherein each of said one or more particles
  comprises a pharmacologically active ingredient and a physiologically acceptable polymer;
  has a breaking strength of at least 300 N;
  has a weight of at least 2 mg; and
  optionally, comprises a film-coating;
wherein the total weight of the pharmaceutical dosage form is greater than the total weight of said one or more particles.

22 Claims, 20 Drawing Sheets

(56) References Cited

U.S. PATENT DOCUMENTS

| | | |
|---|---|---|
| 5,169,645 A | 12/1992 | Shukla et al. |
| 5,227,157 A | 1/1993 | McGinity et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,989,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |

(56) References Cited

U.S. PATENT DOCUMENTS

| | | |
|---|---|---|
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Joshi et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iver et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1* | 7/2003 | Oshlack et al. ............... 424/468 |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Aver et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1* | 8/2005 | Oshlack et al. ............... 424/468 |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1* | 1/2009 | Arkenau-Maric et al. ... 424/465 |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1* | 8/2009 | Jans .................. A61K 9/2018 424/468 |
| 2009/0215808 A1 | 8/2009 | Yum et al. |
| 2009/0232887 A1* | 9/2009 | Odidi et al. ................ 424/457 |

(56) References Cited

U.S. PATENT DOCUMENTS

| | | |
|---|---|---|
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1* | 1/2013 | Schwier ............... A61K 9/2081 424/464 |
| 2013/0028972 A1* | 1/2013 | Schwier ............... A61K 9/2077 424/465 |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2006311116 B2 | 1/2013 |
| BR | P10413318 A | 10/2006 |
| BR | P10413361 A | 10/2006 |
| BR | P10513300 A | 5/2008 |
| BR | P10606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 | 1/2002 |
| CA | 2456322 A1 | 2/2003 |
| CA | 2502965 A1 | 5/2004 |
| CA | 2503155 | 5/2004 |
| CA | 2534925 A1 | 2/2005 |
| CA | 2534932 A1 | 2/2005 |
| CA | 2489855 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |

(56) References Cited

FOREIGN PATENT DOCUMENTS

| | | |
|---|---|---|
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 1/2010 |
| CN | 101652128 A | 2/2010 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0780369 A1 | 6/1997 |
| EP | 0785775 A1 | 7/1997 |
| EP | 0761211 A1 | 12/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |

(56) References Cited

FOREIGN PATENT DOCUMENTS

| | | |
|---|---|---|
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2010534204 A | 11/2010 |
| JP | 2011504455 A | 2/2011 |
| JP | 2011506493 A | 3/2011 |
| JP | 2012515735 A | 7/2012 |
| JP | 2012528845 A | 11/2012 |
| JP | 2013536810 A | 9/2013 |
| JP | 2014505736 A | 3/2014 |
| JP | 2014528437 A | 10/2014 |
| JP | 6085307 B2 | 2/2017 |
| JP | 2013523780 A | 6/2017 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | I254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/014058 A1 | 1/1996 |
| WO | WO 1996/003979 A1 | 2/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |

(56) References Cited

FOREIGN PATENT DOCUMENTS

| | | |
|---|---|---|
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/0128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2008/109462 A2 | 4/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/0088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/0149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 | 7/2015 |

OTHER PUBLICATIONS 2.9 Methoden der pharmazeutischen Technologie, European Pharmacopeia, 143-144, 1997. (Full English translation attached).

Albertini, B. "New spray congealing atomizer for the microencapsulation of highly concentrated solid and liquid substances" European Journal of Pharmaceutics and Biopharmaceutics 69 (2008) 348-357.

Almeida, A. et al., Ethylene vinyl acetate as matrix for oral sustained release dosage forms produced via hot-melt extrusion, European Journal of Pharmaceutics and Biopharmaceutics 77 (2011) 297-305.

Almeida, A. et al., Sustained release from hot-melt extruded matrices based on ethylene vinyl acetate and polyethylene oxide, European Journal of Pharmaceutics and Biopharmaceutics 82 (2012) 526-533.

Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.

(56) References Cited

OTHER PUBLICATIONS

Apicella A.et al., Biomaterials, vol. 14, No. 2, pp. 83-90,1993.
Application of a modelling system in the formulation of extended release hydrophilic matrices, Reprinted from Pharmaceutical Technology Europe, Jul. 2006.
Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones, III The Effect of Quantity and Type of Catalysts, J.Org Chem. 28(1), pp. 152-155, Abstract 1963.
Avis, Kenneth, Parenteral Preparations. Chapter 85, pp. 1518-1541In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents, (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence, 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc, CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-metl extrusion," Biomaterials 23, 2002, pp. 4241-4248.
Crowley MM, Drug Dev Ind Pharm, Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Disanto, Anthony, Bioavailability and Bioequivalency Testing, Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 Table of Content only).
Erskine, Jr., Clyde. Quality Assurance and Control, Chapter 83. pp. 1487-1491 In Remington's Pharmaceutical Sciences, 17th Ed, 1985.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Written Opinion for EP Application No. 11006253.6-2112, dated Dec. 16, 2011.
European Search Report and Written Opinion for EP Application No. 11006254.4-2112, dated Dec. 16, 2011.
European Search Report and Written Opinion for EP Application No. 12002708.1-1219, dated Sep. 24, 2012.
European Search Report and Written Opinion for EP Application No. 11008131.2-1219, dated Feb. 24, 2012.
European Search Report and Written Opinion for EP Application No. 11009129.5-2112, dated Apr. 10, 2012.
European Search Report and Written Opinion for EP Application No. 12001296.8-1219, dated Jun. 26, 2012.

(56) References Cited

OTHER PUBLICATIONS

European Search Report and Written Opinion for EP Application No. 12001301.6-1219, dated Jun. 26, 2012.
European Search Report and Written Opinion for EP Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry: Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81, pp. 1473-1477 in Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces. Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).

Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCI 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Lee, Y.-S. et al., Principles of Terahertz Science and Technology (Lecture Notes in Physics), Springer; 1 edition 2008. (Table of Contents Only).
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).

(56) References Cited

OTHER PUBLICATIONS

Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 750 mg Extended Release Tablets, Lubrizol Advanced Materials, Inc., Sep. 2010.
Metformin Hydrochloride1000 mg Extended Release Tablets, Lubrizol Advanced Materials, Inc., Nov. 20, 2009, Previous Edition Dec. 19, 2008.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises àjour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta^9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives, Chapter 84. pp. 1492-1517, in Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., The effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)"Journal of Controlled Release 58, pp. 87-95, 1999.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Oct. 1991, 8(10), S-192.
Pharm. Research, Official Journal of the American Association of Pharmaceutical Scientists, Sep. 1989, 6(9), S-98.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system, Journal of Controlled Release. 2000, vol. 67, pp. 67-78.
Pinto, Joao F. et al., "Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals. Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (DOW Mar. 2002); see http://msdssearch.dow.com/PublishedLiteratureDOWCOM/dh_0031/0901b80380031a4a.pdf?filepath=/320-00001.pdf&fromPage=GetDoc).
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.

(56) References Cited

OTHER PUBLICATIONS

Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung, 2nd Edition, 2002, Ch 6, pp. 515-519. (Full English translation attached).
Ritschel et al. Die Tablette: Handbuch der Entwicklung, Herstellung und Qualitatssicherung, 2nd Edition, 2002, Ch 6, pp. 69-82 and 115-136.
Ritschel et al. Die Tablette: Handbuch der Entwicklung, Herstellung und Qualitatssicherung, 2nd Edition, 2002, Table of content.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al, "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P. et al., "Factors Affecting Release of KCl From Melt extruded Polyethylene Disks", Pharmaceutical Research, Oct. 1991, vol. 8, No. 10, p. S-192.

Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., Überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition. vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition. vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).

(56) References Cited

OTHER PUBLICATIONS

Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart—N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart—N.Y., 1982, Table of Content.
Waltimo, et al, "A novel bite force recorder and maximal isometric bite force values for healthy young adults", Scandinavian Journal of Dental Research 1993; 101:171-175.
Waltimo, et al, "Maximal bite force and its association with signs and symptoms of craniomandibular disorders in young Finnish non-patients", ACTA Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892. Nov. 20, 1955.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).

Zhang et al., "Properties of Sustained-Release Tablets Prepared by Hot-Melt Extrusion" Pharmaceutical Development and Technology, 1999, 4(2), 241-250.
Eggleston, The seat of the emetic action of various drugs: J. Pharmacol. Exp. Ther. 7, 225-253 (1915).
Evonik Rohm GmbH product brochure: EUDRAGIT acrylic polymers for solid oral dosage forms (2009).
Morissette et al. Adv. Drug. Del. Rev. 26 (2004), 275-300.
Vippagunta et al. Adv. Del. Rev. (2001), 3-26.
PCT International Search Report and Written Opinion for PCT Application No. PCT/EP2014/064830 dated Aug. 6, 2014.
Lenindzer, A., "The molecular basis of the structure and functions of cells" Moscow 1974, p. 68.
Kondrat, T., "Technology dosage forms" Moscow 1991, p. 96.
European Search Report and Written Opinion for EP Application No. 14169801.9-1455 dated Oct. 20, 2014.
European Search Report and Written Opinion for EP Application No, 14176277.3-1460, dated Dec. 15, 2014.
Dierickx et al., "Co-extrusion as manufacturing technique for fixed-dose combination mini-matrices," European Journal of Pharmaceutics and Biopharmaceutics 81 (2012), 683-689.
Oliveira et al., "Production and characterization of laminar coextrudates at room temperature in the absence of solvents," AAPS Annual Meeting and Exposition, Oct. 14-18, 2012, Chicago, USA.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Salomies et al., "Determination of Oxycodone Hydrochloride in Oral Solutions by High-Performance Thin-Layer Chromatography/Densitometry," Journal of AOAC International, 83: 1497-1501 (2000).
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Eudragit NE40D web page from Evonik website; downloaded Feb. 24, 2015.
Eudragit RS PO web page from Evonik website; downloaded Feb. 24, 2015.
Glyceryl behenate monograph; European Pharmacopeia 5.0; dated Jan. 2005; downloaded Feb. 24, 2015.
Borgquist et al., J. Controlled Release, 97: 453-465 (2004).
Bruce et al, Properties of hot-melt extuded tablet formulations for the colonic delivery of 5-aminosalicylic acid, European Journal of Pharmaceutics and Biopharmaceutics, 59 (2005) 85-97.
Bingwen et al, 2008, p. 367. (full translation attached).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Cuesov, 1999, pp. 351-352.
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455 dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.

(56) References Cited

OTHER PUBLICATIONS

Monolithic: retrieved from internet: http:/merriam-webster.com/dictionary/monolithic. Retrieved on Sep. 2, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sidhu et al., "Watch for nonpsychotropics causing psychiatric side effects," Current Psychiatry, vol. 7, No. 4, 2008, 61-74.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vynckier et al.,"Hot-melt co-extrusion for the production of fixed-dose combination products with a controlled release ethylcellulose matrix core," International Journal of Pharmaceutics 464 (2014), 65-74.
West, Anthony R., Solid state chemistry and its applications, Wiley, New York, 1988, pp. 358 and 365.
Borquist et al., "Simulation of the release from a multiparticulate system validated by single pellet and dose release experiements," J. Controlled Release, 97: 453-465 (2004).
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Efentakis et al, Effects of Excipients on Swelling and Drug Release from Compressed Matrices, in Drug Development and Industrial Pharmacy 23(1):107-112, Jan. 1997, Abstract.
Alekseeva et al, Chemical-Pharmaceutical Journal, vol. 41, No. 9, 2007, 49-52. (Full translation attached.).
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Extended European Search Report for Application No. EP 16183922.0-1460, Oct. 31, 2016.
Fathima, N. et al. "Drug-excipient interaction and its importance in dosage form development," Journal of Applied Pharmaceutical Science 01 (06); 2011, pp. 66-71.
Koziolek, M. et al., "Development of a bio-relevant dissolution test device simulating mechanical aspects present in the fed stomach," European Journal of Pharmaceutical Sciences 57 (2014) 250-256.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035. (Full Translation Attached).
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Cuesov, Drug Production Technology, Khar'kov, 1999, pp. 351-352. (Full translation attached.).
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.

Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
Cuesov, Drug Production Technology, Khar'kov, 1999, pp. 351-352.
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re Oxycontin Antitrust Litigation, *Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1):8-11.
Balogh, E., "Tastes In and Tastes Of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta, Feb. 26, 2013.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physiochemical and Mechanical Characterization of Hot-Melt Extruded Dosage Forms." Dissertation presented to the Faculty of the Graduate School of The University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.

(56) References Cited

OTHER PUBLICATIONS

Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts At Intranasal Abuse of Concerta," Letters to the Editor, J. Am. Acad. Child Adolesc. Psychiatry, 41.1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al., "Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.

Markovitz, H., et al. "Calculations of Entanglement Coupling Spacings In Linear Polymers." Journal of Physical Chemistry, 192. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharamcotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide In Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
COMPAP 90 technical data sheet Mar. 2014; 1 page.
CROWLEY0000001-CROWLEY0000127 (2015).

(56) References Cited

OTHER PUBLICATIONS

Bannwarth, Bernard, "Will Abuse-Deterrent Formulations of Opioid Analgesics be Successful in Achieving Their Purpose?", Drugs, 2012, vol. 72, pp. 1713-1723.
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
Extended European Search Report for Application No. EP 16182124.4-1455, dated Jan. 17, 2017.
Furu et al. "Use of ADHD drugs in the Nordic countries: a population-based comparison study," Acta Psychiatrica Scnadinavia, May 2010.
M. Xu et al., "Evaluation of the coat quality of sustained release pellets by individual pellet dissolution methodology," Int. J. Pharm. 478 (2015) 318-327.
PCT International Search Report and Written Opinion for PCT Application No. PCT/EP2016/052046 dated Dec. 4, 2016.
PCT International Search Report and Written Opinion for PCT Application No. PCT/EP2017/070396 dated Sep. 8, 2017.
POLYOX Water-Soluble Resins in Pharmaceutical Applications. Dow Chemicals. Published 2004.
USP Expert Council, US Pharmacopoeia, Chapter 1092, 2007, 1-15.
Nickerson, B., Sample Preparation of Pharmaceutical Dosage Forms, Springer, New York (2011); Chapter 1, pp. 3-48.
U.S. Appl. No. 60/287,509, dated Dec. 22, 2002, Joshi et al.
U.S. Appl. No. 60/288,211, dated Sep. 2, 2004, Oshlack et al.
U.S. Appl. No. 60/310,514, dated Apr. 3, 2003, Oshlack et al.
U.S. Appl. No. 60/310,534, dated Apr. 10, 2003, Wright et al.
U.S. Appl. No. 60/376,470, dated Jan. 15, 2004, Ayer et al.
U.S. Appl. No. 60/384,442, dated Dec. 4, 2003, Fink et al.
Alekseeva et al, Chemical-Pharmaceutical Journal, vol. 41, No. 9, 2007, 49-52, (English abstract included.).
Extended European Search Report and Opinion for Application No. EP 15184634.2-1455, dated Mar. 3, 2016.
Saleem et al. "Formulation and Evaluation of Tramadol hydrochloride Rectal Suppositories," Indian J. Pharm Sci. Sep.-Oct. 2008; 70(5), 640-644.
European Pharmacopoeia 3.0, 2.9.8 "Resistance to Crushing of Tablets", 1997, p. 135.
Goodman and Gilman, 1985, 7th edition, Chapter 29, 674-715.
Quadros, E. et al., "Evaluation of a novel colonic delivery device in vivo," STP Pharma Sci. 5, 77-82 (1995).
Theeuwes, Felix et al., Osmotic Systems for Colon-Targeted Drug Delivery in Colonic Drug Absorption and Metabolism (Peter R. Bieck ed., 1993).
Wooten, Marvin R. et al., Intracerebral Hemorrhage and Vasculitis Related to Ephedrine Abuse, 13 Annals of Neurology 337 (1983).
King, Remington's Pharmaceutical Sciences 17th ed., Chapter 78, p. 1418-1419 (1985).
Turkington, R., "Amphetamines," in Chemicals used for Illegal Purposes. A Guide for first Responders to Identify Explosives, Recreational Drugs, and Poisons, 2010, p. 247.
Sumitomo Seika Chemicals, Co., Ltd, "Certificate of Analysis," Product: Polyethylene Oxide; Grade: PEO-18NF; Feb. 2 2016.
Sumitomo Seika Chemicals, Co., Ltd, "Certificate of Analysis," Product: Polyethylene Oxide; Grade: PEO-20NF; Feb. 3, 2016.
Sumitomo Seika Chemicals, Co., Ltd, "Certificate of Analysis," Product: Polyethylene Oxide; Grade: PEO-20NF; Jan. 23, 2012.
Sumitomo Seika Chemicals, Co., Ltd, "Certificate of Analysis," Product: Polyethylene Oxide; Grade: PEO-20NF; May 15, 2013.
De Brabander C., et al., "Development and evaluation of sustained release mini-matrices prepared via hot melt extrusion," Journal of Controlled Release 89 (2003), 235-247.
Pharma Tips ([online] retrieved on Mar. 22, 2018 from http://www.pharmatips.in/Articles/Pharmaceutics/Tablet/Co-Processed-Directly-Compressed-Adjutants.aspx; May 2011: 10 pages).

* cited by examiner

TAMPER-RESISTANT DOSAGE FORM CONTAINING ONE OR MORE PARTICLES

This application claims priority of European Patent Application No. 13 169 658.5, filed on May 29, 2013, and of European Patent Application No. 14 160 958.6, filed on Mar. 20, 2014, the entire contents of which patent applications are hereby incorporated by reference herein.

FIELD OF THE INVENTION

The invention relates to a tamper-resistant pharmaceutical dosage form comprising one or more particles, wherein each of said one or more particles comprises a pharmacologically active ingredient and a physiologically acceptable polymer; has a breaking strength of at least 300 N; has a weight of at least 2 mg; and optionally, comprises a film-coating; wherein the total weight of the pharmaceutical dosage form is greater than the total weight of said one or more particles.

BACKGROUND OF THE INVENTION

A large number of pharmacologically active ingredients have a potential for being abused or misused, i.e. they can be used to produce effects which are not consistent with their intended use. Thus, e.g. opioids which exhibit an excellent efficacy in controlling severe to extremely severe pain, are frequently abused to induce euphoric states similar to being intoxicated. In particular, active substances which have a psychotropic effect are abused accordingly.

To enable abuse, the corresponding pharmaceutical dosage forms, such as pharmaceutical dosage forms or capsules are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered pharmaceutical dosage form is administered nasally, i.e. is sniffed.

Various concepts for the avoidance of drug abuse have been developed.

It has been proposed to incorporate in pharmaceutical dosage forms aversive agents and/or antagonists in a manner so that they only produce their aversive and/or antagonizing effects when the pharmaceutical dosage forms are tampered with. However, the presence of such aversive agents is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse, of the pharmaceutical dosage forms by the means usually available to a potential abuser is prevented or at least complicated. Such pharmaceutical dosage forms are useful for avoiding drug abuse of the pharmacologically active ingredient contained therein, as they may not be powdered by conventional means and thus, cannot be administered in powdered form, e.g. nasally. The mechanical properties, particularly the high breaking strength of these pharmaceutical dosage forms renders them tamper-resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO2009/092601.

In the course of manufacture of such tamper-resistant dosage forms having an increased breaking strength, the starting materials are typically mixed and then subjected to heat and force, i.e. thermoformed, wherein the force may be exerted prior to, simultaneously with, and/or subsequently to the application of heat. The thermoforming process, however, yields intermediates that already exhibit the desired breaking strength but need to be subsequently converted into dosage forms in an additional process step e.g. by means of conventional tabletting machines. For example, when thermoforming involves hot-melt extrusion technology, the extruded strand exiting the extruder die is cooled and cut into pieces, typically of cylindrical shape. Such intermediate cylinders, however, are not marketed as such, because they do not have the desired rounded shape. The edges of the cut surfaces may be comparatively sharp and do not comply with the general requirements concerning the outer shape of pharmaceutical dosage forms that are intended for oral administration. Shaping the intermediates into the final dosage forms that are optionally film-coated subsequently requires high pressure in order to achieve the desired form and shape. These high pressures are close to the upper pressure limit of the tabletting machines. The compression may cause fracture of the punches and may also have a negative impact on the properties of the dosage form, particularly storage stability, shelf-life and release characteristics. Further, the intermediate cylinders need to be accurately placed between the punches thus limiting the overall speed of the continuous process. Furthermore, as the intermediate cylinders are typically processed without adding exterior excipients, there are no lubricants that can provide a lubricating effect during compression and shaping by means of the tabletting machines.

Additionally, in the course of manufacture of such tamper-resistant dosage forms having an increased breaking strength, the thus obtained shaped tablets are often subsequently film-coated in an additional process step in order to color, improve appearance, increase storage stability, and the like. The coating process, however, often requires increased temperatures and when subjecting the tablets to these increased temperatures for the time that is required for coating, this may have a detrimental effect on stability of the active pharmaceutical ingredient and the excipients. Further, the coating step may undesirably entrain residual solvents into the dosage forms. Furthermore, the number of different colors that are available for coating materials is limited. It has been found that when directly applying a colored film coating on the thermoformed dosage forms, the dyes in the film coating, especially azo dyes, tend to discoloration by oxidation and other mechanisms upon storage. It appears that undesired discoloration is caused by the excipients that are usually contained in the thermoformed dosage forms in order to achieve the desired breaking strength such as polyalkylene oxides. Thus, when applying a film coating to thermoformed intermediates, either specific dyes need to be employed, e.g. dyes based on iron oxides, thereby substantially limiting the number of available colors, or a laborious protective layer is needed between the thermoformed core and the outer colored film coating in order to prevent discoloration of the dyes.

Another property of conventional tamper-resistant dosage forms is that they cannot be spontaneously chewed by a patient prior to swallowing. This is a matter of the increased breaking strength which provides tamper-resistance. However, in order to even further improve patient compliance it can be desirable to allow a certain degree of chewability without at the same time to deteriorate tamper-resistance.

In certain instances it would also be desirable to provide a series of tamper-resistant pharmaceutical dosage forms that can be easily manufactured and the composition of which can be easily varied e.g. with respect of dosage of active pharmaceutical ingredient, nature of active pharmaceutical ingredient, combinations of more than a single active pharmaceutical ingredient, release characteristics, and the like.

When conventional tamper-resistant dosage forms contain a comparatively high dose of active pharmaceutical ingredient, they tend to become comparatively large. This is because tamper-resistance often relies on the presence of polymers that are responsible for the improved mechanical strength of the dosage forms and that serve as prolonged release matrices in which the active pharmaceutical ingredient is embedded. Many patients, however, have problems in swallowing large pharmaceutically dosage forms. Thus, it would be desirable to provide tamper-resistant pharmaceutical dosage forms that can be divided into subunits which can be swallowed separately without altering drug release and without deteriorating tamper-resistance.

Besides tampering of pharmaceutical dosage forms in order to abuse the drugs contained therein, the potential impact of concomitant intake of ethanol on the in vivo release of drugs from modified release oral formulations (dose-dumping) has recently become an increasing concern. Controlled or modified release formulations typically contain a higher amount of the pharmacologically active ingredient relative to its immediate release counterpart. If the controlled release portion of the formulation is easily defeated, the end result is a potential increase in exposure to the active drug and possible safety concerns. In order to improve safety and circumvent intentional tampering (e.g. dissolving a controlled release pharmaceutical dosage form in ethanol to extract the drug), a reduction in the dissolution of the modified release fractions of such formulations, in ethanol, may be of benefit. Accordingly, the need exists to develop new formulations having reduced potential for dose dumping in alcohol.

Furthermore, the release kinetics of the pharmacologically active ingredients is an important factor. It is well known that depending on how a pharmaceutically pharmacologically active ingredient is formulated into a tablet its release pattern can be modified.

On the one hand, formulations providing immediate release upon oral administration have the advantage that they lead to a fast release of the pharmacologically active ingredient in the gastrointestinal tract. As a result, a comparatively high dose of the pharmacologically active ingredient is quickly absorbed leading to high plasma levels within a short period of time and resulting in a rapid onset of medicinal action, i.e. medicinal action begins shortly after administration. At the same time, however, a rapid reduction in the medicinal action is observed, because metabolization and/or excretion of the pharmacologically active ingredient cause a decrease of plasma levels. For that reason, formulations providing immediate release of pharmacologically active ingredients typically need to be administered frequently, e.g. six times per day. This may cause comparatively high peak plasma pharmacologically active ingredient concentrations and high fluctuations between peak and trough plasma pharmacologically active ingredient concentrations which in turn may deteriorate tolerability.

Controlled release (e.g. delayed release, prolonged release, sustained release, and the like) may be based upon various concepts such as coating the pharmaceutical dosage form with a controlled release membrane, embedding the pharmacologically active ingredient in a matrix, binding the pharmacologically active ingredient to an ion-exchange resin, forming a complex of the pharmacologically active ingredient, and the like. In this context it can be referred to, e.g., W. A. Ritschel, Die Tablette, 2. Auflage, Editio Cantor Verlag Aulendorf, 2002.

In comparison to formulations providing immediate release, formulations providing prolonged release upon oral administration have the advantage that they need to be administered less frequently, typically once daily or twice daily. This can reduce peak plasma pharmacologically active ingredient concentrations and fluctuations between peak and trough plasma pharmacologically active ingredient concentrations which in turn may improve tolerability.

US 2009/0005408 relates to a process for the production of solid pharmaceutical dosage forms with at least reduced potential for abuse, by a) shaping a formulation mixture containing at least one active ingredient with potential for abuse and at least one physiologically acceptable polymer, which exhibits a breaking strength of at least 500 N, into formed articles by application of force, b) optionally singulating the formed articles and optionally in each case grading them by size and, c) after or during heating at least to the softening point of the physiologically acceptable polymer, exposing the formed articles to force until they have a breaking hardness of at least 500 N, optionally providing them with a cover and optionally mixing all the formed articles back together again.

US 2009/0022798 discloses formulations and methods for the delivery of drugs, particularly drugs of abuse, having an abuse-relevant drug substantially confined in the core and a non-abuse relevant drug in a non-core region. These formulations have reduced potential for abuse. In the formulation, preferably the abuse relevant drug is an opioid and the non-abuse relevant drug is acetaminophen or ibuprofen. More preferably, the opioid is hydrocodone, and the non-abuse relevant analgesic is acetaminophen. In certain preferred embodiments, the dosage forms are characterized by resistance to solvent extraction; tampering, crushing or grinding. Certain embodiments relate to dosage forms providing an initial burst of release of drug followed by a prolonged period of controllable drug release. When providing these dosage forms with tamper-resistant properties, however, the initial burst of release of drug is difficult to achieve, as tamper-resistance typically relies on the presence of polymers that act as release matrix material slowing down the release of the drug from the dosage form. The non-core layer of said drug product is explicitly applied using a film-coating process. A film-coating process is disadvantageous due to the high cost it produces during manufacturing. The film-forming layer material is first dissolved, then sprayed on the core and finally the solvent is removed, all leading to long process times with high energy consumption. Due to the high amount of active that needs to be present in the film-layer, this is a significant disadvantage for a cost-competitive manufacturing of the drug product.

WO 2010/140007 is drawn to a dosage form, particularly a tamper resistant dosage form, comprising: melt-extruded particulates comprising a drug; and a matrix; wherein said melt-extruded particulates are present as a discontinuous phase in said matrix.

WO 2013/017234 relates to a tamper-resistant tablet comprising a matrix material in an amount of more than one third of the total weight of the tablet; and a plurality of coated particulates in an amount of less than two thirds of the total weight of the tablet; wherein said particulates comprise a pharmacologically active compound and a physiologically acceptable polymer, preferably a polyalkylene oxide; and form a discontinuous phase within the matrix material; which preferably provides under in vitro conditions immediate release of the pharmacologically active compound in accordance with Ph. Eur.

The properties of the pharmaceutical dosage forms of the prior art are not satisfactory in every respect.

It is an object of the invention to provide pharmaceutical dosage forms which have advantages over the pharmaceutical dosage forms of the prior art.

This object has been achieved by the subject-matter described hereinbelow.

A first aspect of the invention relates to a tamper-resistant pharmaceutical dosage form comprising one or more particles, wherein each of said one or more particles
  comprises a pharmacologically active ingredient and a physiologically acceptable polymer;
  has a breaking strength of at least 300 N;
  has a weight of at least 2 mg; and
  optionally, comprises a film-coating;
wherein the total weight of the pharmaceutical dosage form is greater than the total weight of said one or more particles.

It has been surprisingly found that tamper-resistant pharmaceutical dosage forms can be provided, which do not require press-forming of a thermoformed intermediate and thus, are easier to manufacture. The crude intermediate that is obtained e.g. by thermoforming such as hot-melt extrusion can be incorporated in the pharmaceutical dosage form as such. Subsequent process steps following thermoforming can be omitted, particularly shaping of the thermoformed intermediate by means of a tabletting tool and film coating. In this regard, it has also been surprisingly found that standard equipment for the manufacture of pharmaceutical dosage forms can be used, thus facilitating the manufacture of the dosage forms.

Further, it has been surprisingly found that the advantages conventionally achieved by film-coating can alternatively be achieved, e.g. by placing the thermoformed intermediates in capsules. In this regard, it has also been surprisingly found that placing the thermoformed intermediates in capsules is advantageous compared to film coating. The dyes are neither limited to specific dyes such as iron oxides nor is a protective layer needed in order to ensure color stability of the dyes contained in the capsules. Thus, when placing the one or more thermoformed intermediates in capsules according to the invention, neither laborious press-forming nor laborious two-layered film coating is needed and the full range of admitted dyes including azo compounds can be used in order to provide the dosage forms with any desired color or combination of colors, e.g. one part of the capsule in a first color, the other part of the capsule in a second color.

Still further, it has been surprisingly found that tamper-resistant pharmaceutical dosage forms can be provided that can be chewed to a certain degree without significantly deteriorating tamper-resistance and without significantly altering drug release. The one or more particles contained in the pharmaceutical dosage form cannot be spontaneously chewed and thus, provide satisfactory tamper-resistance. The overall pharmaceutical dosage form, however, does not have a significantly increased breaking strength such that it can be chewed to a certain degree, until chewing disrupts the pharmaceutical dosage form to the level of the one or more particles. Yet further, it has been surprisingly found that tamper-resistant pharmaceutical dosage forms can be provided which can be divided into subunits that can be swallowed separately without altering drug release and without deteriorating tamper-resistance. Patient compliance can thus be improved. In particular, it has been unexpectedly found that when dividing the total dose of the pharmacologically active ingredient that is contained in a single particle providing tamper-resistance into 2 or 3 subunits, the release profile is not significantly altered and the tamper-resistance is maintained. This is particularly surprising as one would typically expect that when decreasing the particle size, release would be accelerated and tamper-resistance such as breaking strength and extractability would be deteriorated.

Moreover, it has been surprisingly found that a large variety of tamper-resistant dosage forms can be easily provided simply by combining different particles containing pharmacologically active ingredient. Said different particles may differ in the nature of the pharmacologically active ingredient, the dose of the pharmacologically active ingredient, the release profile of the pharmacologically active ingredient, and the like. By combining these properties with one another, tamper-resistant pharmaceutical dosage forms can be tailored for any specific use.

Furthermore, it has been surprisingly found that tamper-resistant pharmaceutical dosage forms can be provided which can be easily manufactured and the composition of which can be easily varied e.g. with respect of dosage of active pharmaceutical ingredient, nature of active pharmaceutical ingredient, combinations of more than a single active pharmaceutical ingredient, release characteristics, and the like.

Unless expressly stated otherwise, all percentages are by weight (wt.-%).

For the purpose of specification, the term "pharmaceutical dosage form" refers to a pharmaceutical entity which contains the pharmacologically active ingredient and which is to be administered to a patient (dose unit). It may be compressed or molded during manufacture, and it may be of almost any size, shape, weight, and color. The pharmaceutical dosage form is preferably solid or semisolid.

The pharmaceutical dosage form is preferably intended for oral administration. It is preferably provided in form of a single body that can be easily swallowed by a patient. Typical examples of pharmaceutical dosage forms according to the invention include, but are not limited to tablets and capsules.

The tamper-resistant pharmaceutical dosage form according to the invention comprises one or more particles.

For the purpose of specification, any property of each of the "one or more particles" does not mean that any particle that is contained in the pharmaceutical dosage form must exhibit this property. It is sufficient that the one or more particles containing the pharmacologically active ingredient and the physiologically acceptable polymer that have a weight of at least 2 mg and a breaking strength of at least 300 N, i.e. optionally a subgroup of all particles contained in the pharmaceutical dosage form, exhibit such property.

For the purpose of specification, the term "particle" as used herein refers to a piece of matter, namely any physically distinct particulate entity of the pharmaceutical dosage form that contains the pharmacologically active ingredient as well as the physiologically acceptable polymer and that can be distinguished from another physically distinct entity of the pharmaceutical dosage form. Preferably, every particle is solid or semisolid.

The one or more particles of the pharmaceutical dosage form preferably do not consist of the pharmacologically active ingredient and the physiologically acceptable polymer, but contain further ingredients such as pharmaceutical excipients. Thus, the one or more particles can be regarded as greater units of compacted, granulated, congealed or otherwise agglomerated material, comprising inter alia but preferably not consisting of the pharmacologically active ingredient and the physiologically acceptable polymer.

In a preferred embodiment, besides the pharmacologically active ingredient and the physiologically acceptable polymer the one or more particles comprise another, i.e. second pharmacologically active ingredient. In another preferred embodiment, besides the pharmaceutically active ingredient and the physiologically acceptable polymer the one or more particles do not comprise another, i.e. second pharmacologically active ingredient; preferably, the pharmaceutical dosage form does not contain another, i.e. second pharmacologically active ingredient and/or the total amount of the pharmacologically active ingredient is contained in the one or more particles, i.e. preferably neither a portion of the pharmacologically active ingredient nor another, i.e. second pharmacologically active ingredient, is present outside the one or more particles.

In another particularly preferred embodiment, none of the one or more particles simultaneously comprises hydromorphone together with naloxone or a physiologically acceptable salt thereof.

Preferably, the total amount of the pharmacologically active ingredient that is contained in the pharmaceutical dosage form according to the invention is contained in the one or more particles, i.e. the pharmaceutical dosage form preferably does not contain other physically distinct entities containing the pharmacologically active ingredient. For example, when the pharmaceutical dosage form is a capsule filled with the one or more particles, the total amount of the pharmacologically active ingredient is preferably contained in the one or more particles, and preferably neither a portion of the pharmacologically active ingredient nor another, i.e. second pharmacologically active ingredient, is present outside the one or more particles but inside the capsule.

Preferably, the total amount of the physiologically acceptable polymer that is contained in the pharmaceutical dosage form according to the invention is contained in the one or more particles, i.e. the pharmaceutical dosage form preferably does not contain other physically distinct entities containing the physiologically acceptable polymer.

Besides the content of the pharmacologically active ingredient and physiologically acceptable polymer, the one or more particles preferably differ from any other physically distinct entity of the pharmaceutical dosage form in at least one of the following properties and can be distinguished by said property: composition of ingredients (e.g. nature and/or amount), total weight, density, hardness, breaking strength, size, shape, color, morphology, coherence (e.g. monolithic mass vs. multitude of particulates) and/or porosity.

The total weight of the pharmaceutical dosage form is greater than the total weight of the one or more particles. This means that the pharmaceutical dosage form contains other constituents besides the one or more particles, but does not exclusively consist of the one or more particles. For example, when the pharmaceutical dosage form is a capsule, it additionally comprises the capsule material, e.g. hard gelatine. When the pharmaceutical dosage form is a tablet, it additionally comprises excipients, e.g. fillers, binders, lubricants and the like.

Preferably the total weight of the one or more particles is at least 50 wt.-%, more preferably at least 60 wt.-%, still more preferably at least 70 wt.-%, yet more preferably at least 75 wt.-%, even more preferably at least 80 wt.-%, most preferably at least 85 wt.-%, and in particular at least 90 wt.-% of the total weight of the pharmaceutical dosage form.

For the purpose of specification, "further excipient(s)" generally refers to additional matter of the pharmaceutical dosage form that is present in addition to the one or more particles and that causes the total weight of the pharmaceutical dosage form to be greater than the total weight of the one or more particles. Thus, "further excipient(s)" includes the capsule material when the pharmaceutical dosage form is a capsule, as well as fillers, binders, lubricants, and the like, when the pharmaceutical dosage form is a tablet.

Accordingly, the total volume of the pharmaceutical dosage form is preferably greater than the total volume of the one or more particles.

Preferably, each of the one or more particles of the pharmaceutical dosage form covers at least 1 vol.-%, or at least 2 vol.-%, or at least 5 vol.-%, more preferably at least 10 vol.-% or at least 15 vol.-%, still more preferably at least 17.5 vol.-% or at least 20 vol.-%, yet more preferably at least 22.5 vol.-% or at least 25 vol.-%, even more preferably at least 30 vol.-% or at least 35 vol.-%, most preferably at least 40 vol.-%, and in particular at least 45 vol.-%, of the total volume of the pharmaceutical dosage form, which preferably is capsule. Thus, physically distinct entities that are so small that they do not cover such portion of the total volume of the pharmaceutical dosage form are typically not to be regarded as "particle" in the meaning of the invention.

It has been surprisingly found that when the pharmaceutical dosage form is a capsule, it is advantageous to minimize the empty volume inside the capsule such that the one or more particles fill as much of the inside of the capsule as possible. This is particularly relevant when the one or more particles are thermoformed intermediates that are not further press-formed but placed inside the capsule in form of the crude intermediates as such. It has been found that when the movability of the one or more particles inside the capsules is limited or fully impeded, comparatively sharp edges e.g. at the cut surfaces of extruded cylinders do not cause problems upon transportation. Otherwise, when the one or more particles are comparatively small compared to the inner volume of the capsule, they are moveable to a certain extent and may be accelerated within the capsules during transportation of the dosage forms. In the worst case, the physical impact of the accelerated particles hitting the inner wall of the capsule material may cause damages of the capsule, especially over the sharp edges at the cut surfaces of extruded cylinders. When the empty volume inside the capsules is minimized, however, the particles cannot receive sufficient energy in the course of shaking and moving the capsules, e.g. during transportation.

In a preferred embodiment, the pharmaceutical dosage form is a capsule containing only a single particle, wherein the volume of said single particle is at least 30 vol.-% or at least 35 vol.-%, more preferably at least 40 vol.-% or at least 45 vol.-%, still more preferably at least 50 vol.-% or at least 55 vol.-%, yet more preferably at least 60 vol.-% or at least 65 vol.-%, even more preferably at least 70 vol.-% or at least 75 vol.-%, most preferably at least 80 vol.-% or at least 85 vol.-%, and in particular at least 90 vol.-% or at least 95 vol.-%, of the total inner volume of the capsule.

In another preferred embodiment, the pharmaceutical dosage form is a capsule containing only a single particle and having an empty volume of at most 70 vol.-% or at most 65 vol.-%, more preferably at most 60 vol.-% or at most 55 vol.-%, still more preferably at most 50 vol.-% or at most 45 vol.-%, yet more preferably at most 40 vol.-% or at most 35 vol.-%, even more preferably at most 30 vol.-% or at most 25 vol.-%, most preferably at most 20 vol.-% or at most 15 vol.-%, and in particular at most 10 vol.-% or at most 5 vol.-%, of the total inner volume of the capsule.

Preferably, the pharmaceutical dosage form is a capsule containing only a single particle, wherein the single particle contains the total amount of the pharmacologically active ingredient that is contained in the pharmaceutical dosage form, the total amount of the physiologically acceptable polymer that is contained in the pharmaceutical dosage form, and the total amount of excipients that are optionally contained in the pharmaceutical dosage form besides the capsule material. Thus, according to this preferred embodiment, the pharmaceutical dosage form consists of the capsule and the single particle such that the inside of the capsule contains the single particle and optionally air or gas, but nothing else.

The one or more particles and the further excipient(s) of the pharmaceutical dosage form are separate of one another, i.e. are at different locations of the pharmaceutical dosage form. However, it is possible that the further excipient(s) partially or completely surround(s) the one or more particles. Nevertheless, it is not possible that a given location of the pharmaceutical dosage form contains both, matter of the one or more particles and simultaneously matter of the further excipient(s).

For example, the further excipient(s) may be a powdery material or a coherent matrix material in which e.g. the one or more particles may be embedded, or a spatially confined area within the pharmaceutical dosage form such as a layer of a multilayer pharmaceutical dosage form. When the pharmaceutical dosage form is provided in form of a capsule filled with a multitude of pellets and a powder, every pellet that contains pharmacologically active ingredient and physiologically acceptable polymer can be regarded as an individual of the one or more particles and the powder can be regarded as further excipient(s).

The one or more particles and the further excipient(s) of the pharmaceutical dosage form can be distinguished from one another.

The pharmaceutical dosage form according to the invention comprises at least one particle containing pharmacologically active ingredient and physiologically acceptable polymer (monolith) but may also contain a plurality of particles containing pharmacologically active ingredient and physiologically acceptable polymer (e.g. multitude of particles).

The pharmaceutical dosage form according to the invention preferably contains at least two particles containing pharmacologically active ingredient and physiologically acceptable polymer that are identical or differ from one another.

In a preferred embodiment, when the pharmaceutical dosage form according to the invention comprises a plurality of particles containing pharmacologically active ingredient and physiologically acceptable polymer, the individual particles are preferably of essentially the same type and nature, e.g. composition, total weight, density, hardness, breaking strength, size, shape, color, morphology, coherence and/or porosity.

In another preferred embodiment, when the pharmaceutical dosage form according to the invention comprises a plurality of particles containing pharmacologically active ingredient and physiologically acceptable polymer, the individual particles are preferably of different type and nature, i.e. differ from one another with respect to e.g. composition, total weight, density, hardness, breaking strength, size, shape, color, morphology, coherence and/or porosity. For example, the particles containing pharmacologically active ingredient and physiologically acceptable polymer may contain different quantities of the physiologically acceptable polymer and may provide e.g. prolonged release of the pharmacologically active ingredient. Prolonged release may be achieved e.g. by embedding the pharmacologically active ingredient in a polymer matrix comprising the physiologically acceptable polymer. Due to the different quantities of the physiologically acceptable polymer, the different particles containing pharmacologically active ingredient and physiologically acceptable polymer may provide different in vitro release profiles of the pharmacologically active ingredient.

Preferably, the pharmaceutical dosage form contains not more than 10 particles containing pharmacologically active ingredient and physiologically acceptable polymer, more preferably not more than 9, still more preferably not more than 8, yet more preferably not more than 7, even more preferably not more than 6, most preferably not more than 5, and in particular not more than 4 particles containing pharmacologically active ingredient and physiologically acceptable polymer. Preferably, the pharmaceutical dosage form contains 1, 2 or 3 particles containing pharmacologically active ingredient and physiologically acceptable polymer.

The pharmaceutical dosage form according to the invention comprises at least one further excipient but preferably contains a plurality of further excipients. Said further excipient(s) may also be present in particulate form. In a preferred embodiment, the pharmaceutical dosage form contains additional particle(s) besides the one or more particles containing pharmacologically active ingredient and physiologically acceptable polymer, e.g. particles which
(i) do not contain the pharmacologically active ingredient, and/or
(ii) do not contain the physiologically acceptable polymer, and/or
(iii) do not have a breaking strength of at least 300 N, and/or
(iv) have a weight of less than 2 mg.

In a preferred embodiment, the one or more particles and the further excipient(s) each constitute a spatially confined area within the pharmaceutical dosage form. According to this embodiment, the one or more particles and/or further excipient(s) preferably form a layer, a coating, a core or a mantle of the pharmaceutical dosage form which is preferably in the form of a tablet.

BRIEF DESCRIPTION OF THE DRAWINGS

Preferred embodiments of tablets according to the invention comprising the one or more particles containing pharmacologically active ingredient and physiologically acceptable polymer and the further excipient(s) are illustrated in FIG. 1.

In another preferred embodiment, the one or more particles are contained in a container, e.g. a hard gelatine capsule. Besides the capsule material, the capsules may optionally contain further excipient(s).

Figure 1:
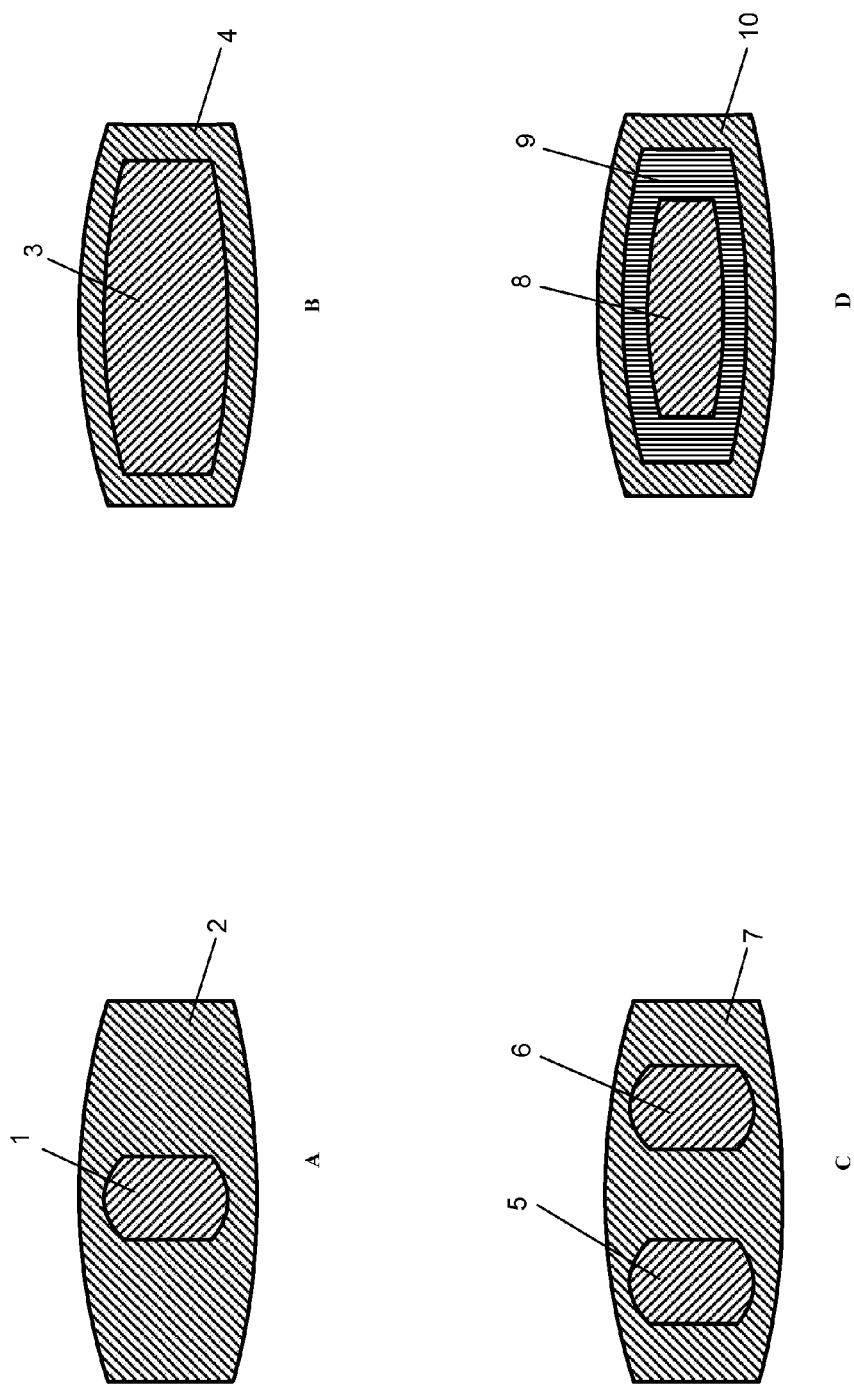
FIG. 1A schematically illustrates a mantle tablet comprising a single particle (1) containing pharmacologically active ingredient and physiologically acceptable polymer as core and further excipient(s) (2) surrounding said particle (1).
FIG. 1B schematically illustrates another mantle tablet comprising a single particle (3) containing pharmacologically active ingredient and physiologically acceptable polymer as core and further excipient(s) (4) surrounding said particle (3). Compared to the mantle tablet of FIG. 1A, the particle (3) is substantially larger than particle (1).
FIG. 1C schematically illustrates a tablet comprising two particles (5) and (6) containing pharmacologically active ingredient and physiologically acceptable polymer and further excipient(s) (7) forming a continuous matrix in which the two particles (5) and (6) are embedded. Thus, particles (5) and (6) form a discontinuous phase in the further excipient(s) (7).
FIG. 1D schematically illustrates a mantle tablet comprising a single particle (8) containing pharmacologically active ingredient and physiologically acceptable polymer as core and further excipient(s) (9) surrounding said core as an intermediate layer and further excipient(s) (10) surrounding said intermediate layer.
Figure 2:
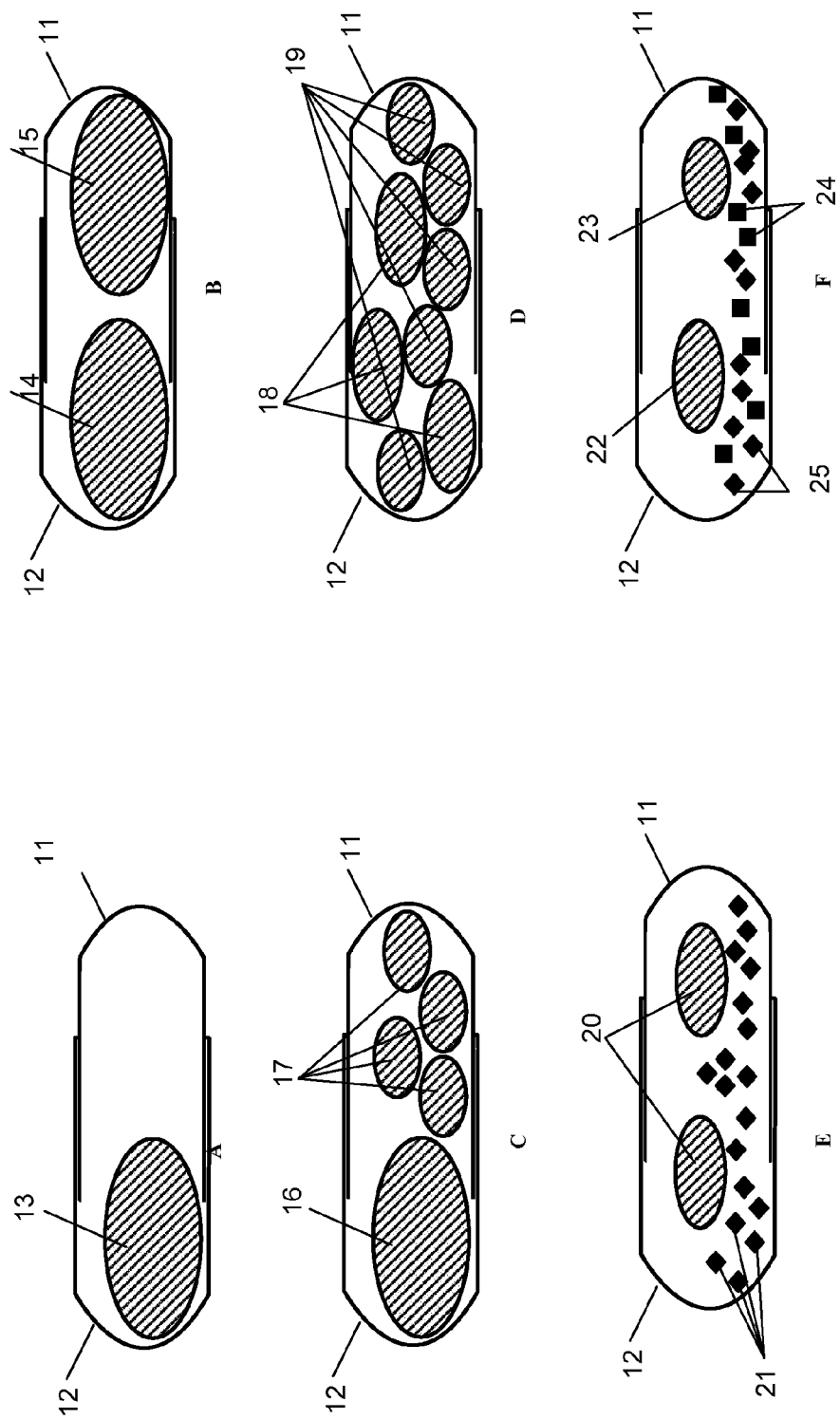

Preferred embodiments of capsules according to the invention comprising one or more particles containing pharmacologically active ingredient and physiologically acceptable polymer and optionally, further excipient(s) are illustrated in FIG. 2.

FIG. 2A schematically illustrates a capsule formed of capsule body (11) and capsule lid (12). The capsule contains a single particles (13) containing pharmacologically active ingredient and physiologically acceptable polymer. Besides particle (13) and the capsule material contained in capsule body (11) and capsule lid (12), the dosage form does not contain further excipient(s).

FIG. 2B schematically illustrates a capsule formed of capsule body (11) and capsule lid (12) and containing two particles (13) and (14) containing pharmacologically active ingredient and physiologically acceptable polymer. Besides particles (13) and (14) and the capsule material contained in capsule body (11) and capsule lid (12), the dosage form does not contain further excipient(s).

FIG. 2C schematically illustrates a capsule formed of capsule body (11) and capsule lid (12) and containing one particle (16) containing pharmacologically active ingredient and physiologically acceptable polymer, and four particles (17) containing pharmacologically active ingredient and physiologically acceptable polymer. Thus, the capsule is filled with a total of five particles each containing pharmacologically active ingredient and physiologically acceptable polymer. While particles (17) are identical, particle (16) differs from particles (17) in size and nature. Besides particles (16) and (17) and the capsule material contained in capsule body (11) and capsule lid (12), the dosage form does not contain further excipient(s).

FIG. 2D schematically illustrates a capsule formed of capsule body (11) and capsule lid (12) and containing three particles (18) containing pharmacologically active ingredient and physiologically acceptable polymer and five particles (19) containing pharmacologically active ingredient and physiologically acceptable polymer. Thus, the capsule is filled with a total of eight particles each containing pharmacologically active ingredient and physiologically acceptable polymer. While particles (18) are identical and particles (19) are identical, particles (18) differ from particles (19) in size and nature. Besides particles (18) and (19) and the capsule material contained in capsule body (11) and capsule lid (12), the dosage form does not contain further excipient(s).

FIG. 2E schematically illustrates a capsule formed of capsule body (11) and capsule lid (12) and containing two particles (20) containing pharmacologically active ingredient and physiologically acceptable polymer as well as a further excipient (21). Thus, in addition to excipients optionally contained in particles (20) and the capsule material contained in capsule body (11) and capsule lid (12), the dosage form contains a further excipient (21).

FIG. 2F schematically illustrates a capsule formed of capsule body (11) and capsule lid (12) and containing one particle (22) containing pharmacologically active ingredient and physiologically acceptable polymer and one particle (23) containing pharmacologically active ingredient and physiologically acceptable polymer. Particle (22) differs from particle (23) in size and nature. The capsule additionally contains further excipient (24) and further excipient (25). Thus, in addition to excipients optionally contained in particles (22) and (23) and the capsule material contained in capsule body (11) and capsule lid (12), the dosage form contains further excipients (24) and (25).

Figure 3:
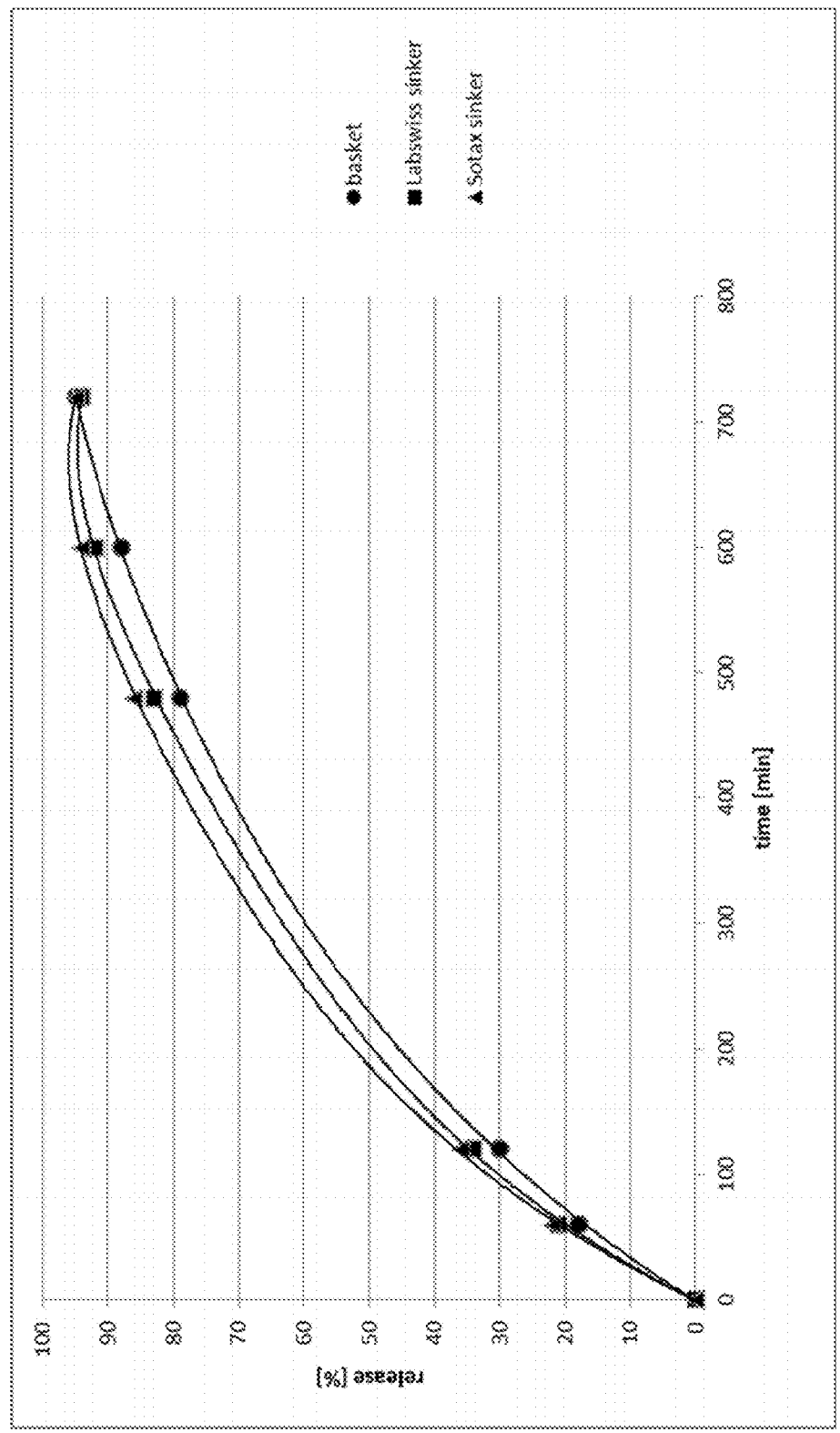

FIG. 3 illustrates the dependence of the dissolution profile on the method of measuring drug release (basket, Labswiss sinker, Sotax sinker).

Figure 4:
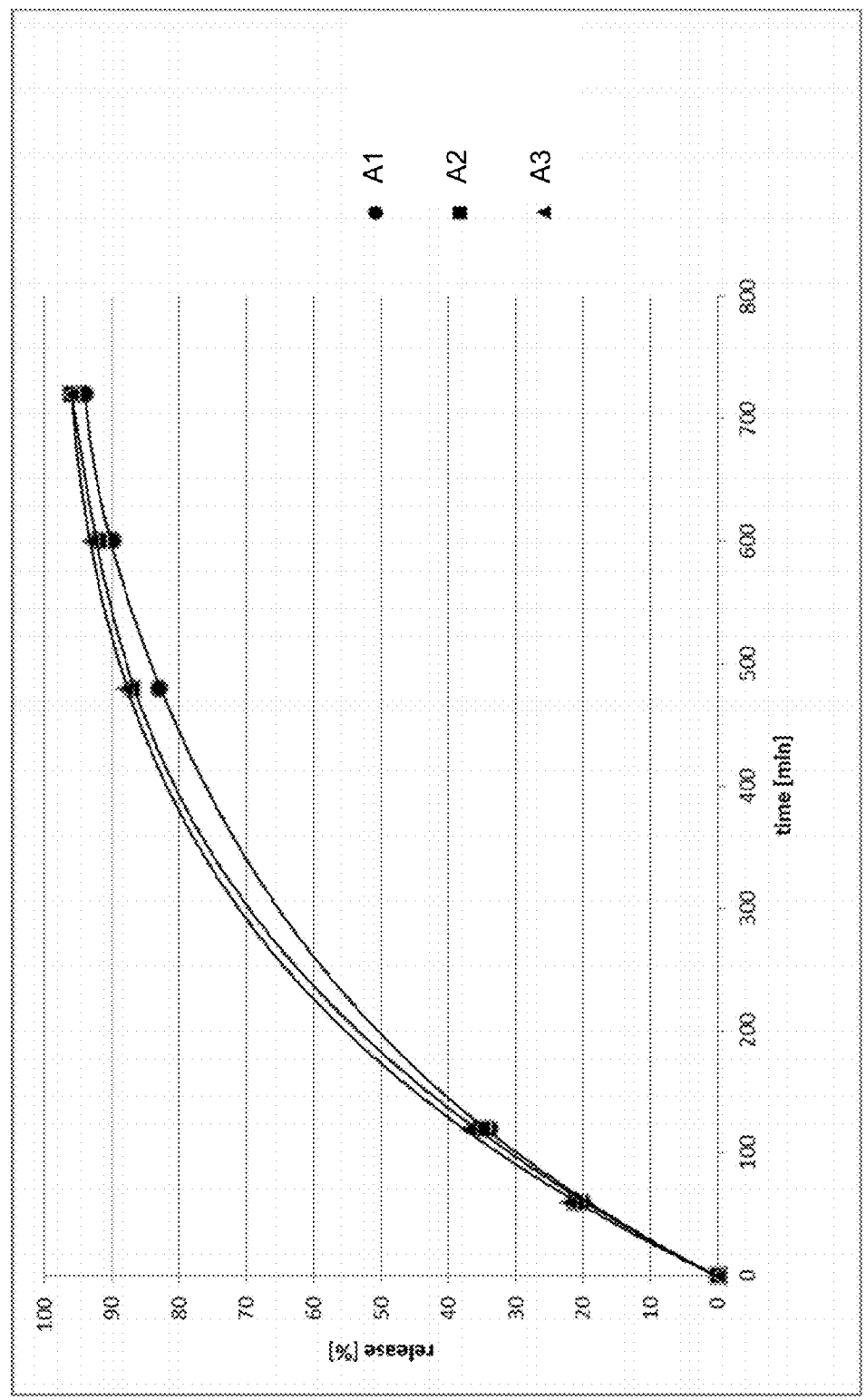

FIG. 4 shows the dissolution profiles of capsules A1, A2 and A3 in 0.1 N HCl.

Figure 5:
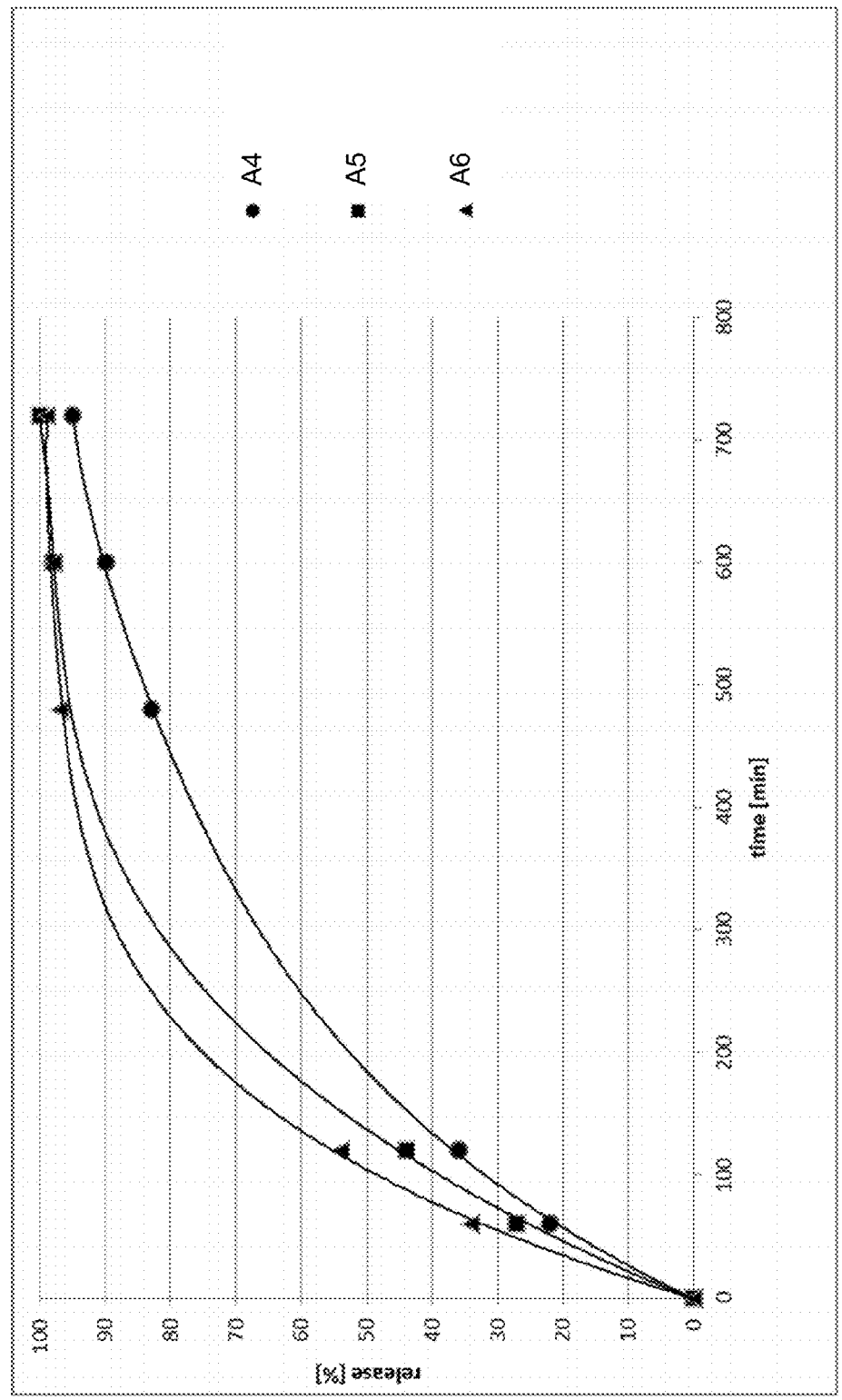

FIG. 5 shows the dissolution profiles of capsules A4, A5 and A6 in 0.1 N HCl.

Figure 6:
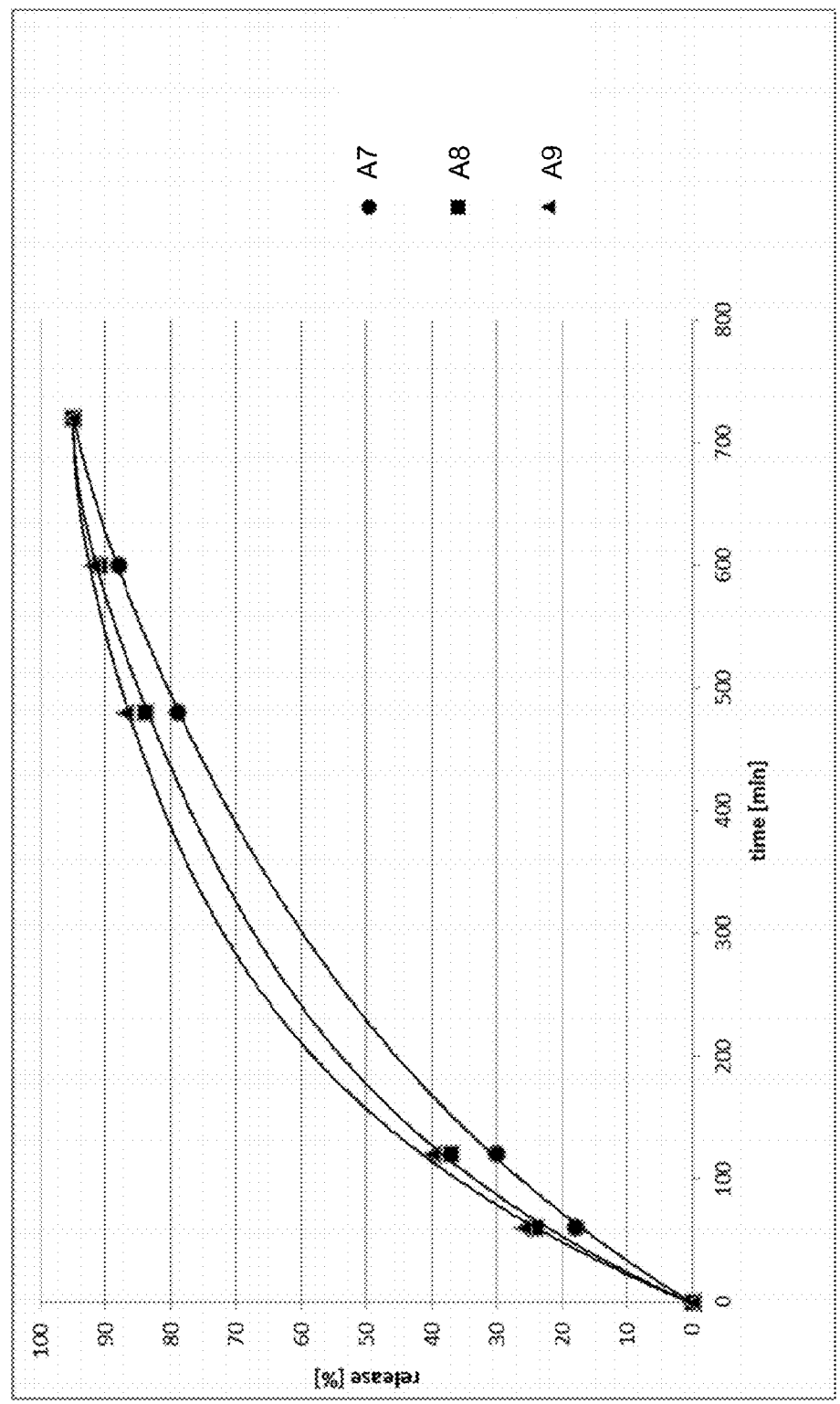

FIG. 6 shows the dissolution profile of capsules A7 and A8 as well as of comparative tablet A9 in 0.1 N HCl.

Figure 7:
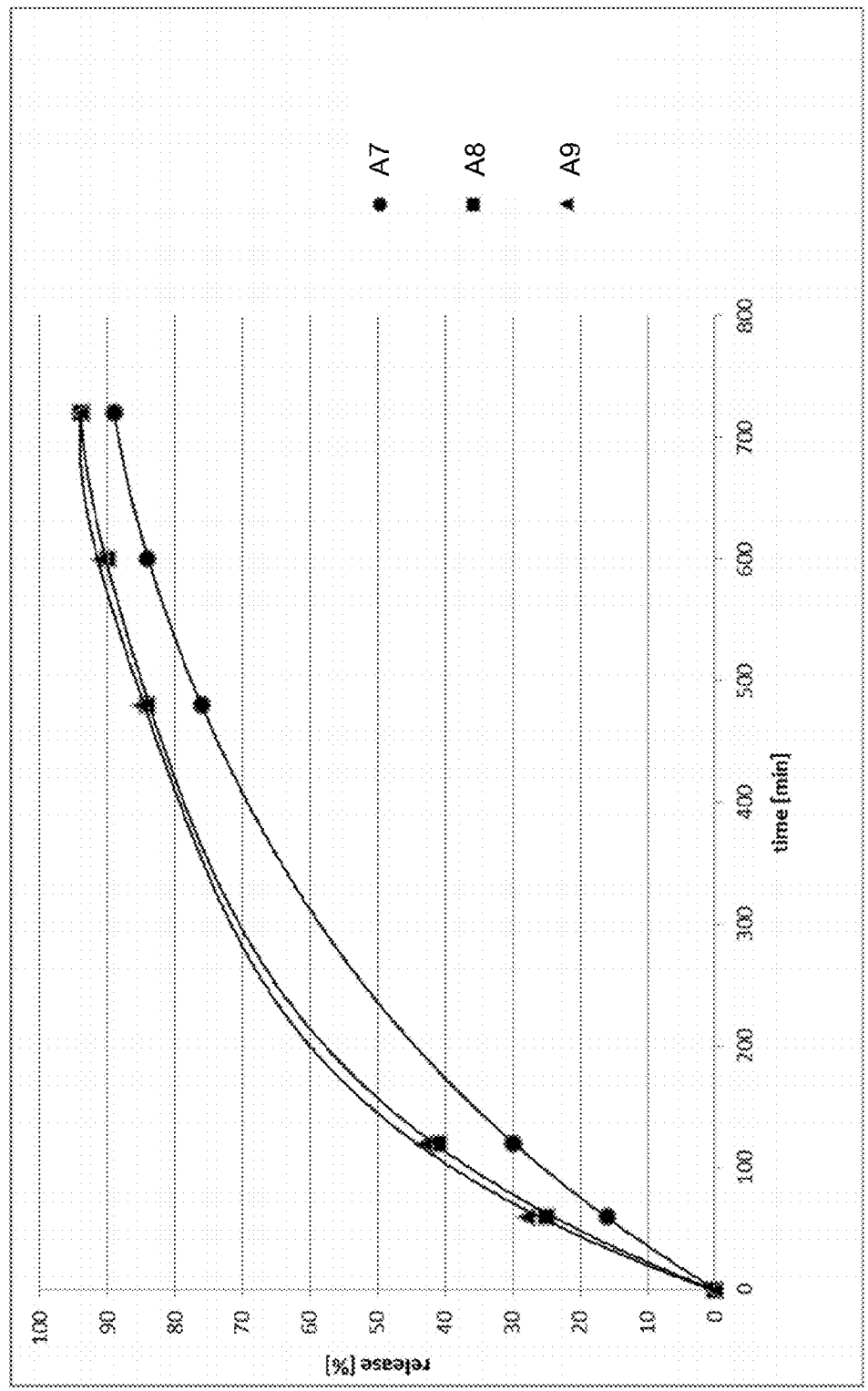

FIG. 7 shows the dissolution profile of capsules A7 and A8 as well as of comparative tablet A9 in SIFsp, pH 6.8.

Figure 8:
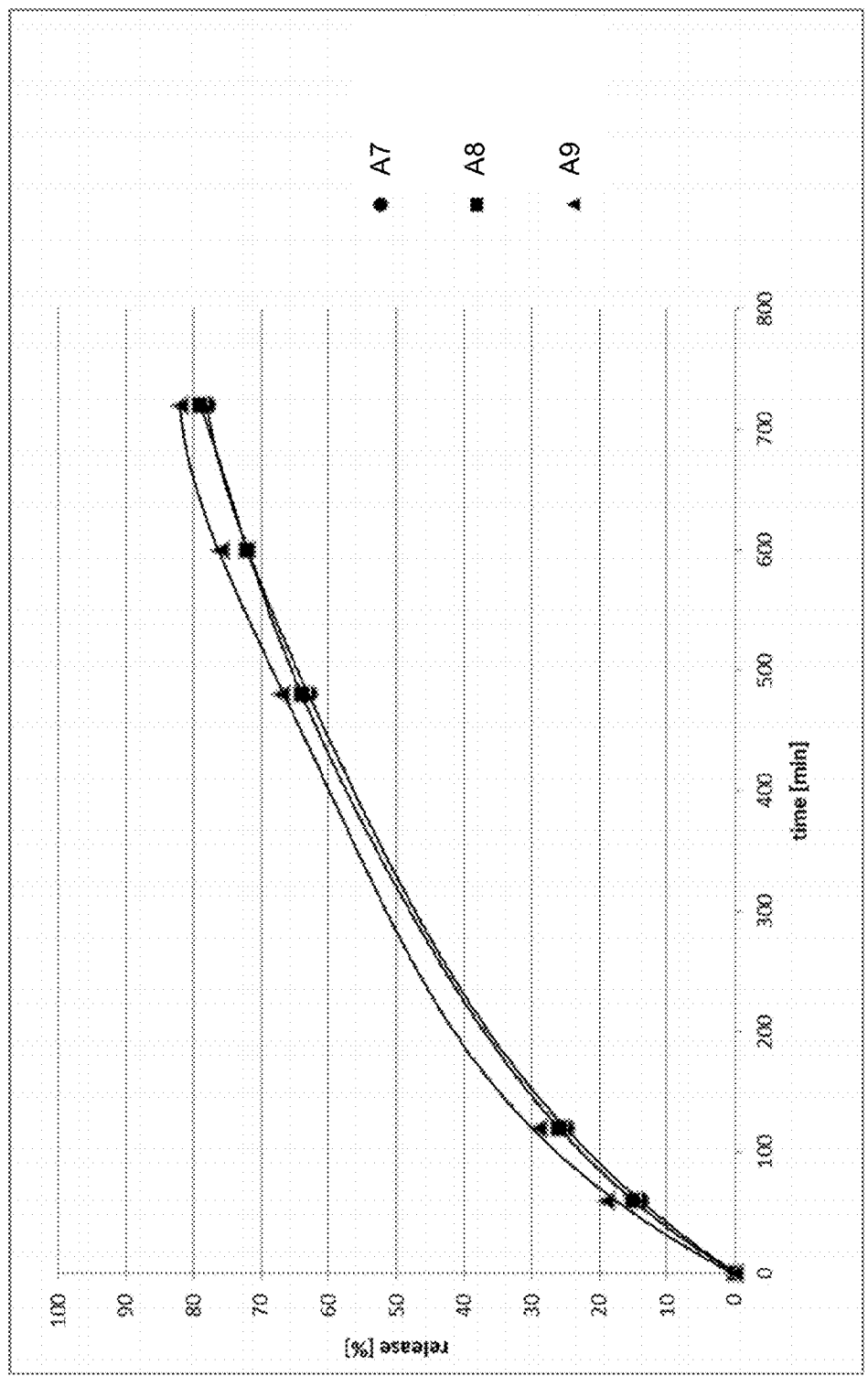

FIG. 8 shows the dissolution profile of capsules A7 and A8 as well as of comparative tablet A9 in 0.1N HCl+40% ethanol.

Figure 9:

FIG. 9 depicts the visual appearance of the comparative tablets A9.

Figure 10:
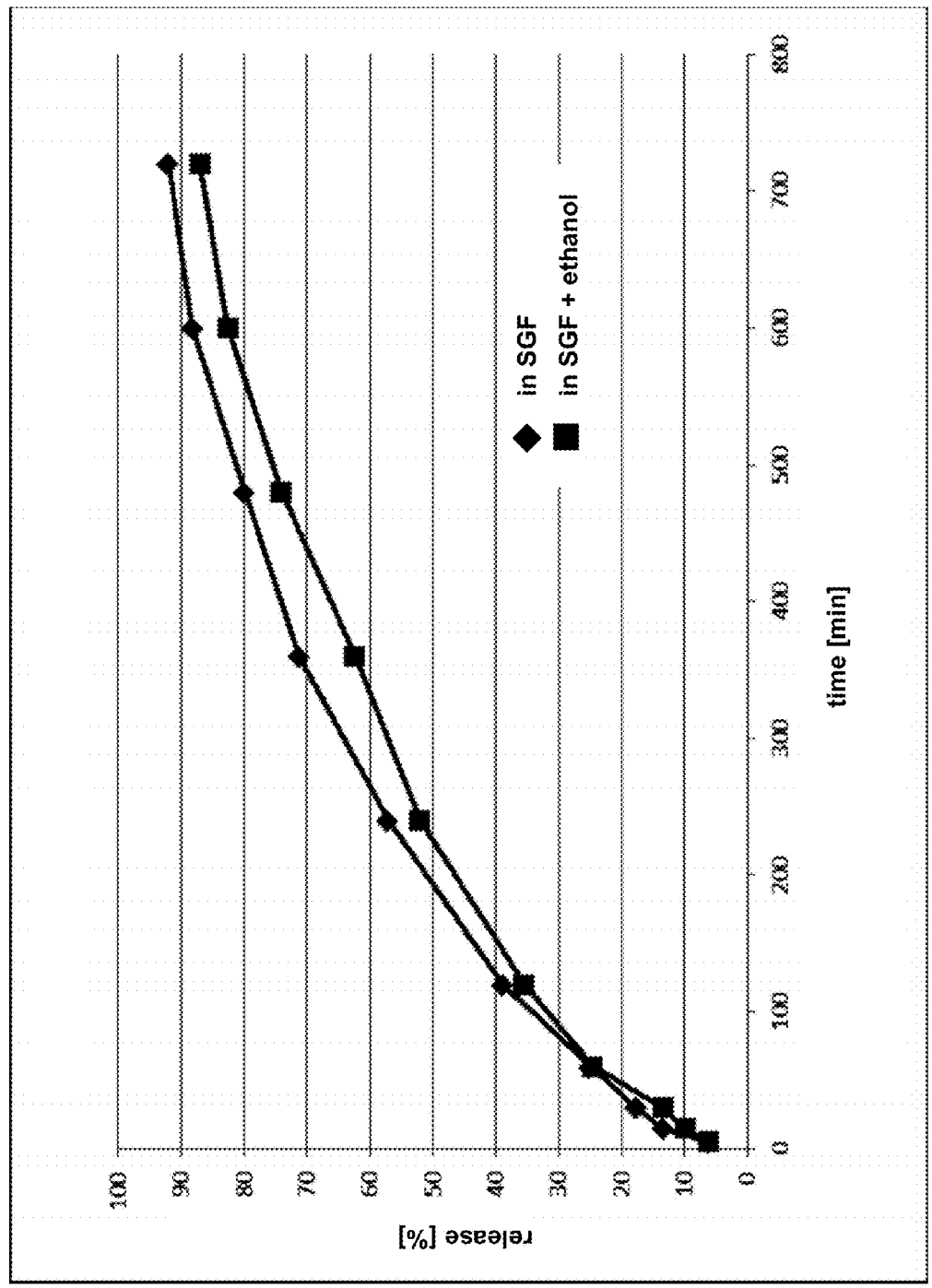

FIG. 10 shows the release profiles of one cut rod determined under in vitro conditions (n=3) using the basket method with sinker according to Ph. Eur. at 75 rpm in 600 mL of SGF (pH 1.2) and SGF (pH 1.2)+40% ethanol, respectively.

Figure 11:
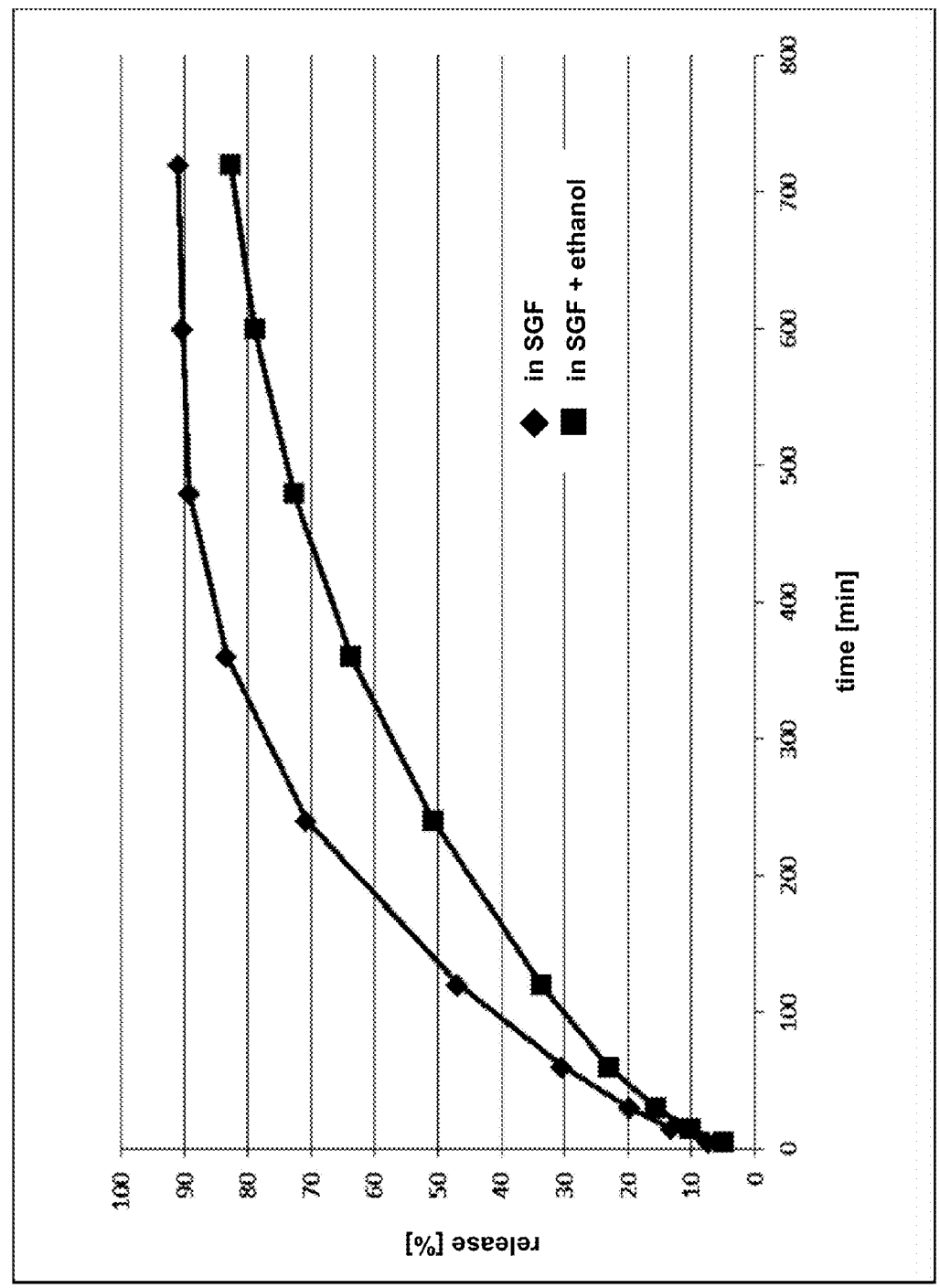

FIG. 11 shows the release profiles of two cut rods determined under in vitro conditions (n=3) using the basket method with sinker according to Ph. Eur. (one sinker per cut rod) at 75 rpm in 600 mL of SGF (pH 1.2) and SGF (pH 1.2)+40% ethanol, respectively.

Figure 12:
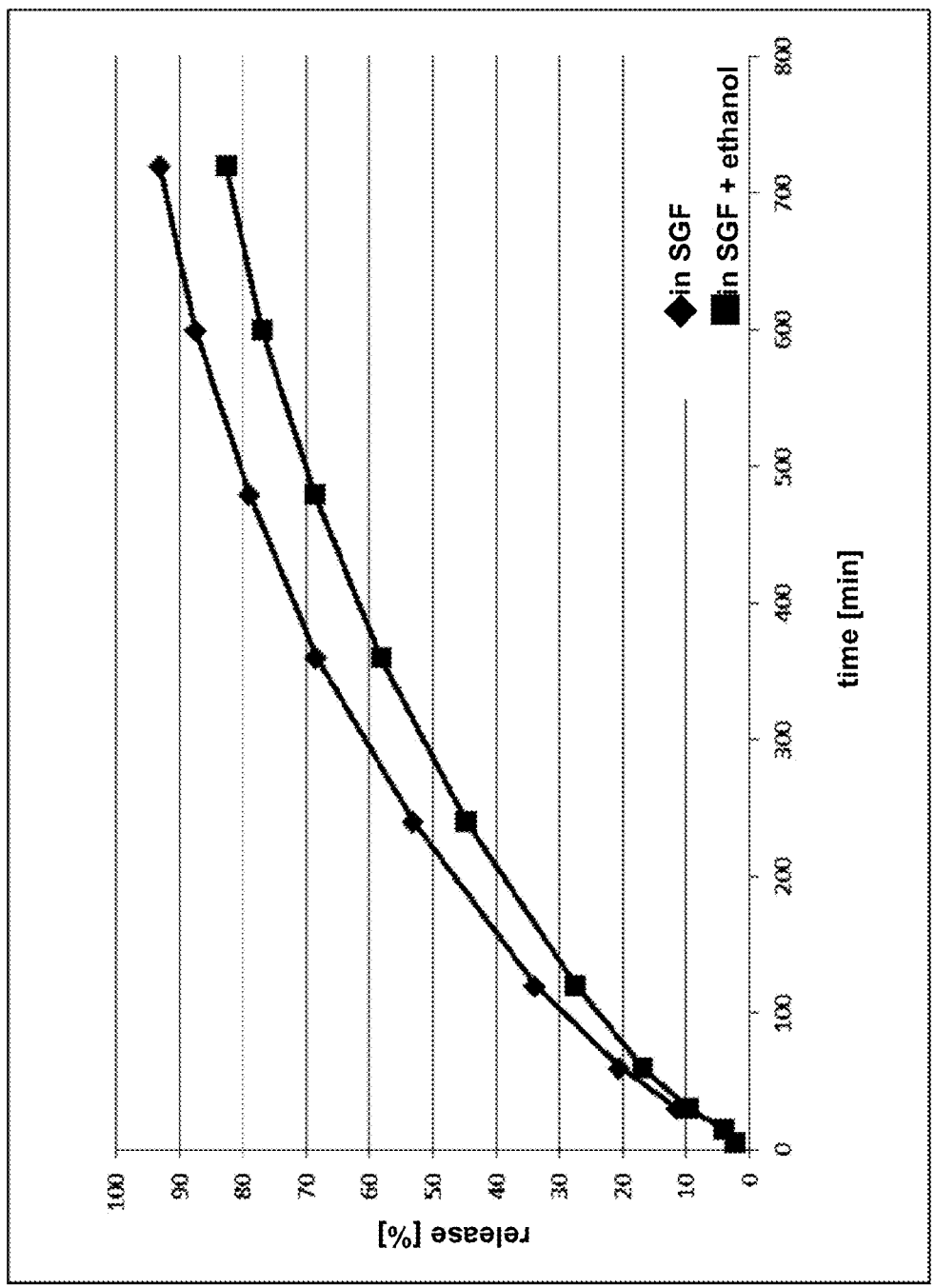

FIG. 12 shows the release profiles of one cut rod in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Figure 13:
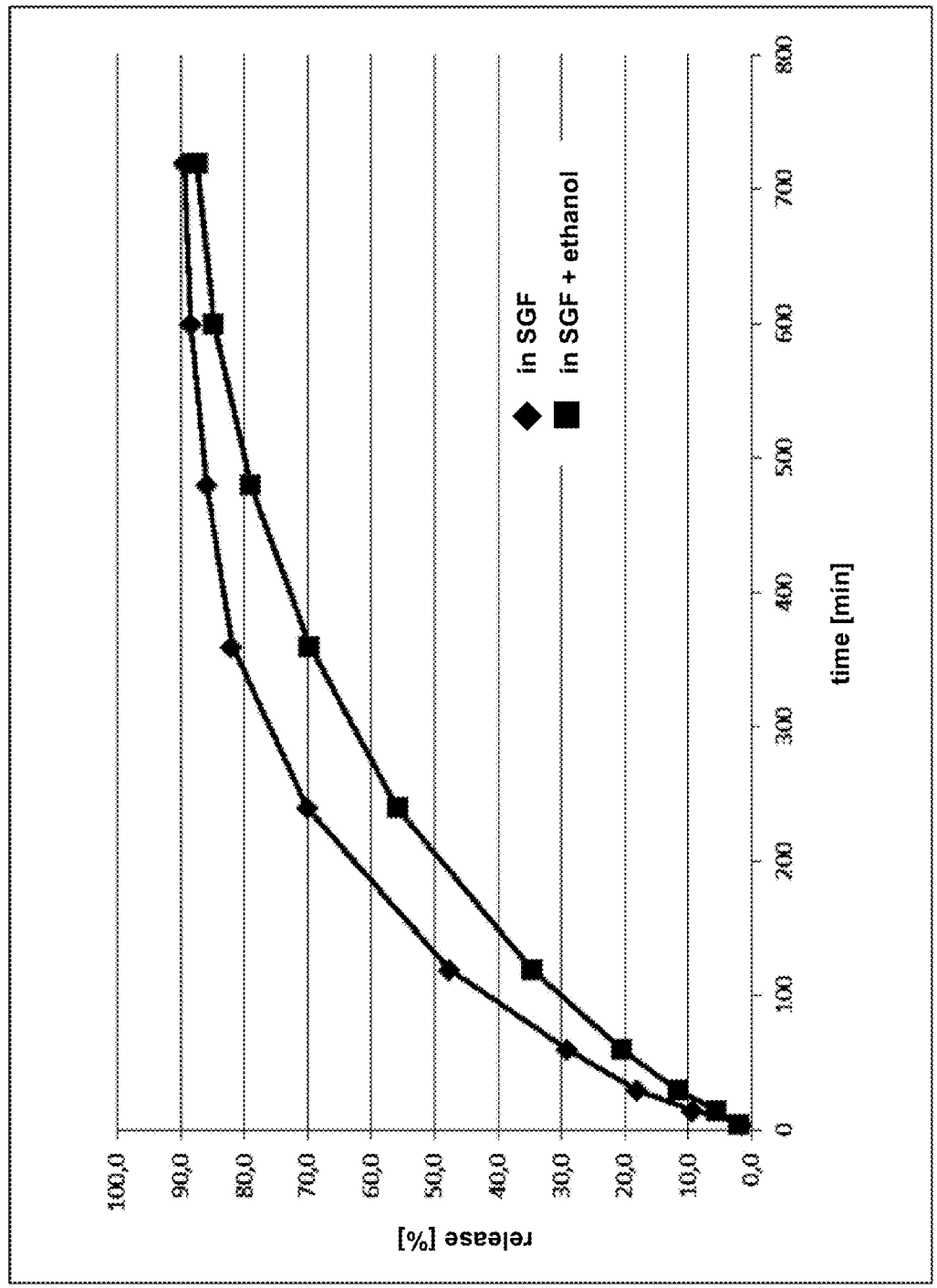

FIG. 13 shows the release profiles of two cut rods and a lactose tablet in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Figure 14:
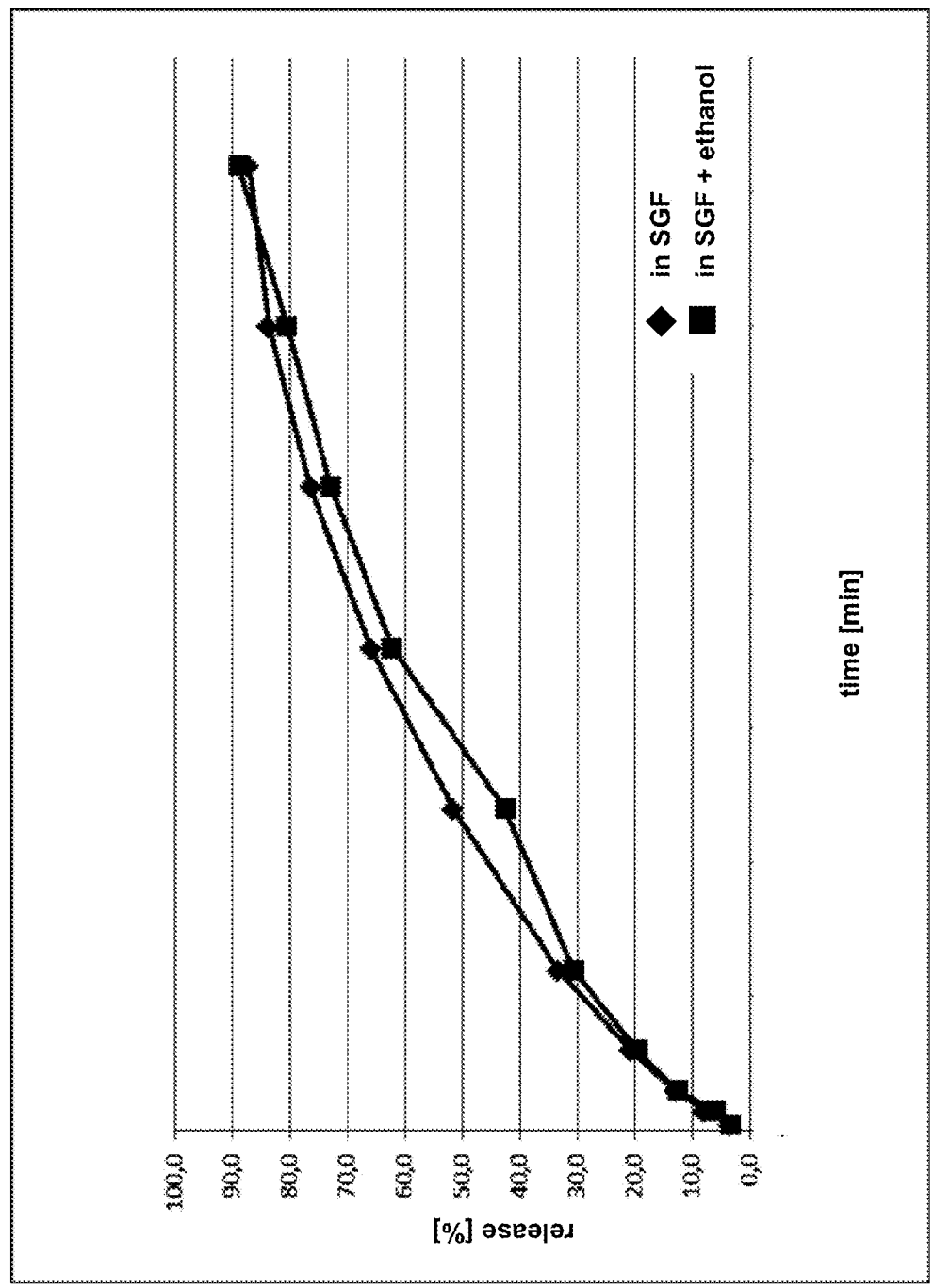

FIG. 14 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

Figure 15:
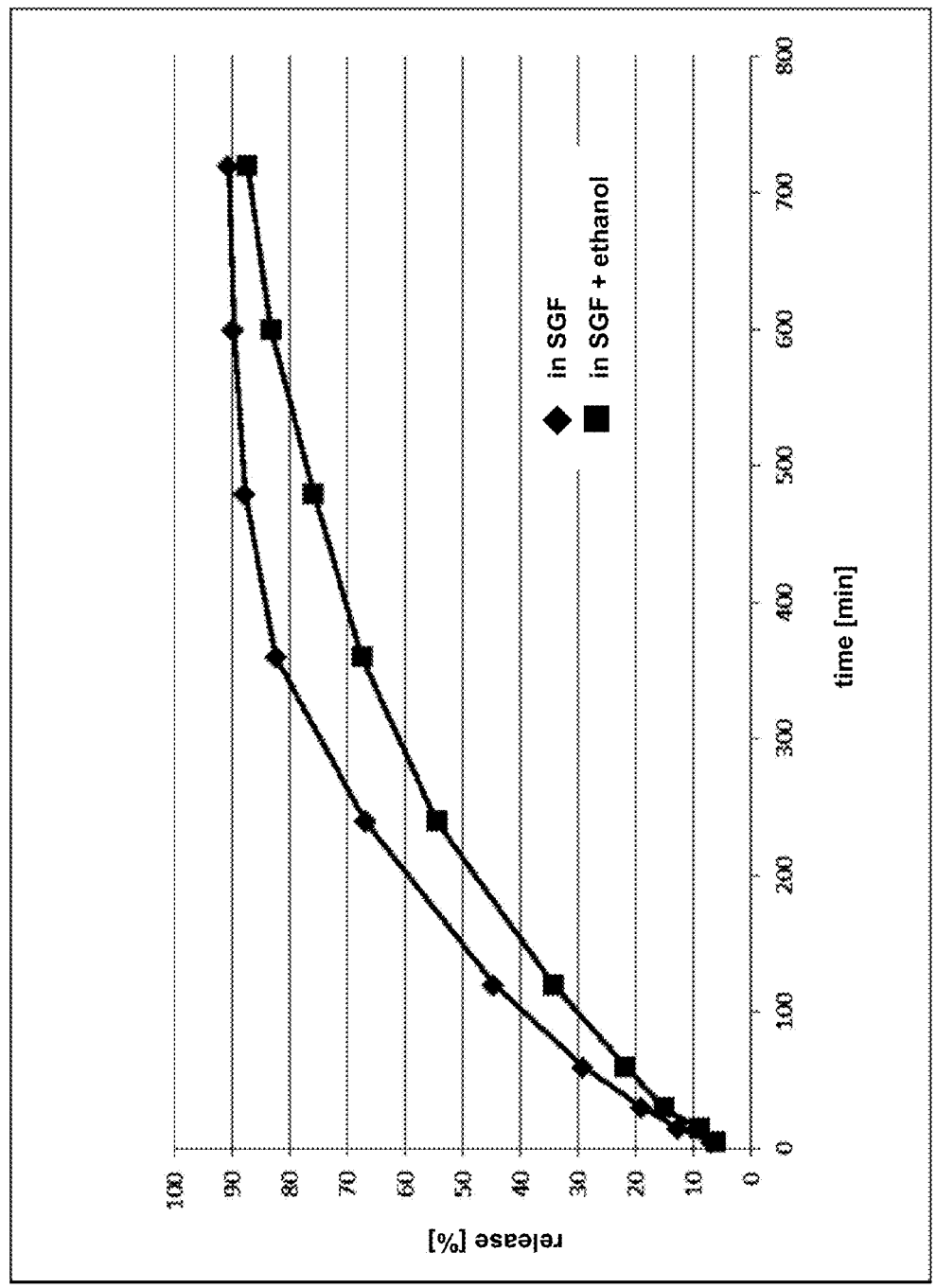

FIG. 15 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

FIGS. 16 to 20 show combinations of the release profiles obtained from Examples CR4, CR5, A10, A11, M1 and M2.

Preferably, the total content of the one or more particles containing pharmacologically active ingredient and physiologically acceptable polymer in the pharmaceutical dosage form according to the invention is at most 95 wt.-%, more preferably at most 85 wt.-%, still more preferably at most 75 wt.-%, yet more preferably at most 65 wt.-%, most preferably at most 55 wt.-% and in particular at most 50 wt.-%, based on the total weight of the pharmaceutical dosage form.

Preferably, the total content of the one or more particles in the pharmaceutical dosage form according to the invention is at least 5 wt.-% or at least 10 wt.-%, more preferably at least 15 wt.-% or at least 20 wt.-%, still more preferably at least 25 wt.-% or at least 30 wt.-%, even more preferably at least 35 wt.-% or at least 40 wt.-%, yet more preferably at least 45 wt.-% or at least 50 wt.-%, most preferably at least 55 wt.-% or at least 60 wt.-%, and in particular at least 65 wt.-% or at least 70 wt.-%; based on the total weight of the pharmaceutical dosage form.

Each of the one or more particles containing pharmacologically active ingredient and physiologically acceptable polymer has a weight of at least 2 mg, preferably at least 5 mg, or at least 10 mg, or at least 15 mg, or at least 20 mg, or at least 25 mg; more preferably at least 30 mg, or at least 35 mg, or at least 40 mg, or at least 45 mg, or at least 50 mg; still more preferably at least 55 mg, or at least 60 mg, or at least 65 mg, or at least 70 mg, or at least 75 mg; yet more preferably at least 80 mg, or at least 85 mg, or at least 90 mg, or at least 95 mg, or at least 100 mg; even more preferably at least 110 mg, or at least 120 mg, or at least 130 mg, or at least 140 mg, or at least 150 mg; most preferably at least 160 mg, or at least 170 mg, or at least 180 mg, or at least 190 mg, or at least 200 mg; and in particular at least 220 mg, or at least 240 mg, or at least 260 mg, or at least 280 mg, or at least 300 mg.

In a preferred embodiment, the pharmaceutical dosage form contains a single particle containing pharmacologically active ingredient and physiologically acceptable polymer. According to this embodiment, the single particle containing pharmacologically active ingredient and physiologically acceptable polymer preferably has a weight of at least 120 mg, more preferably at least 140 mg, still more preferably at least 160 mg, most preferably at least 180 mg and in particular at least 200 mg. Preferably, the monolith has a weight of from 100 to 1000 mg, more preferably 120 to 900 mg, still more preferably 140 to 800 mg, yet more preferably 150 to 700 mg, even more preferably 160 to 600 mg, most preferably 170 to 500 mg and in particular 200 to 400 mg. For the purpose of definition, a particle that is film-coated is also to be regarded as a particle according to the invention, i.e. the film-coating is not to be regarded as a separate entity but a constituent of the particle.

In another preferred embodiment, the pharmaceutical dosage form contains a multitude of particles containing pharmacologically active ingredient and physiologically acceptable polymer. In this regard, the pharmaceutical dosage form can be regarded as oligoparticulate or multiparticulate. For the purpose of the specification, the term "particulate", "oligoparticulate" or "multiparticulate" refers to a discrete mass of material, i.e. multitude of particles, which are solid, e.g. at 20° C. or at room temperature or ambient temperature. Preferably a particle is solid at 20° C.

In a preferred embodiment, the pharmaceutical dosage form is oligoparticulate. In this regard, oligoparticulate preferably means that all individual oligoparticles, i.e. particles containing pharmacologically active ingredient and physiologically acceptable polymer, each have a weight of 20 mg or more. According to this embodiment, all individual oligoparticles, i.e. particles containing pharmacologically active ingredient and physiologically acceptable polymer, each preferably have a weight of at least 30 mg, more preferably at least 40 mg, still more preferably at least 50 mg, most preferably at least 60 mg and in particular at least 100 mg. Preferably, all individual oligoparticles, i.e. particles containing pharmacologically active ingredient and physiologically acceptable polymer, each have a weight of from 20 to 1000 mg, more preferably 30 to 800 mg, still more preferably 40 to 600 mg, yet more preferably 50 to 400 mg, even more preferably 60 to 200 mg, most preferably 70 to 150 mg and in particular 80 to 120 mg.

Further, according to this embodiment, the pharmaceutical dosage form preferably comprises at most 10, more preferably at most 9, still more preferably at most 8, yet more preferably at most 7, even more preferably at most 6, most preferably at most 5, and in particular at most 4 or 3 or 2 particles containing pharmacologically active ingredient and physiologically acceptable polymer. When the particles containing pharmacologically active ingredient and physiologically acceptable polymer are oligoparticulate, the pharmaceutical dosage form may further comprise drug-free particles, which may each have an individual weight of less than 20 mg.

In another preferred embodiment, the pharmaceutical dosage form is multiparticulate. In this regard, multiparticulate preferably means that all individual multiparticles, i.e. particles containing pharmacologically active ingredient and physiologically acceptable polymer, each have a weight of less than 20 mg but at least 2 mg. According to this embodiment, all multiparticles, i.e. particles containing pharmacologically active ingredient and physiologically acceptable polymer, each preferably have a weight of less than 18 mg, more preferably less than 16 mg, still more preferably less than 14 mg, yet more preferably less than 12 mg, even more preferably less than 10 mg, most preferably less than 8 mg, and in particular less than 6 or 4 mg. Further, according to this embodiment, the pharmaceutical dosage form preferably comprises at least 2, more preferably at least 4, still more preferably at least 6, yet more preferably at least 8, even more preferably at least 10, most preferably at least 15 and in particular at least 20 or at least 100 or at least 1000 particles, i.e. particles containing pharmacologically active ingredient and physiologically acceptable polymer.

However, multiparticulate dosage forms are less preferred than dosage forms comprising a single particle containing pharmacologically active ingredient and physiologically acceptable polymer, and are less preferred than oligoparticulate dosage forms.

Preferably, the pharmaceutical dosage form according to the invention comprises n particles each containing pharmacologically active ingredient and physiologically acceptable polymer, wherein each of said n particles has a weight within the range of $(250\pm210)/n$ mg, more preferably $(250\pm180)/n$ mg, still more preferably $(250\pm150)/n$ mg, yet more preferably $(250\pm120)/n$ mg, even more preferably $(250\pm90)/n$ mg, most preferably $(250\pm60)/n$ mg, and in particular $(250\pm30)/n$ mg; wherein n is preferably 1, 2, 3, 4, 5, 6, 7, 8, 9 or 10.

In a preferred embodiment, the pharmaceutical dosage form according to the invention comprises a single particle containing pharmacologically active ingredient and physiologically acceptable polymer, wherein said single particle has a weight within the range of 250±210 mg, more preferably 250±180 mg, still more preferably 250±150 mg, yet more preferably 250±120 mg, even more preferably 250±90 mg, most preferably 250±60 mg, and in particular 250±30 mg. In another preferred embodiment, the pharmaceutical dosage form according to the invention comprises a single particle containing pharmacologically active ingredient and physiologically acceptable polymer, wherein said single particle has a weight within the range of 215±210 mg, more preferably 215±180 mg, still more preferably 215±150 mg, yet more preferably 215±120 mg, even more preferably 215±90 mg, most preferably 215±60 mg, and in particular 215±30 mg.

In still another preferred embodiment, the pharmaceutical dosage form according to the invention comprises two particles containing pharmacologically active ingredient and physiologically acceptable polymer, wherein each of said two particles has a weight within the range of 125±105 mg, more preferably 125±90 mg, still more preferably 125±75 mg, yet more preferably 125±60 mg, even more preferably 125±45 mg, most preferably 125±30 mg, and in particular 125±15 mg. In yet another preferred embodiment, the pharmaceutical dosage form according to the invention comprises two particles containing pharmacologically active ingredient and physiologically acceptable polymer, wherein each of said two particles has a weight within the range of 107.5±102 mg, more preferably 107.5±90 mg, still more preferably 107.5±75 mg, yet more preferably 107.5±60 mg, even more preferably 107.5±45 mg, most preferably 107.5±30 mg, and in particular 107.5±15 mg.

In still another preferred embodiment, the pharmaceutical dosage form according to the invention comprises three particles containing pharmacologically active ingredient and physiologically acceptable polymer, wherein each of said three particles has a weight within the range of 80±70 mg, more preferably 80±60 mg, still more preferably 80±50 mg, yet more preferably 80±40 mg, even more preferably 80±30 mg, most preferably 80±20 mg, and in particular 80±10 mg.

Preferably, the one or more particles containing pharmacologically active ingredient and physiologically acceptable polymer each have an extension in any given direction of at least 2.0 mm, more preferably at least 2.2 mm, still more preferably at least 2.5 mm, yet more preferably at least 2.8 mm, even more preferably at least 3.0 mm, most preferably at least 3.2 mm, and in particular at least 3.5 mm or 4.0 mm. According to this embodiment, the one or more particles containing pharmacologically active ingredient and physiologically acceptable polymer particularly preferably each have an extension in any given direction of at least 2.0 mm or 3.0 mm and have a weight of at least 20 mg.

Particularly preferably, the pharmaceutical dosage form contains a single particle containing pharmacologically active ingredient and physiologically acceptable polymer and having an extension in any direction of at least 2.0 mm; or a multitude of particles containing pharmacologically active ingredient and physiologically acceptable polymer each having an extension in any direction of at least 2.0 mm.

For the purpose of specification, "in any direction" preferably means in every direction in the three-dimensional space.

The size of the particles or the monolith may be determined by any conventional procedure known in the art, e.g. laser light scattering, sieve analysis, light microscopy or image analysis.

The shape of the one or more particles containing pharmacologically active ingredient and physiologically acceptable polymer is not particularly limited. Preferably, the one or more particles are of cylindrical shape. Preferably, the one or more particles are essentially cylindrical in shape, e.g. cut extruded rods (cut rods). Preferably, the one or more particles are melt-extruded. The diameter of such particles is therefore the diameter of their circular cross section. The cylindrical shape can be caused by hot-melt extrusion according to which the diameter of the circular cross section is a function of the extrusion die and the length of the cylinders is a function of the cutting length according to which the extruded strand of material is cut into pieces of preferably more or less predetermined length. Thus, preferably the one or more particles are crude cut rods obtained by cutting a hot-melt extruded strand of a pharmaceutical composition comprising the pharmacologically active ingredient and the physiologically acceptable polymer. In this regard "crude" preferably means that after cutting, the cut rods are not subjected to further processing steps such as forming or shaping.

Preferably, the one or more particles containing pharmacologically active ingredient and physiologically acceptable polymer are "formed". In this regard, the term "formed" refers to any measure providing the material of particle with a predetermined or arbitrary outer shape. Forming may but does not need to be achieved by means of a die. Preferably, the one or more particles are thermoformed. For example, extruding a heated material, e.g. by means of hot-melt extrusion, and subsequently cutting the extruded strand into particles of predetermined length provides particles containing pharmacologically active ingredient and physiologically acceptable polymer according to the invention.

Each of the one or more particles containing pharmacologically active ingredient and physiologically acceptable polymer may comprise a film-coating.

In a preferred embodiment, the one or more particles containing pharmacologically active ingredient and physiologically acceptable polymer are film coated. The one or more particles can optionally be provided, partially or completely, with a conventional coating. The one or more particles are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinyl alcohol-polyethylene glycol graft copolymers, polyvinylacetate; and natural film formers.

The coating material may contain excipients such as stabilizers (e.g. surfactants such as macrogol cetostearylether, sodium dodecylsulfate, and the like). Suitable excipients of film coating materials are known to the skilled person. In a particularly preferred embodiment, the coating is water-soluble.

Though less preferred, the coating can principally be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. A particularly preferred coating contains polyvinyl alcohol and optionally, further excipients such as xanthan gum and/or talcum.

When the one or more particles containing pharmacologically active ingredient and physiologically acceptable polymer are film coated, the film coating is to be regarded as a constituent of the particles, i.e. contributes to their weight and volume.

In another preferred embodiment, however, the one or more particles containing pharmacologically active ingredient and physiologically acceptable polymer are not film coated.

It has been surprisingly found that tamper-resistant pharmaceutical dosage forms can be provided, which do not require film-coating of a thermoformed intermediate and thus, are easier to manufacture. The crude intermediate that is obtained e.g. by thermoforming can be incorporated in the pharmaceutical dosage form as such. Subsequent process steps following thermoforming can be omitted, particularly film coating.

Further, it has been surprisingly found that the advantages conventionally achieved by film-coating can alternatively be achieved, e.g. by placing the thermoformed intermediates in capsules. Under these circumstances, the full range of approved dyes is available and no discoloration mechanisms are observed.

The pharmaceutical dosage form comprises one or more particles each containing a pharmacologically active ingredient.

For the purpose of specification, the term "pharmacologically active ingredient" as used herein may refer to either one or more pharmacologically active ingredients, i.e. the term may refer to a single pharmacologically active ingredient or a combination of one or more pharmacologically active ingredients.

There are generally no limitations as to the pharmacologically active ingredient (active pharmaceutical ingredient, API) which can be incorporated in the one or more particles of the pharmaceutical dosage form according to the invention. Furthermore, the term "pharmacologically active ingredient" preferably includes any physiologically acceptable salt, e.g. physiologically acceptable acid addition salt, of the base form of the pharmacologically active ingredient. Physiologically acceptable acid addition salts comprise any acid addition salts which can conveniently be obtained by treating the base form of a pharmacologically active ingredient with appropriate organic and inorganic acids. Pharmacologically active ingredients containing an acidic proton may be converted into their non-toxic metal or amine addition salt forms by treatment with appropriate organic and inorganic bases. The term addition salt also comprises the hydrates and solvent addition forms which a pharmacologically active ingredient is able to form. Examples of such forms are e.g. hydrates, alcoholates and the like.

Unless explicitly stated otherwise, all amounts of the pharmacologically active ingredient specified in the following are given according to the corresponding amount of the free compound.

Preferably, the pharmacologically active ingredient is an opioid.

Preferably, at least 99 wt.-%, more preferably at least 99.9 wt.-%, most preferably at least 99.99 wt.-% and in particular at least 99.999 wt.-% of the total amount of the pharmacologically active ingredient contained in the pharmaceutical dosage form are contained in the one or more particles.

The term "prolonged release" is known to the skilled artisan. For the purpose of specification, the term "prolonged release" preferably refers to a release rate of the pharmacologically active ingredient from the formulation that has been reduced over time in order to maintain therapeutic activity, to reduce toxic effects, or for some other therapeutic purpose such as reducing the dosing frequency.

The term "immediate release" is known to the skilled artisan. For the purpose of specification, the term "immediate release" preferably refers to a release rate of the pharmacologically active ingredient from the formulation that is comparatively fast and not retarded.

Preferably, the one or more particles form a discontinuous phase that is embedded in a matrix material.

Preferably, the pharmaceutical dosage form according to the invention comprises the one or more particles containing pharmacologically active ingredient and physiologically acceptable polymer as a discontinuous phase, i.e. the one or more particles form a discontinuous phase in an outer matrix material which in turn preferably forms a continuous phase. In this regard, discontinuous means that not each and every particle is in intimate contact with another particle but that the particles are at least partially separated from one another by the outer matrix material in which the particles are embedded. In other words, the particles preferably do not form a single coherent mass within the pharmaceutical dosage forms according to the invention (multicomponent tablet).

In a preferred embodiment, further excipient(s) form(s) an outer matrix material in which the one or more particles is/are embedded. According to this embodiment, the pharmaceutical dosage form according to the invention can preferably be a MUPS formulation (multiple unit pellet system) or a capsule.

Preferably, the one or more particles and the further excipient(s) have different morphology and properties. Preferably, the one or more particles containing pharmacologically active ingredient and physiologically acceptable polymer form a discontinuous phase within the outer matrix material formed by the further excipient(s) (multicomponent tablet). When the one or more particles contain a prolonged release matrix material, the outer matrix material is to be distinguished from said prolonged release matrix material, since the outer matrix material preferably does not provide for a prolonged release.

The one or more particles containing pharmacologically active ingredient and physiologically acceptable polymer typically have mechanical properties that differ from the mechanical properties of the outer matrix material. Preferably, the one or more particles containing pharmacologically active ingredient and physiologically acceptable polymer have a higher mechanical strength than the outer matrix material. The one or more particles can preferably be visualized by conventional means such as solid state nuclear magnetic resonance spectroscopy, scanning electron microscopy, terahertz spectroscopy and the like.

In a further preferred embodiment, the one or more particles containing pharmacologically active ingredient and physiologically acceptable polymer constitute a spatially confined area within the pharmaceutical dosage form. According to this embodiment, the one or more particles preferably form a layer, a coating, a core or a mantle of the pharmaceutical dosage form.

When the one or more particles containing pharmacologically active ingredient and physiologically acceptable polymer and/or the further excipient(s) form a layer, the pharmaceutical dosage form preferably is in form of a layered tablet.

The one or more particles containing pharmacologically active ingredient and physiologically acceptable polymer or the further excipient(s) may also form the coating of the pharmaceutical dosage form. Preferably, the one or more particles form the core of the pharmaceutical dosage form that is coated by the further excipient(s). Preferably, however, neither the one or more particles nor the further excipient(s) forms a coating of the pharmaceutical dosage form, particularly no spray coating. Rather, the one or more particles and the further excipient(s) are preferably both coated by another material such as a sugar coating.

In a preferred embodiment, the pharmaceutical dosage form is in form of a mantle tablet. According to this embodiment, the one or more particles containing pharmacologically active ingredient and physiologically acceptable polymer preferably form the core and the further excipient(s) preferably forms the mantle.

In a preferred embodiment, the pharmaceutical dosage form according to the invention is a tablet, which comprises
(i) a single particle containing pharmacologically active ingredient and physiologically acceptable polymer and further excipient(s) that are arranged to form a bilayer tablet;
(ii) a single particle containing pharmacologically active ingredient and physiologically acceptable polymer and forming a core that is surrounded by further excipient(s) such that the single particle and the further excipient(s) are arranged to form a mantle tablet;
(iii) a single particle containing pharmacologically active ingredient and physiologically acceptable polymer and further excipient(s) that are arranged to form a trilayer tablet, wherein the single particle forms the middle layer and the further excipient(s) form the outer layers;
(iv) a plurality of particles containing pharmacologically active ingredient and physiologically acceptable polymer and further excipient(s) that are arranged to form a multilayer tablet, wherein preferably each of the particles containing pharmacologically active ingredient and physiologically acceptable polymer is arranged in between two adjacent layers of further excipient(s);
(v) a plurality of particles containing pharmacologically active ingredient and physiologically acceptable polymer which form a discontinuous phase embedded in further excipient(s) which form a matrix; or
(vi) one or more particles containing pharmacologically active ingredient and physiologically acceptable polymer and further excipient(s) are together coated by a sugar coating thus forming a sugar-coated tablet (dragée).

In another preferred embodiment, the pharmaceutical dosage form according to the invention is a capsule, which is filled with
(i) a single particle containing pharmacologically active ingredient and physiologically acceptable polymer but no further excipient(s) and preferably no further pharmacologically active ingredient, wherein preferably the total amount of the pharmacologically active ingredient that is contained in the pharmaceutical dosage form is contained in the single particle;
(ii) a single particle containing pharmacologically active ingredient and physiologically acceptable polymer and further excipient(s);
(iii) a plurality of particles containing pharmacologically active ingredient and physiologically acceptable polymer but no further excipient(s) and preferably no further pharmacologically active ingredient, wherein preferably the total amount of the pharmacologically active ingredient that is contained in the pharmaceutical dosage form is contained in the plurality of particles; or
(iv) a plurality of particles containing pharmacologically active ingredient and physiologically acceptable polymer and further excipient(s).

The pharmaceutical dosage form comprises one or more particles containing a pharmacologically active ingredient, and preferably providing prolonged release thereof.

In a preferred embodiment, the pharmacologically active ingredient is only a single pharmacologically active ingredient. In another preferred embodiment, the pharmacologically active ingredient is a combination of two or more pharmacologically active ingredients.

Preferably, the pharmacologically active ingredient has potential for being abused. Pharmacologically active ingredients with potential for being abused are known to the person skilled in the art and comprise e.g. tranquillizers, stimulants, barbiturates, narcotics, opioids or opioid derivatives.

Preferably, the pharmacologically active ingredient has a psychotropic effect, i.e. crosses the blood-brain barrier and acts primarily upon the central nervous system where it affects brain function, resulting in alterations in perception, mood, consciousness, cognition, and behavior.

Preferably, the pharmacologically active ingredient is selected from the group consisting of opioids, stimulants, tranquilizers, and other narcotics. Particularly preferably, the pharmacologically active ingredient is an opioid.

Particularly preferably, the pharmacologically active ingredient is an opioid or a physiological acceptable salt thereof. According to the Anatomical Therapeutic Chemical (ATC) classification system by WHO (ATC index), opioids are divided into natural opium alkaloids, phenylpiperidine derivatives, diphenylpropylamine derivatives, benzomorphan derivatives, oripavine derivatives, morphinan derivatives and others. Preferably, the pharmacologically active ingredient is selected from ATC classes [M01A], [M01C], [N02B] and [N02C] according to the WHO.

The following opioids, tranquilizers or other narcotics are substances with a psychotropic action, i.e. have a potential of abuse, and hence are preferably contained in the one or more particles of the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, Papaver somniferum, papavereturn, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl) propionamide, (1R,2R)-3-(3-dimethylamino-1-ethyl-2-methyl-propyl)phenol, (1R,2R,4S)-2-(dimethylamino) methyl-4-(p-fluorobenzyloxy)-1-(m-methoxyphenyl) cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl) propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR-SS)-2-acetoxy-4-trifluoromethyl-benzoic acid 3-(2-dimethylaminomethyl-1-hydroxycyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxybenzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxycyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxybiphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the one or more particles contain an opioid selected from the group consisting of DPI-125, M6G (CE-04-410), ADL-5859, CR-665, NRP290 and sebacoyl dinalbuphine ester.

In a preferred embodiment, the one or more particles contain the pharmacologically active ingredient which is one pharmacologically active ingredient or more pharmacologically active ingredients selected from the group consisting of oxycodone, oxymorphone, hydromorphone, hydrocodone, morphine, tapentadol, tramadol, buprenorphine, and the physiologically acceptable salts thereof.

In another preferred embodiment, the pharmacologically active ingredient is selected from the group consisting of tapentadol, faxeladol, axomadol and the physiologically acceptable salts thereof.

In still another preferred embodiment, the pharmacologically active ingredient is selected from the group consisting of 1,1-(3-dimethylamino-3-phenylpentamethylene)-6-fluoro-1,3,4,9-tetrahydropyrano[3,4-b]indole (cebranopadol), particularly its hemicitrate; 1,1-[3-dimethylamino-3-(2-thienyl)pentamethylene]-1,3,4,9-tetrahydropyrano[3,4-b] indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

Preferably, the content of the pharmacologically active ingredient is at least 0.1 wt.-%, more preferably at least 0.5 wt.-%, still more preferably at least 1.0 wt.-%, yet more preferably at least 1.5 wt.-%, most preferably at least 1.8 wt.-%, and in particular at least 2.0 wt.-%, based on the total weight of a particle.

In another preferred embodiment, the content of the pharmacologically active ingredient is at least 1.0 wt.-%, more preferably at least 2.0 wt.-%, still more preferably at least 3.0 wt.-%, yet more preferably at least 4.0 wt.-%, even more preferably at least 5.0 wt.-%, most preferably at least 6.0 wt.-%, and in particular at least 7.0 wt.-%, based on the total weight of a particle.

The pharmacologically active ingredient is present in the pharmaceutical dosage form in a therapeutically effective amount. In general, the amount that constitutes a therapeutically effective amount varies according to the pharmacologically active ingredients being used, the condition being treated, the severity of said condition, the patient being treated, and whether the pharmaceutical dosage form or the particle in which the pharmacologically active ingredient is contained is designed for an immediate or retarded release.

The content of the pharmacologically active ingredient preferably ranges from about 0.01 wt.-% to about 95 wt.-%, more preferably from about 0.1 wt.-% to about 80 wt.-%, even more preferably from about 0.2 wt.-% or about 1.0 wt.-% to about 50 wt.-%, yet more preferably from about 0.2 wt.-% or about 1.5 wt.-% to about 30 wt.-%, and most preferably from about 0.2 wt.-% or about 2.0 wt.-% to 20 wt.-%, based on the total weight of the one or more particles or based on the total weight of the pharmaceutical dosage form.

Preferably, the content of the pharmacologically active ingredient is within the range of from 0.01 to 80 wt.-%, more preferably 0.1 to 50 wt.-%, still more preferably 0.5 to 25 wt.-% or 1 to 25 wt.-%, based on the total weight of the pharmaceutical dosage form. In a preferred embodiment, the content of the pharmacologically active ingredient is within the range of from 1.5±1 wt.-% or 3±2 wt.-%, more preferably 1.5±0.9 wt.-% or 3±1.5 wt.-%. In another preferred embodiment, the content of the pharmacologically active ingredient is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In still another preferred embodiment, the content of the pharmacologically active ingredient is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of the pharmacologically active ingredient is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form.

Preferably, the content of the pharmacologically active ingredient is within the range of from 0.01 to 80 wt.-%, more preferably 0.1 to 60 wt.-%, still more preferably 1 to 50 wt.-% or 5 to 50 wt.-%, based on the total weight of the one or more particles. In a preferred embodiment, the content of the pharmacologically active ingredient is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 1.5±1 wt.-%, 3±2 wt.-%, 5±2 wt.-%, 7±2 wt.-% or 9±2 wt.-%, based on the total weight of the one or more particles. In another preferred embodiment, the content of the pharmacologically active ingredient is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the one or more particles. In a further preferred embodiment, the content of the pharmacologically active ingredient is within the range of from 20±6 wt.-%, 25±6 wt.-% or 30±6 wt.-%, more preferably 20±5 wt.-%, 25±5 wt.-% or 30±5 wt.-%, still more preferably 20±4 wt.-%, 25±4 wt.-% or 30±4 wt.-%, most preferably 20±3 wt.-%, 25±3 wt.-% or 30±3 wt.-% and in particular 20±2 wt.-%, 25±2 wt.-% or 30±2 wt.-%, based on the total weight of the one or more particles.

The total dose of the pharmacologically active ingredient in the one or more particles and the pharmaceutical dosage form, respectively, is not limited. The dose of the pharmacologically active ingredient which is adapted for administration preferably is in the range of 0.01 mg to 2,000 mg or 0.01 mg to 1,000 mg or 0.1 mg to 500 mg, more preferably in the range of 1.0 mg to 400 mg, even more preferably in the range of 1.0 mg to 10.0 mg or 5.0 mg to 300 mg, and most preferably in the range of 1.5 mg to 8 mg or 10 mg to 250 mg. In a preferred embodiment, the total amount of the pharmacologically active ingredient which is contained in the one or more particles and the pharmaceutical dosage form, respectively, is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg. In another preferred embodiment, the total amount of the pharmacologically active ingredient which is contained in the one or more particles and the pharmaceutical dosage form, respectively, is within the range of from 10 to 500 mg, more preferably 12 to 450 mg, still more preferably 14 to 400 mg, yet more preferably 16 to 350 mg, most preferably 18 to 325 mg and in particular 20 to 300 mg.

In a preferred embodiment, the pharmacologically active ingredient is contained in the one or more particles and the pharmaceutical dosage form, respectively, in a total amount of 10±5 µg, 20±5 µg, 30±5 µg, 40±5 µg, 50±5 µg, 60±5 µg, 70±5 µg, 80±5 µg, 90±5 µg, 100±5 µg, 125±25 µg, 150±25 µg, 175±25 µg, 200±25 µg, 250±50 µg, 300±50 µg, 350±50 µg, 400±50 µg, 450±50 µg, 500±50 µg, 550±50 µg, 600±50 µg, 650±50 µg, 700±50 µg, 750±50 µg, 800±50 µg, 850±50 µg, 900±50 µg, 950±50 µg, or 1000±50 µg. In another preferred embodiment, the pharmacologically active ingredient is contained in the one or more particles and the pharmaceutical dosage form, respectively, in a total amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, or 250±5 mg. In another preferred embodiment, the pharmacologically active ingredient is contained in the one or more particles and the pharmaceutical dosage form, respectively, in a total amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, or 250±2.5 mg. In still another preferred embodiment, the pharmacologically active ingredient is contained in the one or more particles and the pharmaceutical dosage form, respectively, in a total amount of 250±10 mg, 275±10 mg, 300±10 mg, 325±10 mg, 350±10 mg, 375±10 mg, 400±10 mg, 425±10 mg, 450±10 mg, 475±10 mg, 500±10 mg, 525±10 mg, 550±10 mg, 575±10 mg or 600±10 mg.

In a particularly preferred embodiment, the pharmacologically active ingredient is oxycodone, preferably its HCl salt, and the pharmaceutical dosage form is adapted for administration twice daily. In this embodiment, the pharmacologically active ingredient is preferably contained in the one or more particles and the pharmaceutical dosage form, respectively, in a total amount of from 1 to 80 mg. In another particularly preferred embodiment, the pharmacologically active ingredient is oxycodone, preferably its HCl salt, and the pharmaceutical dosage form is adapted for administration once daily. In this embodiment, the pharmacologically active ingredient is preferably contained in the one or more particles and the pharmaceutical dosage form, respectively, in a total amount of from 2 to 320 mg.

In another particularly preferred embodiment, the pharmacologically active ingredient is oxymorphone, preferably its HCl salt, and the pharmaceutical dosage form is adapted for administration twice daily. In this embodiment, the pharmacologically active ingredient is preferably contained in the one or more particles and the pharmaceutical dosage form, respectively, in a total amount of from 5 to 40 mg. In another particularly preferred embodiment, the pharmacologically active ingredient is oxymorphone, preferably its HCl salt, and the pharmaceutical dosage form is adapted for administration once daily. In this embodiment, the pharmacologically active ingredient is preferably contained in the one or more particles and the pharmaceutical dosage form, respectively, in a total amount of from 10 to 80 mg.

In another particularly preferred embodiment, the pharmacologically active ingredient is tapentadol, preferably its HCl salt, and the pharmaceutical dosage form is adapted for administration once daily or twice daily. In this embodiment, the pharmacologically active ingredient is preferably contained in the one or more particles and the pharmaceutical dosage form, respectively, in a total amount of from 25 to 250 mg.

In still another particularly preferred embodiment, the pharmacologically active ingredient is hydromorphone, preferably its HCl salt, and the pharmaceutical dosage form is adapted for administration twice daily. In this embodiment, the pharmacologically active ingredient is preferably contained in the one or more particles and the pharmaceutical dosage form, respectively, in a total amount of from 2 to 52 mg. In another particularly preferred embodiment, the pharmacologically active ingredient is hydromorphone, preferably its HCl salt, and the pharmaceutical dosage form is adapted for administration once daily. In this embodiment, the pharmacologically active ingredient is preferably contained in the one or more particles and the pharmaceutical dosage form, respectively, in a total amount of from 4 to 104 mg.

In yet another particularly preferred embodiment, the pharmacologically active ingredient is tramadol, preferably its HCl salt, and the pharmaceutical dosage form is adapted for administration twice daily. In this embodiment, the pharmacologically active ingredient is preferably contained in the one or more particles and the pharmaceutical dosage form, respectively, in a total amount of from 5 to 300 mg. In another particularly preferred embodiment, the pharmacologically active ingredient is tramadol, preferably its HCl salt, and the pharmaceutical dosage form is adapted for administration once daily. In this embodiment, the pharmacologically active ingredient is preferably contained in the one or more particles and the pharmaceutical dosage form, respectively, in a total amount of from 10 to 500 mg.

In another particularly preferred embodiment, the pharmacologically active ingredient is hydrocodone, preferably its HCl salt, and the pharmaceutical dosage form is adapted for administration twice daily. In this embodiment, the pharmacologically active ingredient is preferably contained in the one or more particles and the pharmaceutical dosage form, respectively, in a total amount of from 5 to 250 mg. In another particularly preferred embodiment, the pharmacologically active ingredient is hydrocodone, preferably its HCl salt, and the pharmaceutical dosage form is adapted for administration once daily. In this embodiment, the pharmacologically active ingredient is preferably contained in the one or more particles and the pharmaceutical dosage form, respectively, in a total amount of from 5 to 250 mg.

In still another particularly preferred embodiment, the pharmacologically active ingredient is morphine, preferably its HCl or $H_2SO_4$ salt, and the pharmaceutical dosage form is adapted for administration twice daily. In this embodiment, the pharmacologically active ingredient is preferably contained in the one or more particles and the pharmaceutical dosage form, respectively, in a total amount of from 5 to 250 mg. In another particularly preferred embodiment, the pharmacologically active ingredient is morphine, preferably its HCl or $H_2SO_4$ salt, and the pharmaceutical dosage form is adapted for administration once daily. In this embodiment, the pharmacologically active ingredient is preferably contained in the one or more particles and the pharmaceutical dosage form, respectively, in a total amount of from 5 to 250 mg.

In another particularly preferred embodiment, the pharmacologically active ingredient is buprenorphine, preferably its HCl salt, and the pharmaceutical dosage form is adapted for administration twice daily. In this embodiment, the pharmacologically active ingredient is preferably contained in the one or more particles and the pharmaceutical dosage form, respectively, in a total amount of from 1 to 12 mg. In another particularly preferred embodiment, the pharmacologically active ingredient is buprenorphine, preferably its HCl salt, and the pharmaceutical dosage form is adapted for administration once daily. In this embodiment, the pharmacologically active ingredient is preferably contained in the one or more particles and the pharmaceutical dosage form, respectively, in a total amount of from 2 to 12 mg.

The pharmacologically active ingredient that is employed in the preparation of the one or more particles preferably has an average particle size of less than 500 microns, still more preferably less than 300 microns, yet more preferably less than 200 or 100 microns. There is no lower limit on the average particle size and it may be, for example, 50 microns. The particle size of pharmacologically active ingredients may be determined by any technique conventional in the art, e.g. laser light scattering, sieve analysis, light microscopy or image analysis.

The tamper-resistant pharmaceutical dosage form according to the invention comprises one or more particles each containing a physiologically acceptable polymer.

Preferably, the one or more particles provide prolonged release of the pharmacologically active ingredient. While such prolonged release may principally be achieved by providing the one or more particles with a prolonged release coating containing pore formers, prolonged release is preferably achieved by a prolonged release matrix.

Thus, the one or more particles preferably comprise a prolonged release matrix. The prolonged release matrix in turn preferably comprises a prolonged release matrix material that serves the function of providing prolonged release of the pharmacologically active ingredient, optionally further pharmaceutical excipients that do not substantially influence the release profile, and the pharmacologically active ingredient.

The pharmacologically active ingredient is preferably embedded, particularly preferably dispersed in the prolonged release matrix material. Preferably, the pharmacologically active ingredient is embedded in a matrix material comprising the physiologically acceptable polymer.

The total content of the prolonged release matrix (pharmacologically active ingredient+prolonged release matrix material+optionally present excipients that do not substantially influence the release profile) that is contained in the one or more particles is preferably at least 30 wt.-%, more preferably at least 40 wt.-%, still more preferably at least 50 wt.-%, yet more preferably at least 60 wt.-%, even more preferably at least 70 wt.-%, most preferably at least 80 wt.-%, and in particular at least 90 wt.-%, relative to the total weight of the one or more particles.

The total content of the prolonged release matrix (pharmacologically active ingredient+prolonged release matrix material+optionally present excipients that do not substantially influence the release profile) that is contained in the one or more particles is preferably within the range of from 5 to 95 wt.-%, more preferably 7 to 90 wt.-%, still more preferably 9 to 80 wt.-%, yet more preferably 11 to 70 wt.-%, even more preferably 13 to 60 wt.-%, most preferably 14 to 50 wt.-%, and in particular 15 to 40 wt.-%, relative to the total weight of the pharmaceutical dosage form.

Preferably, the pharmacologically active ingredient and the prolonged release matrix material are intimately homogeneously distributed within the one or more particles so that the one or more particles do(es) not contain any portions where either the pharmacologically active ingredient is present in the absence of prolonged release matrix material or where prolonged release matrix material is present in the absence of the pharmacologically active ingredient.

When the one or more particles are film coated, the prolonged release matrix material is preferably homogeneously distributed in the body of the one or more particles, i.e. the film coating preferably does not contain prolonged release matrix material.

Apart from the prolonged release matrix material, the one or more particles preferably contain conventional pharmaceutical excipients that do not substantially influence the release profile.

Preferably, the total content of the prolonged release matrix material, i.e. material that serves the function of providing prolonged release of the pharmacologically active ingredient, is within the range of from 20 to 99 wt.-%, relative to the total weight of the one or more particles. When the particles containing pharmacologically active ingredient and physiologically acceptable polymer are particulate, these percent values preferably are related to the total weight of all particles of the one or more particles.

In a preferred embodiment, the content of the prolonged release matrix material is at least 5 wt.-%, or at least 10 wt.-%, or at least 15 wt.-%, more preferably at least 20 wt.-%, or at least 25 wt.-%, or at least 30 wt.-%, still more preferably at least 35 wt.-%, or at least 40 wt.-%, or at least 45 wt.-%, yet more preferably at least 50 wt.-%, or at least 55 wt.-%, or at least 60 wt.-%, most preferably at least 65 wt.-%, or at least 70 wt.-%, or at least 75 wt.-%, and in particular at least 80 wt.-%, or at least 85 wt.-%, or at least 90 wt.-%, based on the total weight of the one or more particles.

In a preferred embodiment, the total content of prolonged release matrix material is within the range of 25±20 wt.-%, more preferably 25±15 wt.-%, most preferably 25±10 wt.-%, and in particular 25±5 wt.-%, based on the total weight of the one or more particles.

In another preferred embodiment, the total content of prolonged release matrix material is within the range of 30±20 wt.-%, more preferably 30±15 wt.-%, most preferably 30±10 wt.-%, and in particular 30±5 wt.-%, based on the total weight of the one or more particles.

In still another preferred embodiment, the total content of prolonged release matrix material is within the range of 35±20 wt.-%, more preferably 35±15 wt.-%, most preferably 35±10 wt.-%, and in particular 35±5 wt.-%, based on the total weight of the one or more particles.

In a yet another preferred embodiment, the total content of prolonged release matrix material is within the range of 40±20 wt.-%, more preferably 40±15 wt.-%, and most preferably 40±10 wt.-%, and in particular 40±5 wt.-%, based on the total weight of the one or more particles.

In a further preferred embodiment, the total content of prolonged release matrix material is within the range of 45±20 wt.-%, more preferably 45±15 wt.-%, and most preferably 45±10 wt.-%, and in particular 45±5 wt.-%, based on the total weight of the one or more particles.

In still a further preferred embodiment, the total content of prolonged release matrix material is within the range of 50±20 wt.-%, more preferably 50±15 wt.-%, and most preferably 50±10 wt.-%, and in particular 50±5 wt.-%, based on the total weight of the one or more particles.

In yet a further preferred embodiment, the total content of prolonged release matrix material is within the range of 55±20 wt.-%, more preferably 55±15 wt.-%, and most preferably 55±10 wt.-%, and in particular 55±5 wt.-%, based on the total weight of the one or more particles.

In another preferred embodiment, the total content of prolonged release matrix material is within the range of 60±20 wt.-%, more preferably 60±15 wt.-%, and most preferably 60±10 wt.-%, and in particular 60±5 wt.-%, based on the total weight of the one or more particles.

In still another preferred embodiment, the total content of prolonged release matrix is within the range of 65±20 wt.-%, more preferably 65±15 wt.-%, and most preferably 65±10 wt.-%, and in particular 65±5 wt.-%, based on the total weight of the one or more particles.

In yet another preferred embodiment, the total content of prolonged release matrix material is within the range of 70±20 wt.-%, more preferably 70±15 wt.-%, and most preferably 70±10 wt.-%, and in particular 70±5 wt.-%, based on the total weight of the one or more particles.

In a further preferred embodiment, the total content of prolonged release matrix material is within the range of 75±20 wt.-%, more preferably 75±15 wt.-%, and most preferably 75±10 wt.-%, and in particular 75±5 wt.-%, based on the total weight of the one or more particles.

In still a further preferred embodiment, the total content of prolonged release matrix material is within the range of 80±15 wt.-%, more preferably 80±12 wt.-%, and most preferably 80±10 wt.-%, and in particular 80±5 wt.-%, based on the total weight of the one or more particles.

In yet a further preferred embodiment, the total content of prolonged release matrix material is within the range of 85±10 wt.-%, more preferably 85±8 wt.-%, and most preferably 85±6 wt.-%, and in particular 85±4 wt.-%, based on the total weight of the one or more particles.

In another preferred embodiment, the total content of prolonged release matrix material is within the range of 90±8 wt.-%, more preferably 90±7 wt.-%, and most preferably 90±6 wt.-%, and in particular 90±4 wt.-%, based on the total weight of the one or more particles.

In still another preferred embodiment, the total content of prolonged release matrix material is within the range of 95±3 wt.-%, more preferably 95±2 wt.-%, and most preferably 95±1 wt.-%, and in particular 95±0.5 wt.-%, based on the total weight of the one or more particles.

Preferably, the total content of the prolonged release matrix material, i.e. material that serves the function of providing prolonged release of the pharmacologically active ingredient, contained in the one or more particles is within the range of from 5 to 95 wt.-%, more preferably 15 to 80 wt.-% or 20 to 80 wt.-% relative to the total weight of the pharmaceutical dosage form.

In a preferred embodiment, the content of the prolonged release matrix material is at least 5 wt.-% or at least 10 wt.-%, more preferably at least 15 wt.-%, still more preferably at least 20 wt.-%, yet more preferably at least 25 wt.-% and in particular at least 30 wt.-%, or at least 35 wt.-%, or at least 40 wt.-%, or at least 45 wt.-%, or at least 50 wt.-%, or at least 55 wt.-%, or at least 60 wt.-%, based on the total weight of the pharmaceutical dosage form.

In still another preferred embodiment, the total content of prolonged release matrix material is within the range of 20±16 wt.-%, more preferably 20±12 wt.-%, most preferably 20±8 wt.-%, and in particular 20±4 wt.-%, based on the total weight of the pharmaceutical dosage form.

In yet another preferred embodiment, the total content of prolonged release matrix material is within the range of 25±20 wt.-%, more preferably 25±15 wt.-%, most preferably 25±10 wt.-%, and in particular 25±5 wt.-%, based on the total weight of the pharmaceutical dosage form.

In a further preferred embodiment, the total content of prolonged release matrix material is within the range of 30±20 wt.-%, more preferably 30±15 wt.-%, most preferably 30±10 wt.-%, and in particular 30±5 wt.-%, based on the total weight of the pharmaceutical dosage form.

In still a further preferred embodiment, the total content of prolonged release matrix material is within the range of 35±20 wt.-%, more preferably 35±15 wt.-%, most preferably 35±10 wt.-%, and in particular 35±5 wt.-%, based on the total weight of the pharmaceutical dosage form.

In a still further preferred embodiment, the total content of prolonged release matrix material is within the range of 40±20 wt.-%, more preferably 40±15 wt.-%, and most preferably 40±10 wt.-%, and in particular 40±5 wt.-%, based on the total weight of the pharmaceutical dosage form.

In a yet further preferred embodiment, the total content of prolonged release matrix material is within the range of 45±20 wt.-%, more preferably 45±15 wt.-%, and most preferably 45±10 wt.-%, and in particular 45±5 wt.-%, based on the total weight of the pharmaceutical dosage form.

In another preferred embodiment, the total content of prolonged release matrix material is within the range of 50±20 wt.-%, more preferably 50±15 wt.-%, and most preferably 50±10 wt.-%, and in particular 50±5 wt.-%, based on the total weight of the pharmaceutical dosage form.

In a yet further preferred embodiment, the total content of prolonged release matrix material is within the range of 55±20 wt.-%, more preferably 55±15 wt.-%, and most preferably 55±10 wt.-%, and in particular 55±5 wt.-%, based on the total weight of the pharmaceutical dosage form.

In another preferred embodiment, the total content of prolonged release matrix material is within the range of 60±20 wt.-%, more preferably 60±15 wt.-%, and most preferably 60±10 wt.-%, and in particular 60±5 wt.-%, based on the total weight of the pharmaceutical dosage form.

In still another preferred embodiment, the total content of prolonged release matrix material is within the range of 65±20 wt.-%, more preferably 65±15 wt.-%, and most preferably 65±10 wt.-%, and in particular 65±5 wt.-%, based on the total weight of the pharmaceutical dosage form.

Preferably, the relative weight ratio of the prolonged release matrix material, i.e. material that serves the function of providing prolonged release of the pharmacologically active ingredient, to the pharmacologically active ingredient is within the range of from 40:1 to 1:40 or 35:1 to 1:35 or 30:1 to 1:30 or 20:1 to 1:20, more preferably 15:1 to 1:15, still more preferably 10:1 to 1:10, yet more preferably 7:1 to 1:7, most preferably 5:1 to 1:5, and in particular 2:1 to 1:2.

The prolonged release matrix material, i.e. material that serves the function of providing prolonged release of the pharmacologically active ingredient, preferably comprises at least one physiologically acceptable polymer and/or optionally a waxy material. Preferably, the prolonged release matrix material comprises only one physiologically acceptable polymer. In a preferred embodiment, the prolonged release matrix material consists of the physiologically acceptable polymer.

In a preferred embodiment, the pharmacologically active ingredient is embedded in a prolonged release matrix comprising the physiologically acceptable polymer.

The total content of the physiologically acceptable polymer is preferably at least 65 wt.-%, more preferably at least 70 wt.-%, still more preferably at least 75 wt.-%, yet more preferably at least 80 wt.-%, even more preferably at least 85 wt.-%, most preferably at least 90 wt.-%, and in particular at least 95 wt.-%, relative to the total weight of the prolonged release matrix material, i.e. material that serves the function of providing prolonged release of the pharmacologically active ingredient.

The total content of the physiologically acceptable polymer is preferably at least 20 wt.-%, more preferably at least 30 wt.-%, still more preferably at least 40 wt.-%, yet more preferably at least 50 wt.-%, even more preferably at least 60 wt.-%, most preferably at least 65 wt.-% or at least 70 wt.-%, and in particular at least 70 wt.-% or at least 80 wt.-%, relative to the total weight of the prolonged release matrix (pharmacologically active ingredient+prolonged release matrix material+optionally present excipients that do not substantially influence the release profile).

Preferably, the content of the physiologically acceptable polymer is at least 25 wt.-%, based on the total weight of a particle.

Preferably, the total content of the physiologically acceptable polymer is at least 20 wt.-%, more preferably at least 30 wt.-%, still more preferably at least 40 wt.-%, yet more preferably at least 50 wt.-%, even more preferably at least 60 wt.-%, most preferably at least 65 wt.-% or at least 70 wt.-%, and in particular at least 70 wt.-% or at least 80 wt.-%, relative to the total weight of the one or more particles.

In a preferred embodiment, the total content of the physiologically acceptable polymer is at least 5 wt.-%, more preferably at least 10 wt.-%, still more preferably at least 15 wt.-%, yet more preferably at least 20 wt.-% and in particular at least 25 wt.-%, relative to the total weight of the one or more particles. In a particularly preferred embodiment, the content of the physiologically acceptable polymer is at least 30 wt.-% relative to the total weight of the one or more particles.

In a preferred embodiment, the total content of the physiologically acceptable polymer is within the range of 10±8 wt.-%, more preferably 10±6 wt.-%, most preferably 10±4 wt.-%, and in particular 10±2 wt.-%, based on the total weight of the one or more particles.

In another preferred embodiment, the total content of the physiologically acceptable polymer is within the range of 15±12 wt.-%, more preferably 15±10 wt.-%, most preferably 15±7 wt.-%, and in particular 15±3 wt.-%, based on the total weight of the one or more particles.

In still another preferred embodiment, the total content of the physiologically acceptable polymer is within the range of 20±16 wt.-%, more preferably 20±12 wt.-%, most preferably 20±8 wt.-%, and in particular 20±4 wt.-%, based on the total weight of the one or more particles.

In yet another preferred embodiment, the total content of the physiologically acceptable polymer is within the range of 25±20 wt.-%, more preferably 25±15 wt.-%, most preferably 25±10 wt.-%, and in particular 25±5 wt.-%, based on the total weight of the one or more particles.

In a further preferred embodiment, the total content of the physiologically acceptable polymer is within the range of 30±20 wt.-%, more preferably 30±15 wt.-%, most preferably 30±10 wt.-%, and in particular 30±5 wt.-%, based on the total weight of the one or more particles.

In still a further preferred embodiment, the total content of the physiologically acceptable polymer is within the range of 35±20 wt.-%, more preferably 35±15 wt.-%, most preferably 35±10 wt.-%, and in particular 35±5 wt.-%, based on the total weight of the one or more particles.

In a still further preferred embodiment, the total content of the physiologically acceptable polymer is within the range of 40±20 wt.-%, more preferably 40±15 wt.-%, and most preferably 40±10 wt.-%, and in particular 40±5 wt.-%, based on the total weight of the one or more particles.

In a yet further preferred embodiment, the total content of the physiologically acceptable polymer is within the range of 45±20 wt.-%, more preferably 45±15 wt.-%, and most preferably 45±10 wt.-%, and in particular 45±5 wt.-%, based on the total weight of the one or more particles.

In another preferred embodiment, the total content of the physiologically acceptable polymer is within the range of 50±20 wt.-%, more preferably 50±15 wt.-%, and most preferably 50±10 wt.-%, and in particular 50±5 wt.-%, based on the total weight of the one or more particles.

In a yet further preferred embodiment, the total content of the physiologically acceptable polymer is within the range of 55±20 wt.-%, more preferably 55±15 wt.-%, and most preferably 55±10 wt.-%, and in particular 55±5 wt.-%, based on the total weight of the one or more particles.

In another preferred embodiment, the total content of the physiologically acceptable polymer is within the range of 60±20 wt.-%, more preferably 60±15 wt.-%, and most preferably 60±10 wt.-%, and in particular 60±5 wt.-%, based on the total weight of the one or more particles.

In a yet further preferred embodiment, the total content of the physiologically acceptable polymer is within the range of 65±20 wt.-%, more preferably 65±15 wt.-%, and most preferably 65±10 wt.-%, and in particular 65±5 wt.-%, based on the total weight of the one or more particles.

In another preferred embodiment, the total content of the physiologically acceptable polymer is within the range of 70±20 wt.-%, more preferably 70±15 wt.-%, and most preferably 70±10 wt.-%, and in particular 70±5 wt.-%, based on the total weight of the one or more particles.

In a yet further preferred embodiment, the total content of the physiologically acceptable polymer is within the range of 75±20 wt.-%, more preferably 75±15 wt.-%, and most preferably 75±10 wt.-%, and in particular 75±5 wt.-%, based on the total weight of the one or more particles.

In another preferred embodiment, the total content of the physiologically acceptable polymer is within the range of 80±20 wt.-%, more preferably 80±15 wt.-%, and most preferably 80±10 wt.-%, and in particular 80±5 wt.-%, based on the total weight of the one or more particles.

Preferably, the total content of the physiologically acceptable polymer is within the range of from 1 to 99 wt.-%, more preferably 3 to 90 wt.-%, still more preferably 5 to 75 wt.-%, yet more preferably 7 to 70 wt.-%, most preferably 10 to 65 wt.-% or 10 to 70 wt.-% and in particular 10 to 60 wt.-%, based on the total weight of the pharmaceutical dosage form.

In a preferred embodiment, the total content of the physiologically acceptable polymer is at least 2 wt.-%, more preferably at least 5 wt.-%, still more preferably at least 10 wt.-%, yet more preferably at least 15 wt.-% and in particular at least 20 wt.-%, based on the total weight of the pharmaceutical dosage form.

In a preferred embodiment, the total content of the physiologically acceptable polymer is within the range of 10±8 wt.-%, more preferably 10±6 wt.-%, most preferably 10±4 wt.-%, and in particular 10±2 wt.-%, based on the total weight of the pharmaceutical dosage form.

In another preferred embodiment, the total content of the physiologically acceptable polymer is within the range of 15±12 wt.-%, more preferably 15±10 wt.-%, most preferably 15±7 wt.-%, and in particular 15±3 wt.-%, based on the total weight of the pharmaceutical dosage form.

In still another preferred embodiment, the total content of the physiologically acceptable polymer is within the range of 20±16 wt.-%, more preferably 20±12 wt.-%, most preferably 20±8 wt.-%, and in particular 20±4 wt.-%, based on the total weight of the pharmaceutical dosage form.

In yet another preferred embodiment, the total content of the physiologically acceptable polymer is within the range of 25±20 wt.-%, more preferably 25±15 wt.-%, most preferably 25±10 wt.-%, and in particular 25±5 wt.-%, based on the total weight of the pharmaceutical dosage form.

In a further preferred embodiment, the total content of the physiologically acceptable polymer is within the range of 30±20 wt.-%, more preferably 30±15 wt.-%, most preferably 30±10 wt.-%, and in particular 30±5 wt.-%, based on the total weight of the pharmaceutical dosage form.

In still a further preferred embodiment, the total content of the physiologically acceptable polymer is within the range of 35±20 wt.-%, more preferably 35±15 wt.-%, most preferably 35±10 wt.-%, and in particular 35±5 wt.-%, based on the total weight of the pharmaceutical dosage form.

In a still further preferred embodiment, the total content of the physiologically acceptable polymer is within the range of 40±20 wt.-%, more preferably 40±15 wt.-%, and most preferably 40±10 wt.-%, and in particular 40±5 wt.-%, based on the total weight of the pharmaceutical dosage form.

In a yet further preferred embodiment, the total content of the physiologically acceptable polymer is within the range of 45±20 wt.-%, more preferably 45±15 wt.-%, and most preferably 45±10 wt.-%, and in particular 45±5 wt.-%, based on the total weight of the pharmaceutical dosage form.

In another preferred embodiment, the total content of the physiologically acceptable polymer is within the range of 50±20 wt.-%, more preferably 50±15 wt.-%, and most preferably 50±10 wt.-%, and in particular 50±5 wt.-%, based on the total weight of the pharmaceutical dosage form.

In still another preferred embodiment, the total content of the physiologically acceptable polymer is within the range of 60±20 wt.-%, more preferably 60±15 wt.-%, and most preferably 60±10 wt.-%, and in particular 60±5 wt.-%, based on the total weight of the pharmaceutical dosage form.

In yet another preferred embodiment, the total content of the physiologically acceptable polymer is within the range of 70±20 wt.-%, more preferably 70±15 wt.-%, and most preferably 70±10 wt.-%, and in particular 70±5 wt.-%, based on the total weight of the pharmaceutical dosage form.

Preferably, the relative weight ratio of the physiologically acceptable polymer to the pharmacologically active ingredient is within the range of 40:1 to 1:40 or 35:1 to 1:35 or 30:1 to 1:30 or 20:1 to 1:20, more preferably 15:1 to 1:15, still more preferably 10:1 to 1:10, yet more preferably 7:1 to 1:7, most preferably 5:1 to 1:5, and in particular 2:1 to 1:2.

Preferably, the physiologically acceptable polymer is selected from the group consisting of polyalkylene oxides, non-ionic acrylates, anionic acrylates and cationic acrylates.

The physiologically acceptable polymer is preferably selected from the group consisting of polyalkylene oxides (preferably polymethylene oxide, polyethylene oxide, polypropylene oxide), polyethylenes, polypropylenes, polyvinyl chlorides, polycarbonates, polystyrenes, polyacrylates, poly(hydroxy fatty acids), poly(hydroxyvaleric acids); polycaprolactones, polyvinyl alcohols, polyesteramides, polyethylene succinates, polylactones, polyglycolides, cellulose ethers (preferably methylcellulose, ethylcellulose, hydroxyethylcellulose, hydroxypropylcellulose, hydroxypropylmethylcellulose), polyurethanes, polyvinylpyrrolidones, poly-amides, polylactides, polyacetals, polylactide/glycolides, polylactones, polyglycolides, polyorthoesters, polyanhydrides, copolymers thereof, block-copolymers thereof, and mixtures of at least two of the stated polymers.

In a preferred embodiment, the physiologically acceptable polymer is non-ionic. In another preferred embodiment, the physiologically acceptable polymer is anionic. In still another preferred embodiment, the physiologically acceptable polymer is cationic.

Preferably, the physiologically acceptable polymer is selected from acrylic polymers or polyalkylene oxides.

In a particularly preferred embodiment,
(i) the content of the physiologically acceptable polymer is at least 30 wt.-% relative to the total weight of the one or more particles; and/or
(ii) the physiologically acceptable polymer is selected from acrylic polymers or polyalkylene oxides.

In a preferred embodiment, physiologically acceptable polymer is an acrylic polymer which is preferably derived from a monomer mixture comprising a first $C_{1-4}$-alkyl (meth)acrylate and a second $C_{1-4}$-alkyl (meth)acrylate differing from said first $C_{1-4}$-alkyl (meth)acrylate.

When the prolonged release matrix material of the prolonged release matrix comprises an acrylic polymer, it preferably does not additionally comprise an polyalkylene oxide or a waxy material, and vice versa. However, it is principally possible that the prolonged release matrix material of the prolonged release matrix comprises a combination of an acrylic polymer, a polyalkylene oxide and/or a waxy material.

Preferred $C_{1-4}$-alkyl (meth)acrylates include methyl methacrylate, methyl acrylate, ethyl methacrylate, ethyl acrylate, propyl methacrylate, propyl acrylate, butyl methacrylate, and butyl acrylate.

For the purpose of the specification, "(meth)acryl" refers to acryl as well as methacryl.

Preferably, the acrylic polymer has a weight average molecular weight within the range of from 100,000 g/mol to 2,000,000 g/mol. In a preferred embodiment, the acrylic polymer has a weight average molecular weight ($M_W$) or viscosity average molecular weight ($M_\eta$) of at least 150,000 or at least 200,000 g/mol, preferably at least 250,000 g/mol or at least 300,000 g/mol, more preferably in the range of about 300,000 g/mol to about 2,000,000 g/mol, and most preferably in the range of about 300,000 g/mol to about 1,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

The acrylic polymer can be a nonionic acrylic polymer or an ionic acrylic polymer. For the purpose of specification, "nonionic polymer" refers to a polymer not containing more than 1 mole.-% ionic, i.e. anionic or cationic, monomer units, preferably containing no ionic monomer units at all.

In a preferred embodiment, the physiologically acceptable polymer is a nonionic acrylic polymer which is preferably derived from a monomer mixture comprising a first $C_{1-4}$-alkyl (meth)acrylate and a second $C_{1-4}$-alkyl (meth)acrylate differing from said first $C_{1-4}$-alkyl (meth)acrylate.

Preferably, the first $C_{1-4}$-alkyl (meth)acrylate is ethyl acrylate and the second $C_{1-4}$-alkyl (meth)acrylate is methyl methacrylate.

Preferably, the relative molar content of the ethyl acrylate within the nonionic acrylic polymer is greater than the relative molar content of the methyl methacrylate within the nonionic acrylic polymer.

Preferably, the molar ratio of the first $C_{1-4}$-alkyl (meth)acrylate, which is preferably ethyl acrylate, to the second $C_{1-4}$-alkyl (meth)acrylate, which is preferably methyl methacrylate, is within the range of from 5:1 to 1:3, more preferably from 4.5:1 to 1:2.5, still more preferably from 4:1 to 1:2, yet more preferably from 3.5:1 to 1:1.5, even more preferably from 3:1 to 1:1, most preferably from 2.5:1 to 1.5:1, and in particular about 2:1.

Preferably, the nonionic acrylic polymer has a weight average molecular weight within the range of from 100,000 g/mol to 2,000,000 g/mol. In a preferred embodiment, the nonionic acrylic polymer has a weight average molecular weight ($M_W$) or viscosity average molecular weight ($M_\eta$) of at least 150,000 or at least 200,000 g/mol, preferably at least 250,000 g/mol or at least 300,000 g/mol, more preferably in the range of about 300,000 g/mol to about 2,000,000 g/mol, and most preferably in the range of about 300,000 g/mol to about 1,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

In a preferred embodiment, the weight average molecular weight of the nonionic acrylic polymer is within the range of 675,000±500,000 g/mol, more preferably 675,000±450,000 g/mol, still more preferably 675,000±400,000 g/mol, yet more preferably 675,000±350,000 g/mol, even more preferably 675,000±300,000 g/mol, most preferably 675,000±250,000 g/mol, and in particular 675,000±200,000 g/mol.

The nonionic acrylic polymer may comprise a single nonionic acrylic polymer having a particular average molecular weight, or a mixture (blend) of different nonionic acrylic polymers, such as two, three, four or five nonionic acrylic polymers, e.g., nonionic acrylic polymers of the same chemical nature but different average molecular weight, nonionic acrylic polymers of different chemical nature but same average molecular weight, or nonionic acrylic polymers of different chemical nature as well as different molecular weight.

In a preferred embodiment, the nonionic acrylic polymer is homogeneously distributed in the one or more particles. According to this embodiment, the pharmacologically active ingredient and the nonionic acrylic polymer are intimately homogeneously distributed in the one or more particles, so that the one or more particles do not contain any portions where either the pharmacologically active ingredient is present in the absence of nonionic acrylic polymer or where nonionic acrylic polymer is present in the absence of the pharmacologically active ingredient.

When the one or more particles are film coated, the nonionic acrylic polymer is preferably homogeneously distributed in the body of the one or more particles, i.e. the film coating preferably does not contain nonionic acrylic polymer. Nonetheless, the film coating as such may of course contain one or more polymers, which however, preferably differ from the nonionic acrylic polymer contained in the body.

The nonionic acrylic polymer preferably has a glass transition temperature ($T_g$) within the range of 1±15° C., more preferably 1±11° C.

The nonionic acrylic polymer preferably has a minimum film forming temperature (MFT) within the range of 5±5° C., more preferably 5±2° C.

Nonionic acrylic polymers that are suitable for use in the one or more particles according to the invention are commercially available, e.g. from Evonik. For example, Eudragit® NE30D, Eudragit® NE40D and Eudragit® NM30D, which are provided as aqueous dispersions of poly(ethyl acrylate-co-methyl methacrylate) 2:1, may be used in the one or more particles according to the invention. For details concerning the properties of these products, it can be referred to e.g. the product specification.

In a preferred embodiment, the physiologically acceptable polymer is an ionic acrylic polymer.

In a preferred embodiment, the ionic acrylic polymer is homogeneously distributed in the one or more particles. According to this embodiment, the pharmacologically active ingredient and the ionic acrylic polymer are intimately homogeneously distributed in the one or more particles, so that the one or more particles do not contain any portions where either the pharmacologically active ingredient is present in the absence of ionic acrylic polymer or where ionic acrylic polymer is present in the absence of the pharmacologically active ingredient.

When the one or more particles are film coated, the ionic acrylic polymer is preferably homogeneously distributed in the body of the one or more particles, i.e. the film coating preferably does not contain ionic acrylic polymer. Nonetheless, the film coating as such may of course contain one or more polymers, which however, preferably differ from the ionic acrylic polymer contained in the body.

Preferred ionic acrylic polymers are anionic acrylic polymers. Preferred anionic acrylic polymers include but are not limited to copolymers of one or two different $C_{1-4}$-alkyl (meth)acrylate monomers and copolymerizable anionic monomers such as acrylic acid. Preferred representatives are ternary copolymers of methyl acrylate, methyl methacrylate and methacrylic acid, wherein the relative molar content of the monomers is preferably methyl acrylate>methyl methacrylate>methacrylic acid. Preferably, the anionic acrylic polymer has a weight average molecular weight within the range of 280,000±250,000 g/mol, more preferably 280,000±200,000 g/mol, still more preferably 280,000±180,000 g/mol, yet more preferably 280,000±160,000 g/mol, even more preferably 280,000±140,000 g/mol, most preferably 280,000±120,000 g/mol, and in particular 280,000±100,000 g/mol. Poly(methyl acrylate-co-methyl methacrylate-co-methacrylic acid) 7:3:1 having an average molecular weight of about 280,000 g/mol is commercially available as Eudragit® FS.

Other preferred ionic acrylic polymers are cationic acrylic polymers. Preferred cationic acrylic polymers include but are not limited to copolymers of one or two different $C_{1-4}$alkyl (meth)acrylate monomers and copolymerizable cationic monomers such as trimethylammonioethyl methacrylate chloride. Preferred representatives are ternary copolymers of ethyl acrylate, methyl methacrylate and a low content of methacrylic acid ester with quaternary ammonium groups, preferably trimethylammonioethyl methacrylate chloride, wherein the relative molar content of the monomers is preferably methyl methacrylate>ethyl acrylate>copolymerizable cationic monomers. Preferably, the cationic acrylic polymer has a weight average molecular weight within the range of 32,000±30,000 g/mol, more preferably 32,000±27,000 g/mol, still more preferably 32,000±23,000 g/mol, yet more preferably 32,000±20,000 g/mol, even more preferably 32,000±17,000 g/mol, most preferably 32,000±13,000 g/mol, and in particular 32,000±10,000 g/mol. Poly(ethyl acrylate-co-methyl methacrylate-co-trimethylammonioethyl methacrylate chloride) 1:2:0.1 and 1:2:0.2, respectively, having an average molecular weight of about 32,000 g/mol is commercially available as Eudragit® RS-PO and Eudragit® RL-PO, respectively.

Because of its lower content of trimethylammonioethyl methacrylate chloride, Eudragit® RS-PO is particularly preferred. Another preferred cationic acrylic polymer is Eudragit® RL 100 which is a copolymer of ethyl acrylate, methyl methacrylate and a low content of methacrylic acid ester with quaternary ammonium groups.

In a preferred embodiment, the physiologically acceptable polymer is a polyalkylene oxide, preferably a polyethylene oxide, particularly preferably having a weight average molecular weight of at least 500,000 g/mol.

When the prolonged release matrix material of the prolonged release matrix comprises a polyalkylene oxide, it preferably does not additionally comprise an acrylic polymer or a waxy material, and vice versa.

In a preferred embodiment, the polyalkylene oxide is homogeneously distributed in the one or more particles. According to this embodiment, the pharmacologically active ingredient and the polyalkylene oxide are intimately homogeneously distributed in the one or more particles, so that the one or more particles do not contain any portions where either the pharmacologically active ingredient is present in the absence of polyalkylene oxide or where polyalkylene oxide is present in the absence of the pharmacologically active ingredient.

When the one or more particles are film coated, the polyalkylene oxide is preferably homogeneously distributed in the body of the one or more particles, i.e. the film coating preferably does not contain polyalkylene oxide. Nonetheless, the film coating as such may of course contain one or more polymers, which however, preferably differ from the polyalkylene oxide contained in the body.

Preferably, the polyalkylene oxide is selected from polymethylene oxide, polyethylene oxide and polypropylene oxide, or copolymers or mixtures thereof.

Preferably, the polyalkylene oxide has a weight average molecular weight ($M_W$), preferably also a viscosity average molecular weight ($M_\eta$) of more than 200,000 g/mol or at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Preferably, the molecular weight dispersity $M_w/M_n$ of the polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide preferably has a viscosity at 25° C. of 30 to 17,600 mPa·s, more preferably 55 to 17,600 mPa·s, still more preferably 600 to 17,600 mPa·s, yet more preferably 4,500 to 17,600 mPa·s, even more preferably 4,500 to 12,000 mPa·s, most preferably 5,000 to 10,500 mPa·s and in particular 5,500 to 7,500 mPa·s or 7,500 to 10,000 mPa·s, measured in a 1 wt.-% aqueous solution.

The polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of specification, a polyalkylene glycol has a molecular weight of up to 20,000 g/mol whereas a polyalkylene oxide has a molecular weight of more than 20,000 g/mol. The weight average over all molecular weights of all polyalkylene oxides that are contained in the pharmaceutical dosage form is more than 200,000 g/mol. Thus, polyalkylene glycols, if any, are preferably not taken into consideration when determining the weight average molecular weight of polyalkylene oxide.

In a particularly preferred embodiment, the physiologically acceptable polymer is a polyalkylene oxide the content of which is at least 30 wt.-% relative to the total weight of the one or more particles.

Preferably, the polyalkylene oxide is combined with another polymer, preferably a cellulose ether, particularly preferably a cellulose ether selected from the group consisting of methylcellulose, ethylcellulose, hydroxyethylcellulose, hydroxypropylcellulose, and hydroxypropylmethylcellulose. Hydroxypropylmethylcellulose is particularly preferred.

Preferably, the relative weight ratio of the polyalkylene oxide and the cellulose ether is within the range of from 14:1 to 1:2, more preferably 13:1 to 1:1, still more preferably 12:1 to 2:1, yet more preferably 11:1 to 3:1, even more preferably 10:1 to 4:1, most preferably 9:1 to 5:1, and in particular 8:1 to 6:1.

In another preferred embodiment, the prolonged release matrix material comprises a waxy material, preferably selected from the group consisting of
  glycerides, especially monoglycerides, diglycerides, triglycerides,
  esters of fatty acids with fatty alcohols, and
  paraffins.

When the prolonged release matrix material of the prolonged release matrix comprises a waxy material, it preferably does not additionally comprise an acrylic polymer or a polyalkylene oxide, and vice versa.

As used herein a "waxy material" refers to a material which melts into liquid form having low viscosity upon heating and sets again to a solid state upon cooling. Preferably, the waxy material has a melting point of at least 30° C., more preferably at least 35° C., still more preferably at least 40° C., yet more preferably at least 45° C., even more preferably at least 50° C., most preferably at least 55° C., and in particular at least 60° C.

When the waxy material is or comprises a monoglyceride, diglyceride, triglyceride or a mixture thereof, it is preferably a mono-, di- or triester of glycerol and carboxylic acids, whereas the carboxylic acid is preferably selected from the group consisting of fatty acids, hydroxy fatty acids and aromatic acids.

In another preferred embodiment, the glyceride is a fatty acid macrogolglyceride, e.g. lauroyl macrogolglyceride, such as Gelucire 44/14 that can be regarded as a non-ionic water dispersible surfactant composed of well-characterized PEG-esters, a small glyceride fraction and free PEG Preferred glycerides of fatty acids include monoglycerides, diglycerides, triglycerides, and mixtures thereof; preferably of $C_6$ to $C_{22}$ fatty acids. Especially preferred are partial glycerides of the $C_{16}$ to $C_{22}$ fatty acids such as glycerol behenat, glycerol monostearate, glycerol palmitostearate and glyceryl distearate as well as triglycerides of the $C_{16}$ to $C_{22}$ fatty acids such as glycerol tristearate.

The term "fatty acid" is well acknowledged in the art and includes for example unsaturated representatives such as myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid; as well as saturated representatives such as caprylic acid, capric acid, lauric acid, myristic acid, palmitic acid, stearic acid, arachidic acid, behenic acid, lignoceric acid, and cerotic acid.

The term "hydroxy fatty acid" is also well acknowledged in the art and includes for example 2-hydroxyhexanoic acid, 2-hydroxyoctanoic acid, 2-hydroxydecanoic acid, 2-hydroxydodecanoic acid, β-hydroxylauric acid, 2-hydroxytetradecanoic acid, β-hydroxymyristic acid, 15-hydroxypentadecanoic acid, 16-hydroxyhexadecanoic acid, β-hydroxypalmitic acid, 12-hydroxyoctadecanoic acid, α-hydroxystearic acid, and α-hydroxyarachidic acid.

The fatty acids and the hydroxy fatty acids are preferably saturated.

When the waxy material is or comprises a diglyceride or a triglyceride, the fatty acids, hydroxy fatty acids and aromatic acids, respectively, may be identical or different.

According to this embodiment of the invention, the waxy material is preferably a hard fat (adeps solidus) in accordance with Ph. Eur.

Preferably, the waxy material is a monoglyceride, diglyceride, triglyceride or a mixture thereof, selected from the group consisting of hydrogenated soybean oil, hydrogenated palm oil, hydrogenated castor oil, hydrogenated cottonseed oil, and mixtures thereof.

When the waxy material is or comprises an ester of a fatty acid with a fatty alcohol, the fatty acid is preferably a saturated fatty acid. Preferred examples of fatty acids are already mentioned above in connection with the glycerides. The fatty alcohol is preferably derived from a fatty acid and preferably also saturated.

Preferred representatives of esters of fatty acids with fatty alcohols include but are not limited to natural waxes such as beeswax, carnaubawax, candelilla wax, ouricury wax, sugarcane wax, cetyl palmitate, oleyl oleate, cetaceum and retamo wax.

When the waxy material is or comprises paraffin, the paraffin is preferably a hard paraffin (paraffinum solidum, ceresin, zeresin) in accordance with Ph. Eur.

The waxy material may comprise a single waxy material, or a mixture (blend) of different waxy materials, such as two, three, four or five waxy materials, each of which preferably being selected from the group consisting of glycerides, especially monoglycerides, diglycerides, triglycerides; esters of fatty acids with fatty alcohols; and paraffins.

In a preferred embodiment, the waxy material is homogeneously distributed in the one or more particles. According to this embodiment, the pharmacologically active ingredient and the waxy material are intimately homogeneously distributed in the one or more particles, so that the one or more particles do not contain any portions where either the pharmacologically active ingredient is present in the absence of waxy material or where waxy material is present in the absence of the pharmacologically active ingredient.

When the one or more particles are film coated, the waxy material is preferably homogeneously distributed in the one or more particles, i.e. the film coating preferably does not contain waxy material. Nonetheless, the film coating as such may of course contain one or more waxy materials, which however, preferably differ from the waxy materials contained in the body.

Waxy materials that are suitable for use in the pharmaceutical dosage forms according to the invention are commercially available, e.g. Cera alba, Cera flava, Kolliwax™ HCO, Dynasan® 118, Compritol® 888 ATO, Precirol® ATO 5, Gelucire® 44/14, and the like. For details concerning the properties of these products, it can be referred to e.g. the product specification. The total content of the waxy material is preferably within the range of from 5.0 to 95 wt.-%, more preferably 10 to 90 wt.-%, still more preferably 15 to 85 wt.-%, yet more preferably 20 to 80 wt.-%, even more preferably 25 to 75 wt.-%, most preferably 30 to 70 wt.-%, and in particular 35 to 75 wt.-%, relative to the total weight of the prolonged release matrix.

Preferably, the total content of the waxy material is within the range of from 1 to 90 wt.-%, more preferably 3 to 85 wt.-%, still more preferably 5 to 80 wt.-%, yet more preferably 7 to 75 wt.-%, most preferably 10 to 70 wt.-% and in particular 15 to 65 wt.-%, based on the total weight of the one or more particles.

In a preferred embodiment, the total content of the waxy material is at least 2 wt.-%, more preferably at least 5 wt.-%, still more preferably at least 10 wt.-%, yet more preferably at least 15 wt.-% and in particular at least 20 wt.-%, based on the total weight of the one or more particles.

In a preferred embodiment, the total content of waxy material is within the range of 10±8 wt.-%, more preferably 10±6 wt.-%, most preferably 10±4 wt.-%, and in particular 10±2 wt.-%, based on the total weight of the one or more particles.

In another preferred embodiment, the total content of waxy material is within the range of 15±12 wt.-%, more preferably 15±10 wt.-%, most preferably 15±7 wt.-%, and in particular 15±3 wt.-%, based on the total weight of the one or more particles.

In still another preferred embodiment, the total content of waxy material is within the range of 20±16 wt.-%, more preferably 20±12 wt.-%, most preferably 20±8 wt.-%, and in particular 20±4 wt.-%, based on the total weight of the one or more particles.

In yet another preferred embodiment, the total content of waxy material is within the range of 25±20 wt.-%, more preferably 25±15 wt.-%, most preferably 25±10 wt.-%, and in particular 25±5 wt.-%, based on the total weight of the one or more particles.

In a further preferred embodiment, the total content of waxy material is within the range of 30±20 wt.-%, more preferably 30±15 wt.-%, most preferably 30±10 wt.-%, and in particular 30±5 wt.-%, based on the total weight of the one or more particles.

In still a further preferred embodiment, the total content of waxy material is within the range of 35±20 wt.-%, more preferably 35±15 wt.-%, most preferably 35±10 wt.-%, and in particular 35±5 wt.-%, based on the total weight of the one or more particles.

In a still further preferred embodiment, the total content of waxy material is within the range of 40±20 wt.-%, more preferably 40±15 wt.-%, and most preferably 40±10 wt.-%, and in particular 40±5 wt.-%, based on the total weight of the one or more particles.

In a yet further preferred embodiment, the total content of waxy material is within the range of 45±20 wt.-%, more preferably 45±15 wt.-%, and most preferably 45±10 wt.-%, and in particular 45±5 wt.-%, based on the total weight of the one or more particles.

In another preferred embodiment, the total content of waxy material is within the range of 50±20 wt.-%, more preferably 50±15 wt.-%, and most preferably 50±10 wt.-%, and in particular 50±5 wt.-%, based on the total weight of the one or more particles.

In a yet further preferred embodiment, the total content of waxy material is within the range of 55±20 wt.-%, more preferably 55±15 wt.-%, and most preferably 55±10 wt.-%, and in particular 55±5 wt.-%, based on the total weight of the one or more particles.

In another preferred embodiment, the total content of waxy material is within the range of 60±20 wt.-%, more preferably 60±15 wt.-%, and most preferably 60±10 wt.-%, and in particular 60±5 wt.-%, based on the total weight of the one or more particles.

In a yet further preferred embodiment, the total content of waxy material is within the range of 65±20 wt.-%, more preferably 65±15 wt.-%, and most preferably 65±10 wt.-%, and in particular 65±5 wt.-%, based on the total weight of the one or more particles.

In another preferred embodiment, the total content of waxy material is within the range of 70±20 wt.-%, more preferably 70±15 wt.-%, and most preferably 70±10 wt.-%, and in particular 70±5 wt.-%, based on the total weight of the one or more particles.

In a yet further preferred embodiment, the total content of waxy material is within the range of 75±20 wt.-%, more preferably 75±15 wt.-%, and most preferably 75±10 wt.-%, and in particular 75±5 wt.-%, based on the total weight of the one or more particles.

In another preferred embodiment, the total content of waxy material is within the range of 80±20 wt.-%, more preferably 80±15 wt.-%, and most preferably 80±10 wt.-%, and in particular 80±5 wt.-%, based on the total weight of the one or more particles.

Preferably, the relative weight ratio of the waxy material to the pharmacologically active ingredient is within the range of 20:1 to 1:20, more preferably 15:1 to 1:15, still more preferably 10:1 to 1:10, yet more preferably 7:1 to 1:7, most preferably 5:1 to 1:5, and in particular 2:1 to 1:2.

Besides the pharmacologically active ingredient and the physiologically acceptable polymer the one or more particles may optionally further comprise additional pharmaceutical excipients conventionally contained in pharmaceutical dosage forms in conventional amounts, such as antioxidants, preservatives, lubricants, plasticizer, fillers/binders, and the like.

The skilled person will readily be able to determine appropriate further excipients as well as the quantities of each of these excipients. Specific examples of pharmaceutically acceptable carriers and excipients are described in the Handbook of Pharmaceutical Excipients, American Pharmaceutical Association (1986).

In a preferred embodiment, the one or more particles do not contain a disintegrant.

Preferably, the one or more particles further comprise an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the one or more particles.

In a preferred embodiment, the one or more particles further comprise an acid, preferably a carboxylic acid, more preferably a multicarboxylic acid, particularly citric acid. The content of acid is preferably in the range of 0.01 wt.-% to about 20 wt.-%, more preferably in the range of 0.02 wt.-% to about 10 wt.-%, and still more preferably in the range of 0.05 wt.-% to about 5 wt.-%, and most preferably in the range of 0.1 wt.-% to about 1.0 wt.-%, based on the total weight of the one or more particles.

In a preferred embodiment, the one or more particles contain at least one lubricant. In another preferred embodiment, the one or more particles contain no lubricant.

Especially preferred lubricants are selected from
magnesium stearate, calcium stearate and stearic acid;
polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;
polyglycolyzed glycerides, such as the one known and commercially available under the trade name "Labrasol";
fatty alcohols that may be linear or branched, such as cetylalcohol, stearylalcohol, cetylstearyl alcohol, 2-octyldodecane-1-ol and 2-hexyldecane-1-ol; and
polyethylene glycols having a molecular weight between 10.000 and 60.000 g/mol.

Particularly preferred lubricants comprise stearic acid, calcium stearate and stearyl alcohol or a mixture thereof.

Preferably, the content of the lubricant ranges from 0.01 wt.-% to about 10 or 15 wt.-%, more preferably in the range of 0.05 wt.-% to about 7.5 wt.-%, most preferably in the range of 0.1 wt.-% to about 5 wt.-% or 1.5 wt.-% to about 4 wt, and in particular in the range of 0.1 wt.-% to about 1 wt.-% or 3.5 to about 5.5 wt.-%, based on the total weight of the one or more particles.

When the one or more particles contain(s) more than one lubricant, preferably, the overall content of the lubricant ranges from 3 wt.-% to about 20 wt.-%, more preferably in the range of 5 wt.-% to about 15 wt.-%, most preferably in the range of 7 wt.-% to about 12 wt.-%, and in particular in the range of 8 wt.-% to about 10 wt.-%, based on the total weight of the one or more particles.

Preferably, the one or more particles further comprise a plasticizer. The plasticizer improves the processability of the prolonged release matrix material. A preferred plasticizer is polyalkylene glycol, like polyethylene glycol, triethyl citrate (TEC), triacetin, fatty acids, fatty acid esters, waxes and/or microcrystalline waxes. Particularly preferred plasticizers are polyethylene glycols, such as PEG 6000. Further particularly preferred plasticizers comprise triethyl citrate (TEC), stearic acid, calcium stearate and stearyl alcohol or a mixture thereof.

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the one or more particles.

When the one or more particles contain more than one plasticizer, preferably, the overall amount of the plasticizer ranges from 3 wt.-% to about 20 wt.-%, more preferably in the range of 5 wt.-% to about 20 wt.-% or to about 15 wt.-%, most preferably in the range of 7 wt.-% to about 20 wt.-% or to about 12 wt.-%, and in particular in the range of 8 wt.-% to about 20 wt.-% or to about 10 wt.-%, based on the total weight of the one or more particles.

Plasticizers can sometimes act as a lubricant, and lubricants can sometimes act as a plasticizer.

Preferably, the one or more particles further comprise a filler/binder. A preferred filler/binder is selected from celluloses, cellulose derivatives such as cellulose ethers and cellulose esters, and tricalcium phosphate. A particularly preferred filler/binder is selected from cellulose esters and cellulose ethers, in particular hydroxypropyl methylcellulose (HPMC).

The content of the filler/binder, preferably HPMC, preferably ranges from 0.1 wt.-% to about 30 wt.-%, more preferably in the range of 1.0 wt.-% to about 20 wt.-%, and most preferably in the range of 2.0 wt.-% to about 15 wt.-% relative to the total weight of the one or more particles.

In a preferred embodiment, besides the pharmacologically active ingredient that may have any solubility in aqueous ethanol, relative to the total weight of the one or more particles, the one or more particles according to the invention preferably contain at most 25 wt.-%, more preferably at most 20 wt.-%, still more preferably at most 15 wt.-%, yet more preferably at most 10 wt.-%, even more preferably at most 5.0 wt.-%, most preferably at most 2.5 wt.-%, and in particular at most 1.0 wt.-% of ingredients (prolonged release matrix material, excipients, and the like) having at room temperature in aqueous ethanol (40 vol.-%) a solubility of at least 100 mg/ml, more preferably a solubility of at least 75 mg/ml, still more preferably a solubility of at least 50 mg/ml, yet more preferably a solubility of at least 25 mg/ml, even more preferably a solubility of at least 10 mg/ml, most preferably a solubility of at least 5.0 mg/ml, and in particular a solubility of at least 1.0 mg/ml.

Preferred contents of the pharmacologically active ingredient, physiologically acceptable polymer, and excipients, relative to the total weight of the one or more particles, are summarized as embodiments $B^1$ to $B^{28}$ in the tables here below:

| wt.- % | $B^1$ | $B^2$ | $B^3$ | $B^4$ |
|---|---|---|---|---|
| pharmacologically active ingredient | 40 ± 30 | 40 ± 20 | 40 ± 10 | 40 ± 5 |
| physiologically acceptable polymer | 50 ± 30 | 50 ± 20 | 50 ± 10 | 50 ± 5 |
| pharmaceutical excipients | 20 ± 20 | 20 ± 20 | 20 ± 20 | 20 ± 20 |

| wt.- % | $B^5$ | $B^6$ | $B^7$ | $B^8$ |
|---|---|---|---|---|
| pharmacologically active ingredient | 30 ± 25 | 30 ± 20 | 30 ± 10 | 30 ± 5 |
| physiologically acceptable polymer | 50 ± 30 | 50 ± 20 | 50 ± 10 | 50 ± 5 |
| pharmaceutical excipients | 20 ± 20 | 20 ± 20 | 20 ± 20 | 20 ± 20 |

| wt.- % | $B^9$ | $B^{10}$ | $B^{11}$ | $B^{12}$ |
|---|---|---|---|---|
| pharmacologically active ingredient | 20 ± 15 | 20 ± 12.5 | 20 ± 10 | 20 ± 5 |
| physiologically acceptable polymer | 50 ± 30 | 50 ± 20 | 50 ± 10 | 50 ± 5 |
| pharmaceutical excipients | 20 ± 20 | 20 ± 20 | 20 ± 20 | 20 ± 20 |

| wt.-% | B¹³ | B¹⁴ | B¹⁵ | B¹⁶ |
|---|---|---|---|---|
| pharmacologically active ingredient | 10 ± 7.5 | 10 ± 7.5 | 10 ± 5 | 10 ± 5 |
| physiologically acceptable polymer | 50 ± 30 | 50 ± 20 | 50 ± 10 | 50 ± 10 |
| pharmaceutical excipients | 20 ± 20 | 20 ± 20 | 20 ± 20 | 20 ± 20 |

| wt.-% | B¹⁷ | B¹⁸ | B¹⁹ | B²⁰ |
|---|---|---|---|---|
| pharmacologically active ingredient | 20 ± 15 | 20 ± 12.5 | 20 ± 10 | 20 ± 5 |
| physiologically acceptable polymer | 40 ± 30 | 40 ± 20 | 40 ± 10 | 40 ± 5 |
| pharmaceutical excipients | 20 ± 20 | 20 ± 20 | 20 ± 20 | 20 ± 20 |

| wt.-% | B²¹ | B²² | B²³ | B²⁴ |
|---|---|---|---|---|
| pharmacologically active ingredient | 20 ± 15 | 20 ± 12.5 | 20 ± 10 | 20 ± 5 |
| physiologically acceptable polymer | 60 ± 40 | 60 ± 30 | 60 ± 20 | 60 ± 10 |
| pharmaceutical excipients | 20 ± 20 | 20 ± 20 | 20 ± 20 | 20 ± 20 |

| wt.-% | B²⁵ | B²⁶ | B²⁷ | B²⁸ |
|---|---|---|---|---|
| pharmacologically active ingredient | 10 ± 9 | 10 ± 7 | 10 ± 5 | 10 ± 3 |
| physiologically acceptable polymer | 70 ± 40 | 60 ± 30 | 60 ± 20 | 60 ± 10 |
| pharmaceutical excipients | 20 ± 20 | 20 ± 20 | 20 ± 20 | 20 ± 20 |

Preferably, the one or more particles provide prolonged release of the pharmacologically active ingredient. Preferably, the physiologically acceptable polymer forms a prolonged release matrix that provides for a prolonged release of the pharmacologically active ingredient from the one or more particles.

Preferably, under in vitro conditions the pharmaceutical dosage form has released after 30 minutes 0.1 to 75%, after 240 minutes 0.5 to 95%, after 480 minutes 1.0 to 100% and after 720 minutes 2.5 to 100% of the pharmacologically active ingredient.

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 600 mL simulated intestinal fluid pH 6.8 (phosphate buffer) or pH 4.5. In a preferred embodiment, the rotational speed of the paddle is increased to 75 rpm. In another preferred embodiment, the release profile is determined under the following conditions: basket method, 75 rpm, 37±5° C., 600 mL 0.1 N HCl or 600 mL of SIF sp (pH 6.8) or 600 mL of 0.1 N HCl+40% ethanol.

Preferred release profiles $R^1$ to $R^6$ are summarized in the table here below [all data in wt.-% of released pharmacologically active ingredient]:

| time | $R^1$ | $R^2$ | $R^3$ | $R^4$ | $R^5$ | $R^6$ |
|---|---|---|---|---|---|---|
| 60 min | 0-30 | 0-50 | 0-50 | 15-25 | 20-30 | 20-50 |
| 120 min | 0-40 | 0-75 | 0-75 | 25-40 | 35-50 | 40-75 |
| 240 min | 3-55 | 3-95 | 10-95 | 40-70 | 55-75 | 60-95 |
| 480 min | 10-65 | 10-100 | 35-100 | 60-90 | 80-95 | 80-100 |
| 720 min | 20-75 | 20-100 | 55-100 | 70-100 | 90-100 | 90-100 |
| 960 min | 30-88 | 30-100 | 70-100 | >80 | 95-100 | |
| 1440 min | 50-100 | 50-100 | >90 | | | |
| 2160 min | >80 | >80 | | | | |

Further preferred release profiles $R^7$ to $R^{13}$ are summarized in the table here below [all data in wt.-% of released pharmacologically active ingredient]:

| time | $R^7$ | $R^8$ | $R^9$ | $R^{10}$ | $R^{11}$ | $R^{12}$ | $R^{13}$ |
|---|---|---|---|---|---|---|---|
| 30 min | 17.5 ± 7.5 | 17.5 ± 6.5 | 17.5 ± 5.5 | 17.5 ± 4.5 | 17.5 ± 3.5 | 17.5 ± 2.5 | 15 ± 6.5 |
| 60 min | 27.0 ± 8.0 | 27.0 ± 7.0 | 27.0 ± 6.0 | 27.0 ± 5.0 | 27.0 ± 4.0 | 27.0 ± 3.0 | 20 ± 7.0 |
| 120 min | 41.5 ± 9.5 | 41.5 ± 8.5 | 41.5 ± 7.5 | 41.5 ± 6.5 | 41.5 ± 5.5 | 41.5 ± 4.5 | 25 ± 8.5 |
| 240 min | 64.5 ± 12.5 | 64.5 ± 11.5 | 64.5 ± 10.5 | 64.5 ± 9.5 | 64.5 ± 8.5 | 64.5 ± 7.5 | 37 ± 11.5 |
| 480 min | 88.0 ± 12.0 | 88.0 ± 11.0 | 88.0 ± 10.0 | 88.0 ± 9.0 | 88.0 ± 8.0 | 88.0 ± 7.0 | 50 ± 11.0 |
| 720 min | 96.0 ± 9.0 | 96.0 ± 8.0 | 96.0 ± 7.0 | 96.0 ± 6.0 | 96.0 ± 5.0 | 96.0 ± 4.0 | 58 ± 8.0 |
| 840 min | 97.5 ± 7.5 | 97.5 ± 6.5 | 97.5 ± 5.5 | 97.5 ± 4.5 | 97.5 ± 3.5 | 97.5 ± 2.5 | 67 ± 15 |

Preferably, the pharmaceutical dosage form according to the invention has released at most 50% of the pharmacologically active ingredient after 60 min measured under in vitro conditions and in accordance with Ph. Eur.

In a particularly preferred embodiment; under in vitro conditions in 600 mL 0.1 N HCl, using the basket method according to Ph. Eur. at 75 rpm, after 1 h under physiological conditions, the pharmaceutical dosage form has released at most 60%, more preferably at most 55%, still more preferably at most 50%, yet more preferably at most 45%, even more preferably at most 40%, most preferably at most 3% and in particular at most 30% of the pharmacologically active ingredient relative to the total amount of the pharmacologically active ingredient originally contained in the pharmaceutical dosage form.

Preferably, the release profile, the pharmacologically active ingredient, the physiologically acceptable polymer and optionally present pharmaceutical excipients of the one or more particles are stable upon storage, preferably upon storage at elevated temperature, e.g. 40° C., for 3 months in sealed containers.

In connection with the release profile "stable" preferably means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

In connection with a pharmacologically active ingredient, the physiologically acceptable polymer and the pharmaceutical excipients "stable" preferably means that the particles and the pharmaceutical dosage form satisfy the requirements of EMA concerning shelf-life of pharmaceutical products.

Preferably, after storage for 4 weeks, more preferably 6 months, at 40° C. and 75% rel. humidity, the content of the pharmacologically active ingredient in the one or more particles and the pharmaceutical dosage form, respectively, amounts to at least 98.0%, more preferably at least 98.5%, still more preferably at least 99.0%, yet more preferably at least 99.2%, most preferably at least 99.4% and in particular at least 99.6%, of its original content before storage.

The tamper-resistant pharmaceutical dosage form according to the invention comprises one or more particles each having a breaking strength of at least 300 N. Preferably, the one or more particles exhibit a higher breaking strength than the further excipient(s).

In a preferred embodiment, the one or more particles containing pharmacologically active ingredient and physiologically acceptable polymer have a breaking strength of at least 300 N. When the pharmaceutical dosage form comprises more than one particle containing pharmacologically active ingredient and physiologically acceptable polymer, preferably at least a fraction of the individual particles, i.e. at least one or more particles have a breaking strength of at least 300 N.

Preferably, the mechanical properties, particularly the breaking strength, substantially rely on the presence and spatial distribution of the physiologically acceptable polymer, although its mere presence does typically not suffice in order to achieve said properties. The advantageous mechanical properties may not automatically be achieved by simply processing pharmacologically active ingredient, physiologically acceptable polymer, and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the desired properties may be obtained only if, during preparation of the one or more particles containing pharmacologically active ingredient and physiologically acceptable polymer,
  suitable components
  in suitable amounts
  are exposed to
  a sufficient pressure
  at a sufficient temperature
  for a sufficient period of time.

Thus, regardless of the apparatus used, the process protocols must be adapted in order to meet the required criteria. Therefore, the breaking strength is separable from the composition.

The one or more particles containing pharmacologically active ingredient and physiologically acceptable polymer preferably have a breaking strength of at least 300 N, at least 400 N, or at least 500 N, preferably at least 600 N, more preferably at least 700 N, still more preferably at least 800 N, yet more preferably at least 1000 N, most preferably at least 1250 N and in particular at least 1500 N.

The "breaking strength" (resistance to crushing) of a pharmaceutical dosage form or a particle is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Pharmaceutical dosage forms, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture a pharmaceutical dosage form and a particle, respectively (=breaking force). Therefore, for the purpose of the specification a pharmaceutical dosage form and particle, respectively, does preferably not exhibit the desired breaking strength when it breaks, i.e., is fractured into at least two independent parts that are separated from one another. In another preferred embodiment, however, the pharmaceutical dosage form and particle, respectively, is regarded as being broken if the force decreases by 25% (threshold value) of the highest force measured during the measurement (see below).

When the pharmaceutical dosage form is a capsule, e.g. a hard gelatine capsule, the true quantitative breaking strength of the capsule is difficult to measure; it may occur that the capsule does not fracture in the course of the measurement because of its flexibility. As conventional capsules apparently to not exhibit any increased breaking strength, for the purpose of specification the quantitative breaking strength of a capsule can preferably be regarded as being 0 N.

The one or more particles according to the invention are distinguished from conventional pharmaceutical dosage forms in that due to their breaking strength, they cannot be pulverized by the application of force with conventional means, such as for example a pestle and mortar, a hammer, a mallet or other usual means for pulverization, in particular devices developed for this purpose (pharmaceutical dosage form crushers). In this regard "pulverization" means crumbling into small particles. Avoidance of pulverization virtually rules out oral or parenteral, in particular intravenous or nasal abuse.

Preferably, the one or more particles containing pharmacologically active ingredient and physiologically acceptable polymer are tamper-resistant and provide resistance against grinding.

Conventional pharmaceutical dosage forms and particulate or monolithic particles, respectively, typically have a breaking strength well below 200 N.

The breaking strength of conventional round pharmaceutical dosage forms and particles may be estimated according to the following empirical formula:

$$\text{Breaking Strength [in N]} = 10 \times \text{Diameter of pharmaceutical dosage form/particulate [in mm]}.$$

Thus, according to said empirical formula, a round pharmaceutical dosage form/particle having a breaking strength of at least 300 N would require a diameter of at least 30 mm. Such a particle however, could not be swallowed, let alone a pharmaceutical dosage form containing a plurality of such particles. The above empirical formula preferably does not apply to the one or more particles according to the invention, which is not conventional but rather special.

Further, the actual mean chewing force is about 220 N (cf., e.g., P. A. Proeschel et al., J Dent Res, 2002, 81(7), 464-468). This means that conventional pharmaceutical dosage forms and particles, respectively, having a breaking strength well below 200 N may be crushed upon spontaneous chewing, whereas the one or more particles according to the invention may preferably not.

Still further, when applying a gravitational acceleration of about 9.81 m/s$^2$, 300 N correspond to a gravitational force of more than 30 kg, i.e. the one or more particles according to the invention can preferably withstand a weight of more than 30 kg without being pulverized.

Methods for measuring the breaking strength are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Pharmaceutical dosage forms". The particles may be subjected to the same or similar breaking strength test as the pharmaceutical dosage form. The test is intended to determine, under defined conditions, the resistance to crushing of pharmaceutical dosage forms and individual particles, respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the pharmaceutical dosage form and individual particle, respectively. The apparatus is calibrated using a system with a precision of 1 Newton. The pharmaceutical dosage form and particle, respectively, is placed between the jaws, taking into account, where applicable, the shape, the break-mark and the inscription; for each measurement the pharmaceutical dosage form and particle, respectively, is oriented in the same way with respect to the direction of application of the force (and the direction of extension in which the breaking strength is to be measured). The measurement is carried out on 10 pharmaceutical dosage forms and particles, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a pharmaceutical dosage form and individual particles, respectively, to fail (i.e., break) in a specific plane. The pharmaceutical dosage form and individual particle, respectively, is generally placed between two platens, one of which moves to apply sufficient force to the pharmaceutical dosage form and individual particle, respectively, to cause fracture. For conventional, round (circular cross-section) pharmaceutical dosage form and individual particles, respectively, loading occurs across their diameter (sometimes referred to as diametral loading), and fracture occurs in the plane. The breaking force of pharmaceutical dosage form and individual particle, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of pharmaceutical dosage form and individual particles, respectively, to the application of a compressive load. Although this term describes the true nature of the test more accurately than does hardness, it implies that pharmaceutical dosage form and individual particles, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$, 1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

In a preferred embodiment, the pharmaceutical dosage form and individual particle, respectively, is regarded as being broken if it is fractured into at least two separate pieces.

The one or more particles according to the invention preferably exhibit(s) mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or possibly even in liquid nitrogen), for it to be virtually impossible to pulverize by spontaneous chewing, grinding in a mortar, pounding, etc. Thus, preferably, the comparatively high breaking strength of the one or more particles according to the invention is maintained even at low or very low temperatures, e.g., when the pharmaceutical dosage form is initially chilled to increase its brittleness, for example to temperatures below −25° C., below −40° C. or even in liquid nitrogen.

The one or more particles according to the invention is/are characterized by a certain degree of breaking strength. This does not mean that it must also exhibit a certain degree of hardness. Hardness and breaking strength are different physical properties. Therefore, the preferred tamper-resistance of the one or more particles does not necessarily depend on the hardness of the one or more particles. For instance, due to its breaking strength, impact strength, elasticity modulus and tensile strength, respectively, the one or more particles can preferably be deformed, e.g. plastically, when exerting an external force, for example using a hammer, but cannot be pulverized, i.e., crumbled into a high number of fragments. In other words, the one or more particles according to the invention is/are characterized by a certain degree of breaking strength, but not necessarily also by a certain degree of form stability.

Therefore, in the meaning of the specification, a pharmaceutical dosage form and individual particle, respectively, that is deformed when being exposed to a force in a particular direction of extension but that does not break (plastic deformation or plastic flow) is preferably to be regarded as having the desired breaking strength in said direction of extension.

Preferred pharmaceutical dosage forms and individual particles, respectively, are those having a suitable tensile strength as determined by a test method currently accepted in the art. Further pharmaceutical dosage form and individual particles, respectively, are those having a Youngs Modulus as determined by a test method of the art. Still further pharmaceutical dosage form and individual particles, respectively, are those having an acceptable elongation at break.

In a preferred embodiment, the one or more particles containing pharmacologically active ingredient and physiologically acceptable polymer are tamper-resistant and provide(s) resistance against grinding and/or resistance against solvent extraction and/or resistance against dose-dumping in aqueous ethanol.

Tamper-resistant preferably means that the one or more particles containing pharmacologically active ingredient and physiologically acceptable polymer
(i) preferably provide(s) resistance against solvent extraction, and/or
(ii) preferably provide(s) resistance against grinding, and/or
(iii) preferably provide(s) resistance against dose-dumping in aqueous ethanol.

Thus, the one or more particles according to the invention do not necessarily need to exhibit any of resistances (i) to (iii); but may preferably exhibit any of resistances (i) to (iii) as well as any combination thereof; namely only (i); only (ii); only (iii); a combination of only (i) and (ii); a combination of only (i) and (iii); a combination of only (ii) and (iii); or a combination of (i) and (ii) and (iii).

Preferably, prolonged release of the pharmacologically active ingredient is achieved by a prolonged release matrix contained in the one or more particles which prolonged release matrix additionally provides tamper-resistance in terms of resistance against solvent extraction, resistance against grinding, and resistance against dose-dumping in aqueous ethanol.

As used herein, the term "tamper-resistant" refers to pharmaceutical dosage forms or particles that are resistant to conversion into a form suitable for misuse or abuse, particular for nasal and/or intravenous administration, by conventional means.

In this regard, the pharmaceutical dosage form as such it may be crushable by conventional means such as grinding in a mortar or crushing by means of a hammer. However, the one or more particles contained in the pharmaceutical dosage form preferably exhibit mechanical properties such that they cannot be pulverized by conventional means any further. As the one or more particles are of macroscopic size and contain the pharmacologically active ingredient, they cannot be administered nasally thereby rendering the pharmaceutical dosage form tamper-resistant.

Further, when trying to disrupt the pharmaceutical dosage forms by means of a hammer or mortar, the particles containing pharmacologically active ingredient and physiologically acceptable polymer tend to adhere to one another thereby forming aggregates and agglomerates, respectively, which are larger in size than the untreated particles.

Preferably, the prolonged release matrix of the one or more particles provides resistance against solvent extraction.

Preferably, when trying to tamper the pharmaceutical dosage form in order to prepare a formulation suitable for abuse by intravenous administration, the liquid part of the formulation that can be separated from the remainder by means of a syringe at room temperature is as less as possible, preferably it contains not more than 45 or 40 wt.-%, more preferably not more than 35 wt.-%, still more preferably not more than 30 wt.-%, yet more preferably not more than 25 wt.-%, even more preferably not more than 20 wt.-%, most preferably not more than 15 wt.-% and in particular not more than 10 wt.-% of the originally contained pharmacologically active ingredient.

Preferably, this property is tested by (i) dispensing a pharmaceutical dosage form that is either intact or has been manually comminuted by means of two spoons in 5 ml of solvent, either purified water or aqueous ethanol (40 vol. %), (ii) allowing the dispersion to stand for 10 min at room temperature, (iii) drawing up the hot liquid into a syringe (needle 21G equipped with a cigarette filter), and (iv) determining the amount of the pharmacologically active ingredient contained in the liquid within the syringe.

Preferably, the prolonged release matrix of the one or more particles contained in the pharmaceutical dosage form according to the invention provides resistance against grinding.

Preferably, when the one or more particles are treated with a commercial coffee mill, preferably type Bosch MKM6000, 180W, Typ KM13 for 2 minutes, 42±17.5 wt.-%, more preferably 42±15 wt.-%, still more preferably 42±12.5 wt.-%, yet more preferably 42±10 wt.-%, even more preferably 42±7.5 wt.-%, most preferably 42±5 wt.-%, and in particular 42±2.5 wt.-%, of the total weight of the thus obtained material does not pass a sieve having a mesh size of 1.000 mm.

Preferably, when the one or more particles are treated with a commercial coffee mill, preferably type Bosch MKM6000, 180W, Typ KM13, for 2 minutes, 57±17.5 wt.-%, more preferably 57±15 wt.-%, still more preferably 57±12.5 wt.-%, yet more preferably 57±10 wt.-%, even more preferably 57±7.5 wt.-%, most preferably 57±5 wt.-%, and in particular 57±2.5 wt.-%, of the total weight of the thus obtained material does not pass a sieve having a mesh size of 1.000 mm.

Preferably, when the one or more particles are treated with a commercial coffee mill, preferably type Bosch MKM6000, 180W, Typ KM13, for 2 minutes, at least 50 wt.-%, more preferably at least 55 wt.-%, still more preferably at least 60 wt.-%, yet more preferably at least 65 wt.-%, even more preferably at least 70 wt.-%, most preferably at least 75 wt.-%, and in particular at least 80 wt.-%, of the total weight of the thus obtained material does not pass a sieve having a mesh size of 1.000 mm.

Preferably, when the pharmaceutical dosage form is treated with a commercial coffee mill, preferably type Bosch MKM6000, 180W, Typ KM13 for 2 minutes, 42±17.5 wt.-%, more preferably 42±15 wt.-%, still more preferably 42±12.5 wt.-%, yet more preferably 42±10 wt.-%, even more preferably 42±7.5 wt.-%, most preferably 42±5 wt.-%, and in particular 42±2.5 wt.-%, of the total weight of the thus obtained material does not pass a sieve having a mesh size of 1.000 mm.

Preferably, when the pharmaceutical dosage form is treated with a commercial coffee mill, preferably type Bosch MKM6000, 180W, Typ KM13, for 2 minutes, 57±17.5 wt.-%, more preferably 57±15 wt.-%, still more preferably 57±12.5 wt.-%, yet more preferably 57±10 wt.-%, even more preferably 57±7.5 wt.-%, most preferably 57±5 wt.-%, and in particular 57±2.5 wt.-%, of the total weight of the thus obtained material does not pass a sieve having a mesh size of 1.000 mm.

Preferably, when the pharmaceutical dosage form is treated with a commercial coffee mill, preferably type Bosch MKM6000, 180W, Typ KM13, for 2 minutes, at least 50 wt.-%, more preferably at least 55 wt.-%, still more preferably at least 60 wt.-%, yet more preferably at least 65 wt.-%, even more preferably at least 70 wt.-%, most preferably at least 75 wt.-%, and in particular at least 80 wt.-%, of the total weight of the thus obtained material does not pass a sieve having a mesh size of 1.000 mm.

Particle size distributions of the ground pharmaceutical dosage form are preferably determined by sieve analysis.

In a preferred embodiment, after treatment with a commercial coffee mill as described above, more than 55%, more preferably more than 60%, still more preferably more than 65%, yet more preferably more than 70%, most preferably 75% and in particular more than 80% of the particles of the ground one or more particles and pharmaceutical dosage form, respectively, have a size in the range of from 0.2 to 3.3 nm, more preferably of from 0.4 to 3.1 nm, most preferably of from 0.6 to 2.9 and in particular of from 0.7 to 2.8 nm.

Preferred particle size distributions $P^1$ to $P^6$ are summarized in the table here below:

| particle size [nm] | amount [wt.-%] | | | | | |
|---|---|---|---|---|---|---|
| | $P^1$ | $P^2$ | $P^3$ | $P^4$ | $P^5$ | $P^6$ |
| <0.045 | 0.5 ± 0.4 | 0.1 ± 0.09 | 0.3 ± 0.29 | 0.3 ± 0.29 | 0.3 ± 0.29 | 0.3 ± 0.29 |
| 0.045-0.063 | 0.5 ± 0.4 | 0.3 ± 0.29 | 0.3 ± 0.29 | 0.3 ± 0.29 | 0.3 ± 0.29 | 0.3 ± 0.29 |
| 0.063-0.090 | 0.5 ± 0.4 | 0.3 ± 0.29 | 0.3 ± 0.29 | 1.0 ± 0.9 | 0.3 ± 0.29 | 0.3 ± 0.29 |
| 0.090-0.125 | 0.5 ± 0.4 | 0.3 ± 0.29 | 0.3 ± 0.29 | 1.0 ± 0.9 | 0.3 ± 0.29 | 1.0 ± 0.9 |
| 0.125-0.180 | 0.5 ± 0.4 | 3.0 ± 2.9 | 2.0 ± 1.5 | 2.0 ± 1.5 | 1.0 ± 0.9 | 1.0 ± 0.9 |
| 0.180-0.250 | 1.5 ± 1.4 | 1.0 ± 0.8 | 2.0 ± 1.5 | 1.0 ± 0.9 | 2.0 ± 1.5 | 1.0 ± 0.9 |
| 0.250-0.355 | 4.0 ± 3.5 | 5.0 ± 4.0 | 4.0 ± 3.5 | 3.5 ± 2.5 | 5.0 ± 4.0 | 3.0 ± 2.9 |
| 0.355-0.500 | 7.0 ± 6.0 | 5.0 ± 4.0 | 6.0 ± 4.5 | 7.0 ± 6.0 | 7.0 ± 6.0 | 7.0 ± 6.0 |
| 0.500-0.710 | 11.0 ± 8.0 | 9.0 ± 7.0 | 11.0 ± 8.0 | 10.0 ± 7.0 | 13.0 ± 10.0 | 9.0 ± 7.0 |
| 0.710-1.000 | 15.0 ± 12.0 | 10.0 ± 7.0 | 17.0 ± 14.0 | 18.0 ± 15.0 | 18.0 ± 15.0 | 13.0 ± 10.0 |
| 1.000-1.400 | 20.0 ± 17.0 | 18.0 ± 15.0 | 23.0 ± 20.0 | 28.0 ± 25.0 | 25.0 ± 22.0 | 20.0 ± 17.0 |
| 1.400-2.000 | 23.0 ± 20.0 | 19.0 ± 16.0 | 12.0 ± 9.0 | 18.0 ± 15.0 | 10.0 ± 7.0 | 22.0 ± 19.0 |
| 2.000-2.800 | 13.0 ± 10.0 | 16.0 ± 13.0 | 13.0 ± 10.0 | 11.0 ± 8.0 | 14.0 ± 11.0 | 12.0 ± 9.0 |
| 2.800-4.000 | 1.0 ± 0.8 | 14.0 ± 11.0 | 12.0 ± 9.0 | 0.3 ± 0.29 | 4.0 ± 3.5 | 9.0 ± 7.0 |
| >4.00 | 0.5 ± 0.45 | 0.3 ± 0.29 | 0.3 ± 0.29 | 0.5 ± 0.45 | 0.3 ± 0.29 | 0.5 ± 0.45 |

Preferably, the prolonged release matrix of the one or more particles contained in the pharmaceutical dosage form according to the invention provides resistance against dose-dumping in aqueous ethanol.

The pharmaceutical dosage form can be tested in vitro using ethanol/simulated gastric fluid of 0%, 20% and 40% to evaluate alcohol extractability. Testing is preferably performed using standard procedures, e.g. USP Apparatus 1 (basket) or USP Apparatus 2 (paddle) at e.g. 50 rpm in e.g. 500 ml of media at 37° C., using a Perkin Elmer UV/VIS Spectrometer Lambda 20, UV at an appropriate wavelength for detection of the pharmacologically active ingredient present therein. Sample time points preferably include 0.5 and 1 hour.

Preferably, when comparing the in vitro release profile at 37° C. in simulated gastric fluid with the in vitro release profile in ethanol/simulated gastric fluid (40 vol.-%) at 37° C., the in vitro release in ethanol/simulated gastric fluid (40 vol.-%) is preferably not substantially accelerated compared to the in vitro release in simulated gastric fluid. Preferably, in this regard "substantially" means that at any given time point the in vitro release in ethanol/simulated gastric fluid (40 vol.-%) relatively deviates from the in vitro release in simulated gastric fluid by not more than +25%, more preferably not more than +20%, still more preferably not more than +15%, yet more preferably not more than +10%, even more preferably not more than +7.5%, most preferably not more than +5.0% and in particular not more than +2.5%.

A substantial relative acceleration of the in vitro release in ethanol/simulated gastric fluid (40 vol.-%) compared to the in vitro release in simulated gastric fluid is to be prevented according to the invention. However, a substantial relative deceleration of the in vitro release in ethanol/simulated gastric fluid (40 vol.-%) compared to the in vitro release in simulated gastric fluid, e.g., a relative deviation by −25% or more, may be possible and can even be desirable.

In a preferred embodiment, the pharmaceutical dosage form according to the invention contains no further pharmacologically active ingredient and/or wherein the total amount of the pharmacologically active ingredient that is contained in the pharmaceutical dosage form is contained in the one or more particles In another preferred embodiment, the pharmaceutical dosage form according to the invention contains a further pharmacologically active ingredient. In a preferred embodiment, the further pharmacologically active ingredient exhibits no psychotropic action. In another preferred embodiment, the further pharmacologically active ingredient is selected from ATC classes [M01A], [M01C], [N02B] and [N02C] according to the WHO.

In a particularly preferred embodiment,
(i) the pharmacologically active ingredient has a psychotropic effect; and/or
(ii) the further pharmacologically active ingredient is selected from ATC classes [M01A], [M01C], [N02B] and [N02C] according to the WHO.

Preferably, the further pharmacologically active ingredient is selected from the group consisting of acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, phenazone, metamizole sodium, aminophenazone, propyphenazone, nifenazone, paracetamol, phenacetin, bucetin, propacetamol, rimazolium, glafenine, floctafenine, viminol, nefopam, flupirtine, ziconotide, methoxyflurane, nabiximols, dihydroergotamine, ergotamine, methysergide, lisuride, flumedroxone, sumatriptan, naratriptan, zolmitriptan, rizatriptan, almotriptan, eletriptan, frovatriptan, pizotifen, clonidine, iprazochrome, dimetotiazine, oxetorone, phenylbutazone, mofebutazone, oxyphenbutazone, clofezone, kebuzone, indomethacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lomoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, naproxcinod, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, oxycinchophen, sodium aurothiomalate, sodium aurotiosulfate, auranofin, aurothioglucose, aurotioprol, penicillamine, bucillamine, their physiologically acceptable salts, as well as mixtures thereof.

In a preferred embodiment, the further pharmacologically active ingredient is paracetamol (acetaminophen) or ibuprofen, more preferably paracetamol.

Preferred combinations $C^1$ to $C^{32}$ of the pharmacologically active ingredient and the further pharmacologically active ingredient are summarized in the table here below, wherein the pharmacologically active ingredient as well as the further pharmacologically active ingredient each also refer to the physiologically acceptable salts thereof, particularly to the hydrochlorides:

|  | $A_1$ | $A_2$ |
| --- | --- | --- |
| $C^1$ | oxycodone | ibuprofen |
| $C^2$ | oxymorphone | ibuprofen |
| $C^3$ | hydrocodone | ibuprofen |
| $C^4$ | hydromorphone | ibuprofen |
| $C^5$ | morphine | ibuprofen |
| $C^6$ | tapentadol | ibuprofen |
| $C^7$ | tramadol | ibuprofen |
| $C^8$ | buprenorphine | ibuprofen |
| $C^9$ | oxycodone | paracetamol |
| $C^{10}$ | oxymorphone | paracetamol |
| $C^{11}$ | hydrocodone | paracetamol |
| $C^{12}$ | hydromorphone | paracetamol |
| $C^{13}$ | morphine | paracetamol |
| $C^{14}$ | tapentadol | paracetamol |
| $C^{15}$ | tramadol | paracetamol |
| $C^{16}$ | buprenorphine | paracetamol |
| $C^{17}$ | oxycodone | diclofenac |
| $C^{18}$ | oxymorphone | diclofenac |
| $C^{19}$ | hydrocodone | diclofenac |
| $C^{20}$ | hydromorphone | diclofenac |
| $C^{21}$ | morphine | diclofenac |
| $C^{22}$ | tapentadol | diclofenac |
| $C^{23}$ | tramadol | diclofenac |
| $C^{24}$ | buprenorphine | diclofenac |
| $C^{25}$ | oxycodone | acetylsalicylic acid |
| $C^{26}$ | oxymorphone | acetylsalicylic acid |
| $C^{27}$ | hydrocodone | acetylsalicylic acid |
| $C^{28}$ | hydromorphone | acetylsalicylic acid |
| $C^{29}$ | morphine | acetylsalicylic acid |
| $C^{30}$ | tapentadol | acetylsalicylic acid |
| $C^{31}$ | tramadol | acetylsalicylic acid |
| $C^{32}$ | buprenorphine | acetylsalicylic acid |

The further pharmacologically active ingredient is present in the pharmaceutical dosage form in a therapeutically effective amount. In general, the amount that constitutes a therapeutically effective amount varies according to the pharmacologically active ingredients being used, the condition being treated, the severity of said condition, the patient being treated, and whether the pharmaceutical dosage form is designed for an immediate or retarded release.

The total content of the further pharmacologically active ingredient preferably ranges from about 0.01 wt.-% to about 95 wt.-%, more preferably from about 0.1 wt.-% to about 80 wt.-%, even more preferably from about 1.0 wt.-% to about 50 wt.-%, yet more preferably from about 1.5 wt.-% to about 30 wt.-%, and most preferably from about 2.0 wt.-% to 20 wt.-%, based on the total weight of the pharmaceutical dosage form.

Preferably, the total content of the further pharmacologically active ingredient is within the range of from 0.01 to 80 wt.-%, more preferably 0.1 to 50 wt.-%, still more preferably 1 to 25 wt.-%, based on the total weight of the pharmaceutical dosage form. In a preferred embodiment, the total content of the further pharmacologically active ingredient is within the range of from 20±15 wt.-%, more preferably 20±12 wt.-%, still more preferably 20±10 wt.-%, most preferably 20±7 wt.-%, and in particular 20±5 wt.-%, based on the total weight of the pharmaceutical dosage form. In a preferred embodiment, the total content of the further pharmacologically active ingredient is within the range of from 30±15 wt.-%, more preferably 30±12 wt.-%, still more preferably 30±10 wt.-%, most preferably 30±7 wt.-%, and in particular 30±5 wt.-%, based on the total weight of the pharmaceutical dosage form. In a preferred embodiment, the total content of the further pharmacologically active ingredient is within the range of from 40±15 wt.-%, more preferably 40±12 wt.-%, still more preferably 40±10 wt.-%, most preferably 40±7 wt.-%, and in particular 40±5 wt.-%, based on the total weight of the pharmaceutical dosage form. In a preferred embodiment, the total content of the further pharmacologically active ingredient is within the range of from 50±15 wt.-%, more preferably 50±12 wt.-%, still more preferably 50±10 wt.-%, most preferably 50±7 wt.-%, and in particular 50±5 wt.-%, based on the total weight of the pharmaceutical dosage form. In a preferred embodiment, the total content of the further pharmacologically active ingredient is within the range of from 60±15 wt.-%, more preferably 60±12 wt.-%, still more preferably 60±10 wt.-%, most preferably 60±7 wt.-%, and in particular 60±5 wt.-%, based on the total weight of the pharmaceutical dosage form.

The total amount of the further pharmacologically active ingredient in the pharmaceutical dosage form, respectively, is not limited. The total amount of the further pharmacologically active ingredient which is adapted for administration preferably is in the range of 0.1 mg to 2,000 mg or 0.1 mg to 1,000 mg or 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the further pharmacologically active ingredient which is contained in the pharmaceutical dosage form, respectively, is within the range of from 10 to 1,000 mg, more preferably 50 to 900 mg, still more preferably 100 to 800 mg, yet more preferably 200 to 600 mg, most preferably 250 to 500 mg and in particular 300 to 400 mg. In another preferred embodiment, the total amount of the further pharmacologically active ingredient which is contained in the pharmaceutical dosage form, respectively, is within the range of from 10 to 500 mg, more preferably 12 to 450 mg, still more preferably 14 to 400 mg, yet more preferably 16 to 350 mg, most preferably 18 to 325 mg and in particular 20 to 300 mg.

In a preferred embodiment, the further pharmacologically active ingredient is contained in the further excipient(s) and the pharmaceutical dosage form, respectively, in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, or 250±5 mg. In another preferred embodiment, the further pharmacologically active ingredient is contained in the pharmaceutical dosage form, respectively, in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, or 250±2.5 mg. In still another preferred embodiment, the further pharmacologically active ingredient is contained in the pharmaceutical dosage form, respectively, in an amount of 250±10 mg, 275±10 mg, 300±10 mg, 325±10 mg, 350±10 mg, 375±10 mg, 400±10 mg, 425±10 mg, 450±10 mg, 475±10 mg, 500±10 mg, 525±10 mg, 550±10 mg, 575±10 mg or 600±10 mg.

In a particularly preferred embodiment, the further pharmacologically active ingredient is paracetamol (acetaminophen). In this embodiment, the paracetamol is preferably contained in the pharmaceutical dosage form in an amount of from 100 to 600 mg, more preferably 150 to 550 mg, still more preferably 200 to 500 mg, most preferably 250 to 450 mg and in particular 275 to 400 mg.

In another particularly preferred embodiment, the further pharmacologically active ingredient is ibuprofen. In this embodiment, the ibuprofen is preferably contained in the pharmaceutical dosage form in an amount of from 100 to 600 mg, more preferably 150 to 550 mg, still more preferably 200 to 500 mg, most preferably 250 to 450 mg and in particular 275 to 400 mg.

In a preferred embodiment, the relative weight ratio of the total content of the pharmacologically active ingredient to the total content of the further pharmacologically active ingredient is within the range of (8±1): 1, more preferably (7±1): 1, still more preferably (6±1):1, yet more preferably (5±1):1, even more preferably (4±1):1, most preferably (3±1):1 and in particular (2±1):1.

In still another preferred embodiment, the relative weight ratio of the total content of the further pharmacologically active ingredient to the total content of the pharmacologically active ingredient is within the range of (8±1): 1, more preferably (7±1): 1, still more preferably (6±1):1, yet more preferably (5±1):1, even more preferably (4±1):1, most preferably (3±1):1 and in particular (2±1):1.

Preferably, the pharmaceutical dosage form provides immediate release of the further pharmacologically active ingredient.

Preferably, under physiological conditions the pharmaceutical dosage form has released after minutes at least 10%, after 10 minutes at least 20%, after 15 minutes at least 30%, after 20 minutes at least 40%, after 30 minutes at least 60%, after 40 minutes at least 70%, after 50 minutes at least 80%, after 60 minutes at least 90% or 99% of the further pharmacologically active ingredient.

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 600 mL simulated intestinal fluid pH 6.8 (phosphate buffer) or pH 4.5. In a preferred embodiment, the rotational speed of the paddle is increased to 75 rpm. In another embodiment, the release profile is determined under the following conditions: basket method, 75 rpm, 37±5° C., 600 mL 0.1 N HCl or 600 mL of SIF sp (pH 6.8) or 600 mL of 0.1 N HCl+40% ethanol.

In a particularly preferred embodiment; under in vitro conditions in 600 mL 0.1 N HCl, using the basket method according to Ph. Eur. at 75 rpm, after 1 h under physiological conditions the pharmaceutical dosage form has released at least 60% more preferably at least 65%, still more preferably at least 70%, yet more preferably at least 75%, even more preferably at least 80%, most preferably at least 85% and in particular at least 90% or at least 95% or at least 99% of the further pharmacologically active ingredient relative to the total amount of $A_2$ originally contained in the pharmaceutical dosage form.

Besides the one or more particles containing pharmacologically active ingredient and physiologically acceptable polymer, the pharmaceutical dosage form typically contains further excipient(s) outside the one or more particles such as capsule material and/or other additives.

Preferably, the content of the further excipient(s) is at least 2.5 wt.-%, at least 5 wt.-%, at least 7.5 wt.-% or at least 10 wt.-%; at least 12.5 wt.-%, at least 15 wt.-%, at least 17.5 wt.-% or at least 20 wt.-%; at least 22.5 wt.-%, at least 25 wt.-%, at least 27.5 wt.-% or at least 30 wt.-%; at least 32.5 wt.-%, at least 35 wt.-%, at least 37.5 wt.-% or at least 40 wt.-%; more preferably at least 42.5 wt.-%, at least 45 wt.-%, at least 47.5 wt.-% or at least 50 wt.-%; still more preferably at least 52.5 wt.-%, at least 55 wt.-%, at least 57.5 wt.-% or at least 60 wt.-%; yet more preferably at least 62.5 wt.-%, at least 65 wt.-%, at least 67.5 wt.-% or at least 60 wt.-%; most preferably at least 72.5 wt.-%, at least 75 wt.-%, at least 77.5 wt.-% or at least 70 wt.-%; and in particular at least 82.5 wt.-%, at least 85 wt.-%, at least 87.5 wt.-% or at least 90 wt.-%; based on the total weight of the pharmaceutical dosage form.

Preferably, the content of the further excipient(s) is at most 90 wt.-%, at most 87.5 wt.-%, at most 85 wt.-%, or at most 82.5 wt.-%; more preferably at most 80 wt.-%, at most 77.5 wt.-%, at most 75 wt.-% or at most 72.5 wt.-%; still more preferably at most 70 wt.-%, at most 67.5 wt.-%, at most 65 wt.-% or at most 62.5 wt.-%; yet more preferably at most 60 wt.-%, at most 57.5 wt.-%, at most 55 wt.-% or at most 52.5 wt.-%; most preferably at most 50 wt.-%, at most 47.5 wt.-%, at most 45 wt.-% or at most 42.5 wt.-%; and in particular at most 40 wt.-%, at most 37.5 wt.-%, or at most 35 wt.-%; based on the total weight of the pharmaceutical dosage form.

Preferably, the relative weight ratio of the one or more particles to the further excipient(s) in the pharmaceutical dosage form is from 1:10 to 10:1, more preferably 1:8 to 8:1, still more preferably 1:7 to 6:1, even more preferably 1:6 to 5:1, yet more preferably 1:5 to 4:1, most preferably 1:4 to 3:1 and in particular 1:3 to 2:1 or 1:2 to 1:1, based on the total weight of the one or more particles and on the total weight of the further excipient(s).

The further excipient(s) may optionally comprise conventional pharmaceutical excipients.

Preferably, the further excipient(s) comprise(s) one or more fillers or binders. As many fillers can be regarded as binders and vice versa, for the purpose of the specification "filler/binder" refers to any excipient that is suitable as filler, binder or both. Thus, the further excipient(s) preferably comprise(s) a filler/binder.

Preferred fillers (=filler/binders) are selected from the group consisting of silicium dioxide (e.g. Aerosil®), microcrystalline cellulose (e.g. Avicel®, Elcema®, Emocel®, ExCel®, Vitacell®); cellulose ether (e.g. Natrosol®, Klucel®, Methocel®, Blanose®, Pharmacoat®, Viscontran®); mannitol; dextrines; dextrose; calciumhydrogen phosphate (e.g. Emcompress®); tricalcium phosphate, maltodextrine (e.g. Emdex®); lactose (e.g. Fast-Flow Lactose®; Ludipress®. Pharmaceutical dosage Formtose®, Zeparox®); polyvinylpyrrolidone (PVP) (e.g. Kollidone®, Polyplasdone®, Polydone®); saccharose (e.g. Nu-Tab®, Sugar Tab®); magnesium salts (e.g. $MgCO_3$, MgO, $MgSiO_3$); starches and pretreated starches (e.g. Prejel®, Primotab® ET, Starch® 1500). Preferred binders are selected from the group consisting of alginates; chitosanes; and any of the fillers mentioned above (=fillers/binders).

Some fillers/binders may also serve other purposes. It is known, for example, that silicium dioxide exhibits excellent function as a glidant. Preferably, the further excipient(s) comprise(s) a glidant such as silicium dioxide.

In a preferred embodiment, the content of the filler/binder or mixture of fillers/binders in the further excipient(s) is within the range of 50±25 wt.-%, more preferably 50±20 wt.-%, still more preferably 50±15 wt.-%, yet more preferably 50±10 wt.-%, most preferably 50±7.5 wt.-%, and in particular 50±5 wt.-%, based on the total weight of further excipient(s). In another preferred embodiment, the content of the filler/binder or mixture of fillers/binders in the further excipient(s) is within the range of 65±25 wt.-%, more preferably 65±20 wt.-%, still more preferably 65±15 wt.-%, yet more preferably 65±10 wt.-%, most preferably 65±7.5 wt.-%, and in particular 65±5 wt.-%, based on the total weight of further excipient(s). In still another preferred embodiment, the content of the filler/binder or mixture of fillers/binders in further excipient(s) is within the range of 80±19 wt.-%, more preferably 80±17.5 wt.-%, still more preferably 80±15 wt.-%, yet more preferably 80±10 wt.-%, most preferably 80±7.5 wt.-%, and in particular 80±5 wt.-%, based on the total weight of further excipient(s). In another preferred embodiment, the content of the filler/binder or mixture of fillers/binders in the further excipient(s) is within the range of 90±9 wt.-%, more preferably 90±8 wt.-%, still more preferably 90±7 wt.-%, yet more preferably 90±6 wt.-%, most preferably 90±5 wt.-%, and in particular 90±4 wt.-%, based on the total weight of further excipient(s).

In a preferred embodiment, the total content of the filler/binder or mixture of fillers/binders in the pharmaceutical dosage form is within the range of 25±24 wt.-%, more preferably 25±20 wt.-%, still more preferably 25±16 wt.-%, yet more preferably 25±12 wt.-%, most preferably 25±8 wt.-%, and in particular 25±4 wt.-%, based on the total weight of pharmaceutical dosage form. In another preferred embodiment, the total content of the filler/binder or mixture of fillers/binders in the pharmaceutical dosage form is within the range of 30±29 wt.-%, more preferably 30±25 wt.-%, still more preferably 30±20 wt.-%, yet more preferably 30±15 wt.-%, most preferably 30±10 wt.-%, and in particular 30±5 wt.-%, based on the total weight of pharmaceutical dosage form. In still another preferred embodiment, the total content of the filler/binder or mixture of fillers/binders in the pharmaceutical dosage form is within the range of 35±34 wt.-%, more preferably 35±28 wt.-%, still more preferably 35±22 wt.-%, yet more preferably 35±16 wt.-%, most preferably 35±10 wt.-%, and in particular 35±4 wt.-%, based on the total weight of pharmaceutical dosage form. In another preferred embodiment, the total content of the filler/binder or mixture of fillers/binders in the pharmaceutical dosage form is within the range of 40±39 wt.-%, more preferably 40±32 wt.-%, still more preferably 40±25 wt.-%, yet more preferably 40±18 wt.-%, most preferably 40±11 wt.-%, and in particular 40±4 wt.-%, based on the total weight of pharmaceutical dosage form.

Preferably, the filler/binder is contained in the further excipient(s) but not in the one or more particles of the pharmaceutical dosage form according to the invention.

Preferably, the further excipient(s) comprise(s) one or more diluents or lubricants, preferably selected from the group consisting of calcium stearate; magnesium stearate; glycerol monobehenate (e.g. Compritol®); Myvatex®; Precirol®; Precirol® Ato5; sodium stearylfumarate (e.g. Pruv®); and talcum. Magnesium stearate is particularly preferred. Preferably, the content of the lubricant in the further excipient(s) is at most 10.0 wt.-%, more preferably at most 7.5 wt.-%, still more preferably at most 5.0 wt.-%, yet more preferably at most 2.0 wt.-%, even more preferably at most 1.0 wt.-%, and most preferably at most 0.5 wt.-%, based on the total weight of the further excipient(s) or based on the total weight of pharmaceutical dosage form.

Preferably, the further excipient(s) comprise(s) one or more disintegrants, preferably selected from the group consisting of carmellose and salts thereof, croscarmellose sodium, crospovidone, sodium carboxymethyl starch, sodium starch glycolate, partly pregelatinized starch and low-substituted hydroxypropyl cellulose. Crosscarmellose is particularly preferred. Preferably, the content of the disintegrant in the further excipient(s) is at most 20.0 wt.-%, more preferably at most 15 wt.-%, still more preferably at most 12.5 wt.-%, yet more preferably at most 10 wt.-%, even more preferably at most 8.0 wt.-%, and most preferably within the range of from 6.0 wt.-% to 8.0 wt.-%, based on the total weight of the further excipient(s) or based on the total weight of pharmaceutical dosage form.

Preferably, the further excipient(s) comprise(s) one or more dispersing agents or a wetting agents, preferably selected from the group consisting of poloxamers such as Lutrol F68. Preferably, the content of the dispersing agent or a wetting agent in the further excipient(s) is at most 50 wt.-%, more preferably at most 45 wt.-%, still more preferably at most 40 wt.-%, yet more preferably at most 35 wt.-%, even more preferably at most 30 wt.-%, and most preferably within at most 30 wt.-%, based on the total weight of the further excipient(s) or based on the total weight of pharmaceutical dosage form.

In particularly preferred embodiment, the further excipient(s) comprise(s) a combination of filler/binder and lubricant and optionally disintegrant and optionally dispersing agent/wetting agent.

The further excipient(s) of the pharmaceutical dosage form according to the invention may additionally contain other excipients that are conventional in the art, e.g. diluents, binders, granulating aids, colorants, flavourants, glidants, wet-regulating agents and disintegrants. The skilled person will readily be able to determine appropriate quantities of each of these excipients.

In a preferred embodiment, however, besides the further pharmacologically active ingredient, the further excipient(s) of the pharmaceutical dosage form according to the invention consists of one or more disintegrants, one or more filler/binder's and one or more lubricants, but does not contain any other constituents.

In a particularly preferred embodiment, the further excipient(s) of the pharmaceutical dosage form according to the invention do(es) not contain one or more gel-forming agents and/or a silicone.

In a preferred embodiment, the further excipient(s) of the pharmaceutical dosage form according to the invention do(es) not contain polyalkylene oxides, acrylic polymers or waxy materials. If the further excipient(s) contain(s) polyalkylene oxides, acrylic polymers and/or waxy materials, the total content of polyalkylene oxides, acrylic polymers and waxy materials preferably is not more than 30 wt.-%, more preferably not more than 25 wt.-%, still more preferably not more than 20 wt.-%, yet more preferably not more than 15 wt.-%, even more preferably not more than 10 wt.-%, most preferably not more than 5.0 wt.-%, and in particular not more than 1.0 wt.-%, relative to the total weight of the further excipient(s).

As used herein the term "gel-forming agent" is used to refer to a compound that, upon contact with a solvent (e.g. water), absorbs the solvent and swells, thereby forming a viscous or semi-viscous substance. Preferred gel-forming agents are not cross-linked. This substance may moderate pharmacologically active ingredient release from the embedded particulates in both aqueous and aqueous alcoholic media. Upon full hydration, a thick viscous solution or dispersion is typically produced that significantly reduces and/or minimizes the amount of free solvent which can contain an amount of solubilized pharmacologically active ingredient, and which can be drawn into a syringe. The gel that is formed may also reduce the overall amount of pharmacologically active ingredient extractable with the solvent by entrapping the pharmacologically active ingredient within a gel structure. Thus the gel-forming agent may play an important role in conferring tamper-resistance to the pharmaceutical dosage forms according to the invention.

Gel-forming agents that preferably are not contained in the further excipient(s) include pharmaceutically acceptable polymers, typically hydrophilic polymers, such as hydrogels. Representative examples of gel-forming agent include polyalkylene oxide such as polyethylene oxide, polyvinyl alcohol, hydroxypropylmethyl cellulose, carbomers, poly (uronic) acids and mixtures thereof.

The optional excipients preferably do not impart to the further excipient(s) any significant resistance against dose-dumping in aqueous ethanol. According to this embodiment, the further excipient(s) preferably do(es) not contain any compound which would impart to the further excipient(s) any substantial resistance against dose-dumping in aqueous ethanol such as polyalkylene oxides, nonionic acrylic polymers or waxy materials.

The one or more particles containing pharmacologically active ingredient and physiologically acceptable polymer may be incorporated in an outer matrix material formed by the further excipient(s). From a macroscopic perspective, the outer matrix material formed by the further excipient(s) preferably forms a continuous phase in which the one or more particles is/are embedded. Preferably, the one or more particles containing pharmacologically active ingredient and physiologically acceptable polymer form a discontinuous phase within an outer matrix material that is formed by further excipient(s).

For the purpose of definition, the "outer matrix material" is preferably the further excipient(s) and thus, preferably comprises the optionally present further pharmacologically active ingredient and optionally present conventional pharmaceutical excipients which have already been described above.

In a preferred embodiment, the further excipient(s) essentially consist(s) of the further pharmacologically active ingredient, i.e. the further excipient(s) do(es) not comprise any pharmaceutical excipient. According to this embodiment, the pharmaceutical dosage form is preferably a capsule that is filled with the one or more particles and the further pharmacologically active ingredient, which may be powdery or agglomerated, e.g. granulated, and which preferably forms a further excipient(s) as an outer matrix material.

Preferably, the outer matrix material is a homogenous powdery or coherent mass, preferably a homogeneous mixture of solid constituents, in which the one or more particles are embedded. According to this embodiment, the one or more particles containing pharmacologically active ingredient and physiologically acceptable polymer are preferably spatially separated from one another. While it is possible that the surfaces of particles containing pharmacologically active ingredient and physiologically acceptable polymer are in contact or at least in very close proximity with one another, the plurality of particles containing pharmacologically active ingredient and physiologically acceptable polymer preferably cannot be regarded as a single continuous coherent mass within the pharmaceutical dosage form.

In other words, when the particles containing pharmacologically active ingredient and physiologically acceptable polymer are contained in an outer matrix material formed by the further excipient(s), the pharmaceutical dosage form according to the invention preferably comprises the one or more particles as volume elements of a first type and the outer matrix material formed by the further excipient(s) as volume element of a second type differing from the material that forms the particles of the one or more particles, and preferably containing no prolonged release matrix.

When the one or more particles are contained in an outer matrix material formed by the further excipient(s), the relative weight ratio of the one or more particles to the outer matrix material is not particularly limited. Preferably, said relative weight ratio is within the range of 1:2.00±1.75, more preferably 1:2.00±1.50, still more preferably 1:1.00±1.00, most preferably 1:1.00±0.75, and in particular 1:1.00±0.50.

The further excipient(s) in turn may also be in particulate form. When the further excipient(s) is particulate form, however, the particles are preferably not thermoformed and preferably do not contain physiologically acceptable polymer. When the further excipient(s) is in particulate form, the particles are preferably obtained by conventional methods for the preparation of aggregates and agglomerates from powder mixtures such as granulating and compacting.

Preferably, the breaking strength of the pharmaceutical dosage form is below the breaking strength of the one or more particles containing pharmacologically active ingredient and physiologically acceptable polymer.

When the further excipients are not present as free-flowing powder but as constituents of a compacted, granulated, congealed or otherwise agglomerated material, the breaking strength of such material containing the further excipient(s) can be determined. Preferably, the further excipient(s) exhibit(s) a breaking strength that is lower than that of one or more particles containing pharmacologically active ingredient and physiologically acceptable polymer. Typically, the breaking strength of further excipient(s) is not increased compared to the breaking strength of conventional dosage forms, i.e. well below 200 N. When the further excipient(s) are powdery, the "breaking strength" of the powder is so low that it cannot be measured by conventional means. Thus, for the purpose of specification, the breaking strength of the powder should be regarded as "0 Newton". When quantifying the breaking strength of the further excipient(s) by "0 Newton", the further excipient(s) is/are typically present in form of a (free-flowing) powder, and when quantifying the breaking strength of the further excipient(s) by values above "0 Newton", this implies that according to these embodiments the further excipient(s) is/are at least to some minimal degree present in form of granulated, compacted, congealed or otherwise agglomerated matter, but not as a (free-flowing) powder.

When the further excipient(s) are contained in the material of a capsule that is filled with the one or more particles containing pharmacologically active ingredient and physiologically acceptable polymer, the breaking strength of the excipient(s) is to be regarded as the breaking strength of the capsule, regardless of whether the filling of the capsule comprises additional excipients or not.

In a preferred embodiment, the further excipient(s) exhibit(s) a breaking strength within the range of from 0 N to at most 500 N. Preferably, the further excipient(s) exhibit(s) a breaking strength within the range of from 0 N to 450 N, more preferably 0 N to 400 N, still more preferably 0 N to 350 N, yet more preferably 0 N to 300 N, most preferably 0 N to 250 N and in particular 0 N to 200 N.

Preferably, the at least one or more particles containing pharmacologically active ingredient and physiologically acceptable polymer exhibit a higher breaking strength than the further excipient(s) of the pharmaceutical dosage form.

Preferably, the breaking strength of the one or more particles containing pharmacologically active ingredient and physiologically acceptable polymer is relatively at least 50 N higher, more preferably at least 100 N higher, still more preferably at least 150 N higher, yet more preferably at least 200 N higher, even more preferably at least 250 N higher, most preferably at least 300 N higher, and in particular at least 350 N higher than the breaking strength of the further excipient(s).

In a preferred embodiment,
(i) the one or more particles containing pharmacologically active ingredient and physiologically acceptable polymer exhibits a breaking strength of at least 300 N, more preferably at least 400 N, still more preferably more than 500 N, yet more preferably at least 750 N, even more preferably at least 1000 N, most preferably at least 1250 N, and in particular at least 1500 N; and/or
(ii) the further excipient(s) exhibit(s) a breaking strength of at most 500 N, more preferably at most 300 N, still more preferably at most 250 N, yet more preferably at most 200 N, even more preferably at most 150 N, most preferably at most 100 N, and in particular at most 50 N.

Because of the different breaking strength of the one or more particles containing pharmacologically active ingredient and physiologically acceptable polymer and the further excipient(s), when measuring the breaking strength of the pharmaceutical dosage form according to the invention, a distance-to-force diagram can be obtained that contains at least two steps; the first platform in the distance-to-force diagram is reached once the further excipient(s) fracture and the second platform in the distance-to-force diagram is reached once the one or more particles containing pharmacologically active ingredient and physiologically acceptable polymer fracture. When the further excipient(s) is present in powdery form, however, the "first platform" corresponds to the baseline, i.e. is not visible. Furthermore, depending upon the upper measuring limit of the breaking strength tester, the one or more particles containing pharmacologically active ingredient and physiologically acceptable polymer might not have fractured once said upper limit is reached.

In a preferred embodiment, the one or more particles containing pharmacologically active ingredient and physiologically acceptable polymer exhibit a higher breaking strength than the overall pharmaceutical dosage form comprising the one or more particles and optionally, further excipient(s). According to this embodiment, the breaking strength of the pharmaceutical dosage form is preferably defined as the amount of force that is necessary in order to fracture a pharmaceutical dosage form into two or more fragments, wherein said fragments preferably contain the still intact one or more particles.

Preferably, the breaking strength of the one or more particles is relatively at least 50 N higher, more preferably at least 100 N higher, still more preferably at least 150 N higher, yet more preferably at least 200 N higher, even more preferably at least 250 N higher, most preferably at least 300 N higher, and in particular at least 350 N higher than the breaking strength of the pharmaceutical dosage form comprising the one or more particles and optionally, further excipient(s).

Another aspect of the invention relates to a process for the production of a pharmaceutical dosage form comprising the steps of
(i) thermoforming one or more particles comprising a pharmacologically active ingredient and a natural or synthetic physiologically acceptable polymer;
(ii) providing at least one further excipient(s) comprising a further pharmacologically active ingredient; and
(iii) combining the at least one one or more particles, the at least one further excipient(s).

In a preferred embodiment, the one or more particles containing pharmacologically active ingredient and physiologically acceptable polymer are thermoformed. According to this embodiment, the one or more particles are preferably melt-extruded.

Thermoforming preferably means that in the course of the manufacture of the one or more particles the mass is heated to a temperature above ambient temperature, preferably to at least 30° C., at least 40° C., at least 50° C., at least 60° C., at least 70° C., or at least 80° C., and compressed, preferably at pressures that are sufficient to yield a coherent, not dripping form, preferably at pressures of at least 10 bar or at least 30 bar. The compression force may be exerted prior to, during or subsequent to application of heat.

The one or more particles are preferably thermoformed, preferably by melt-extrusion, although also other methods of thermoforming may be useful, such as press-molding at elevated temperature or heating of compacts that were manufactured by conventional compression in a first step and then heated above the softening temperature of the prolonged release matrix material in a second step to form break resistant, hardened compacts, i.e. particles. In this regard, thermoforming preferably means the forming, or molding of a mass after, before or during the application of heat. In a preferred embodiment, thermoforming is performed by hot-melt extrusion.

In a preferred embodiment, hot melt-extrusion is performed by means of a twin-screw-extruder. Melt extrusion preferably provides a melt-extruded strand that is preferably cut into monoliths, which are then optionally compressed and formed. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C.

The strands obtained by way of extrusion can either be subjected to the compression step as such or can be cut prior to the compression step. This cutting can be performed by usual techniques, for example using rotating knives or compressed air, at elevated temperature, e.g. when the extruded stand is still warm due to hot-melt extrusion, or at ambient temperature, i.e. after the extruded strand has been allowed to cool down. When the extruded strand is still warm, singulation of the extruded strand into extruded monoliths and particles, respectively, is preferably performed by cutting the extruded strand immediately after it has exited the extrusion die.

However, when the extruded strand is cut in the cooled state, subsequent singulation of the extruded strand is preferably performed by optionally transporting the still hot extruded strand by means of conveyor belts, allowing it to cool down and to congeal, and subsequently cutting it.

Alternatively, the shaping can take place as described in EP-A 240 906 by the extrudate being passed between two counter-rotating calender rolls and being shaped directly to the one or more particles. It is of course also possible to subject the extruded strands to the compression step or to the cutting step when still warm, that is more or less immediately after the extrusion step. The extrusion is preferably carried out by means of a twin-screw extruder.

The preferably monolithic or particulate one or more particles according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In general, the process for the production of one or more particles containing pharmacologically active ingredient and physiologically acceptable polymer according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the preferably prolonged release matrix material, preferably the physiologically acceptable polymer, up to its softening point;
(c) hardening the mixture by applying heat and force, it being possible to supply the heat during and/or before and/or after the application of force and the quantity of heat supplied being sufficient to heat the preferably prolonged release matrix material, preferably the physiologically acceptable polymer, at least up to its softening point; and thereafter allowing the material to cool and removing the force; and
(d) optionally singulating the hardened mixture.

Heat may be supplied directly, e.g. by contact or by means of hot gas such as hot air, or with the assistance of ultrasound; or is indirectly supplied by friction and/or shear. Force may be applied and/or the monoliths or particles may be shaped for example by direct forming or with the assistance of a suitable extruder, particularly by means of a screw extruder equipped with one or two screws (single-screw-extruder and twin-screw-extruder, respectively) or by means of a planetary gear extruder.

The final shape of the particles may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the prolonged release matrix material. However, extrusion at lower temperatures, e.g. ambient temperature, is also possible and may be preferred.

A particularly preferred process for the manufacture of the one or more particles containing pharmacologically active ingredient and physiologically acceptable polymer according to the invention involves hot-melt extrusion. In this process, the one or more particles are produced by thermoforming with the assistance of an extruder, preferably without there being any observable consequent discoloration of the extrudate.

This process is preferably characterized in that
a) all components are mixed,
b) the resultant mixture is heated in the extruder at least up to the softening point of the prolonged release matrix material, preferably the physiologically acceptable polymer, and extruded through the outlet orifice of the extruder by application of force, and
c) the still plastic extrudate is singulated and formed into the monoliths or particles of the one or more particles.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of prolonged release matrix material is extruded from the extruder through a die with at least one bore.

The hot-melt extrusion process according to the invention requires the use of suitable extruders, preferably screw extruders. Screw extruders which are equipped with two screws (twin-screw-extruders) are particularly preferred.

In a preferred embodiment, extrusion is performed in the absence of water, i.e., no water is added. However, traces of water (e.g., caused by atmospheric humidity) may be present.

In another preferred embodiment, particularly when the prolonged release matrix material is employed in the form of an aqueous dispersion, extrusion is performed in the presence of water and the water is evaporated from the extruded material in the course of the extrusion process, i.e. preferably before the extruded material exits the outlet orifice of the extruder. Therefore a vacuum pump mechanism is used to extract the (evaporated) water from the extruded material. Thus, the extruded strand is preferably water-free, which preferably means that the water content of the extruded strand is preferably at most 10 wt.-%, or at most 7.5 wt.-%, or at most 5.0 wt.-%, or at most 4.0 wt.-%, or at most 3.0 wt.-%, or at most 2.0 wt.-%, more preferably at most 1.7 wt.-%, still more preferably at most 1.5 wt.-%, yet more preferably at most 1.3 wt.-%, even more preferably at most 1.0 wt.-%, most preferably at most 0.7 wt.-%, and in particular at most 0.5 wt.-%. For that purpose, extrusion is preferably performed at a temperature above the boiling point of water under the given conditions; when extrusion is performed under vacuum, the boiling point of water may be substantially below 100° C. However, even if extrusion is performed under vacuum the preferred extrusion temperature is above 100° C.

The extruder preferably comprises at least two temperature zones, with heating of the mixture at least up to the softening point of the prolonged release matrix material proceeding in the first zone, which is downstream from a feed zone and optionally mixing zone. The throughput of the mixture is preferably from 1.0 kg to 15 kg/hour. In a preferred embodiment, the throughput is from 0.2 kg/hour to 3.5 kg/hour. In another preferred embodiment, the throughput is from 4 to 15 kg/hour.

In a preferred embodiment, the die head pressure is within the range of from 0.5 to 200 bar. The die head pressure can be adjusted inter alia by die geometry, temperature profile, extrusion speed, number of bores in the dies, screw configuration, first feeding steps in the extruder, and the like.

In a preferred embodiment, the die head pressure is within the range of from 20±19 bar, more preferably 20±15 bar, and in particular 20±10 bar; or the die head pressure is within the range of from 30±20 bar, more preferably 30±15 bar, and in particular 30±10 bar; or the die head pressure is within the range of from 40±20 bar, more preferably 40±15 bar, and in particular 40±10 bar; or the die head pressure is within the range of from 50±20 bar, more preferably 50±15 bar, and in particular 50±10 bar; or the die head pressure is within the range of from 60±20 bar, more preferably 60±15 bar, and in particular 60±10 bar; or the die head pressure is within the range of from 70±20 bar, more preferably 70±15 bar, and in particular 70±10 bar; or the die head pressure is within the range of from 80±20 bar, more preferably 80±15 bar, and in particular 80±10 bar; or the die head pressure is within the range of from 90±20 bar, more preferably 90±15 bar, and in particular 90±10 bar; or the die head pressure is within the range of from 100±20 bar, more preferably 100±15 bar, and in particular 100±10 bar.

The die geometry or the geometry of the bores is freely selectable. The die or the bores may accordingly exhibit a flat (film), round, oblong or oval cross-section, wherein the round cross-section preferably has a diameter of 0.1 mm to 2 mm for extruded particles and a larger diameter for extruded monolithic pharmaceutical dosage forms. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the prolonged release matrix material and does not rise above a temperature at which the pharmacologically active ingredient to be processed may be damaged. Preferably, the temperature of the mixture to be extruded is adjusted to below 180° C., preferably below 150° C., but at least to the softening temperature of prolonged release matrix material. Typical extrusion temperatures are 120° C. and 150° C.

In a preferred embodiment, the extruder torque is within the range of from 30 to 95%. Extruder torque can be adjusted inter alia by die geometry, temperature profile, extrusion speed, number of bores in the dies, screw configuration, first feeding steps in the extruder, and the like.

After extrusion of the molten mixture and optional cooling of the extruded strand or extruded strands, the extrudates are preferably singulated. This singulation may preferably be performed by cutting up the extrudates by means of revolving or rotating knives, wires, blades or with the assistance of laser cutters.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nürnberg, Germany), screw diameters of 18 or 27 mm. Screws having eccentric or blunt ends may be used. A heatable die with a round bore or with a multitude of bores each having a diameter of 0.2, 0.3, 0.4, 0.5, 0.6, 0.7, 0.8, 0.9, 1.0, 2.0, 3.0, 4.0, 5.0 or 0.6 mm may be used. The extrusion parameters may be adjusted e.g. to the following values: rotational speed of the screws: 120 Upm; delivery rate 2 kg/h for a ZSE 18 or 8 kg/h for a ZSE27; product temperature: in front of die 125° C. and behind die 135° C.; and jacket temperature: 110° C. Another suitable extruder that is equipped with a vacuum pump is a Thermo Scientific* Pharma 16 HME hot melt twin-screw extruder.

Preferably, extrusion is performed by means of twin-screw-extruders or planetary-gear-extruders, twin-screw extruders (co-rotating or contra-rotating) being particularly preferred.

The preferably monolithic or particulate one or more particles containing pharmacologically active ingredient and physiologically acceptable polymer according to the invention is preferably produced by thermoforming with the assistance of an extruder without any observable consequent discoloration of the extrudates.

The process for the preparation of the preferably monolithic or particulate one or more particles according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the one or more particles according to the invention can be regarded as "extruded pellet(s)". The term "extruded pellets" has structural implications which are understood by persons skilled in the art. A person skilled in the art knows that pelletized particles or pharmaceutical dosage forms can be prepared by a number of techniques, including:

drug layering on nonpareil sugar or microcrystalline cellulose beads,
spray drying,
spray congealing,
rotogranulation,
hot-melt extrusion,
spheronization of low melting materials, or
extrusion-spheronization of a wet mass.

Accordingly, "extruded pellets" can be obtained either by hot-melt extrusion or by extrusion-spheronization.

"Extruded pellets" can be distinguished from other types of pellets because they are structurally different. For example, drug layering on nonpareils yields multilayered pellets having a core, whereas extrusion typically yields a monolithic mass comprising a homogeneous mixture of all ingredients. Similarly, spray drying and spray congealing typically yield spheres, whereas extrusion typically yields cylindrical extrudates which can be subsequently spheronized.

The structural differences between "extruded pellets" and "agglomerated pellets" are significant because they may affect the release of active substances from the pellets and consequently result in different pharmacological profiles. Therefore, a person skilled in the pharmaceutical formulation art would not consider "extruded pellets" to be equivalent to "agglomerated pellets".

The pharmaceutical dosage forms according to the invention may be prepared from the one or more particles containing pharmacologically active ingredient and physiologically acceptable polymer and the further excipient(s) by any conventional method.

When the pharmaceutical dosage forms are prepared by compression, the one or more particles are preferably mixed, e.g. blended and/or granulated (e.g. wet granulated), with the material of the further excipient(s) as outer matrix material and the resulting mix (e.g. blend or granulate) is then either filled in capsules or compressed, preferably in molds, to form pharmaceutical dosage forms. It is also envisaged that the monoliths or particles herein described may be incorporated into a matrix using other processes, such as by melt granulation (e.g. using fatty alcohols and/or water-soluble waxes and/or water-insoluble waxes) or high shear granulation, followed by compression.

When the pharmaceutical dosage forms according to the invention are manufactured by means of an eccentric press, the compression force is preferably within the range of from 5 to 15 kN. When the pharmaceutical dosage forms according to the invention are manufactured by means of a rotating press, the compression force is preferably within the range of from 5 to 40 kN, in certain embodiments >25 kN, in other embodiments about 13 kN.

Another aspect of the invention relates to a pharmaceutical dosage for that is obtainable by any of the methods described above.

Examples of pharmaceutical dosage forms according to the invention include, but are not limited to, capsules, tablets, pills, granules, pellets, films, sachets, effervescent, powders, and the like.

In a preferred embodiment, the pharmaceutical dosage form is selected from the group consisting of capsules, sugar-coated tablets, dry-coated tablets, mantle tablets, and layered tablets.

In a particularly preferred embodiment of the invention, the composition is formulated in a capsule. In accordance with this embodiment, the pharmaceutical dosage form comprises a hard or soft gelatin capsule.

Most pharmaceutical dosage forms are intended to be swallowed whole and accordingly, preferred pharmaceutical dosage forms according to the invention are designed for oral administration. However, alternatively pharmaceutical dosage forms may be dissolved in the mouth, chewed, and some may be placed in a body cavity. Thus, the pharmaceutical dosage form according to the invention may alternatively be adapted for buccal, lingual, rectal or vaginal administration. Implants are also possible.

The pharmaceutical dosage form according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g. In a preferred embodiment, the total weight of the pharmaceutical dosage form is within the range of 600±450 mg, more preferably 600±300 mg, still more preferably 600±200 mg, yet more preferably 600±150 mg, most preferably 600±100 mg, and in particular 600±50 mg.

The total weight of the tamper-resistant pharmaceutical dosage form is greater than the total weight of the one or more particles containing pharmacologically active ingredient and physiologically acceptable polymer.

Preferably, the total weight of the pharmaceutical dosage form is at least 2 mg, or at least 5 mg, or at least 10 mg, or at least 15 mg, or at least 20 mg, or at least 25 mg; more preferably at least 30 mg, or at least 35 mg, or at least 40 mg, or at least 45 mg, or at least 50 mg; still more preferably at least 55 mg, or at least 60 mg, or at least 65 mg, or at least 70 mg, or at least 75 mg; yet more preferably at least 80 mg, or at least 85 mg, or at least 90 mg, or at least 95 mg, or at least 100 mg; even more preferably at least 105 mg, or at least 110 mg, or at least 115 mg, or at least 120 mg, or at least 125 mg; most preferably at least 130 mg, or at least 135 mg, or at least 140 mg, or at least 145 mg, or at least 150 mg, and in particular at least 155 mg, or at least 160 mg, or at least 165 mg, or at least 170 mg, or at least 175 mg greater than the total weight of the one or more particles containing pharmacologically active ingredient and physiologically acceptable polymer.

Preferably, the total volume of the pharmaceutical dosage form is greater than the total volume of the one or more particles containing pharmacologically active ingredient and physiologically acceptable polymer.

Preferably, the total volume of the pharmaceutical dosage form is greater by at least 1 vol.-% or at least 2 vol.-%, more preferably at least 3 vol.-% or at least 4 vol.-%, still more preferably at least 5 vol.-% or at least 6 vol.-%, yet more preferably at least 7 vol.-% or at least 8 vol.-%, even more preferably at least 9 vol.-% or at least 10 vol.-%, most preferably at least 11 vol.-% or at least 12 vol.-%, and in particular at least 13 vol.-% or at least 14 vol.-% than the total volume of the one or more particles containing pharmacologically active ingredient and physiologically acceptable polymer.

In a preferred embodiment, the pharmaceutical dosage form according to the invention is a capsule, more preferably a hard capsule and most preferably a hard gelatin capsule. Pharmaceutical dosage forms of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the pharmaceutical dosage form according to the invention is a round pharmaceutical dosage form. Pharmaceutical dosage forms of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

Preferably, the pharmaceutical dosage form according to the invention comprises n particles each containing pharmacologically active ingredient and physiologically acceptable polymer, wherein each of said n particles has a length within the range of $(10\pm7)/n$, more preferably $(10\pm6)/n$ mg, still more preferably $(10\pm5)/n$ mm yet more preferably $(10\pm4)/n/mm$ even more preferably $(10\pm3)/n$ mm most preferably $(10\pm2)/n$ mm, and in particular $(10\pm1)/n$ mm; wherein n is preferably 1, 2, 3, 4, 5, 6, 7, 8, 9 or 10.

In still another preferred embodiment, the pharmaceutical dosage form according to the invention is an oblong pharmaceutical dosage form. Pharmaceutical dosage forms of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

Preferably, the pharmaceutical dosage form according to the invention is not in form of a film.

The pharmaceutical dosage form according to the invention may optionally comprise a coating, e.g. a cosmetic coating. In a preferred embodiment, the coated pharmaceutical dosage form according to the invention is monolithic. The coating is preferably applied after formation of the pharmaceutical dosage form. The coating may be applied prior to or after the curing process. The pharmaceutical dosage forms according to the invention are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), poly(meth)-acrylates, such as aminoalkylmethacrylate copolymers, methacrylic acid methylmethacrylate copolymers, methacrylic acid methylmethacrylate copolymers; vinyl polymers, such as polyvinylpyrrolidone, polyvinyl alcohol, polyvinylacetate; and natural film formers.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5.

The coating can also be applied e.g. to improve the aesthetic impression and/or the taste of the pharmaceutical dosage forms and the ease with which they can be swallowed. Coating the pharmaceutical dosage forms according to the invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Coated pharmaceutical dosage forms according to the invention are preferably prepared by first making the cores and subsequently coating said cores using conventional techniques, such as coating in a coating pan.

Preferably, the coating does not contain the further pharmacologically active ingredient, more preferably the coating does not contain any pharmacologically active ingredient.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredients, preferably no antagonists against psychotropic substances, in particular no antagonists against opioids. Antagonists suitable for a given pharmacologically active ingredient are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredients, nor emetics, nor bitter substances.

Preferably, the one or more particles containing pharmacologically active ingredient and physiologically acceptable polymer, more preferably the entire pharmaceutical dosage form according to the invention contains more than 20 wt.-%, more preferably more than 30 wt.-%, still more preferably more than 40 wt.-%, yet more preferably more than 50 wt.-%, most preferably more than 60 wt.-%, and in particular more than 70 wt.-% of compounds which are not or hardly soluble in ethanol with respect to the total weight of the pharmaceutical dosage form.

For the purpose of specification, compounds which are not or hardly soluble in ethanol have a maximum solubility in aqueous ethanol (96%) at room temperature of preferably less than 1000 mg/L, more preferably less than 800 mg/L, even more preferably less than 500 mg/L, most preferably less than 100 mg/L and in particular less than 10 mg/L or less than 1 mg/L.

Preferably, the one or more particles containing pharmacologically active ingredient and physiologically acceptable polymer, more preferably the entire pharmaceutical dosage form according to the invention contains more than 50 wt.-%, more preferably more than 60 wt.-%, still more preferably more than 70 wt.-%, yet more preferably more than 80 wt.-%, most preferably more than 90 wt.-%, and in particular more than 95 wt.-% of polymers which are not or hardly soluble in ethanol with respect to the overall amount of polymers contained in the pharmaceutical dosage form.

Preferred polymers which are not or hardly soluble in ethanol according to the invention are xanthan, guar gum and some types of HPMC. The skilled person knows what types of HPMC are not or hardly soluble in ethanol within the sense of the invention.

In a particularly preferred embodiment, one or more particles containing pharmacologically active ingredient and physiologically acceptable polymer, more preferably the entire pharmaceutical dosage form according to the invention contains polymers which are not or hardly soluble in ethanol and polymers which are soluble in ethanol, wherein the amount of polymers which are not or hardly soluble in ethanol relative to the total amount of polymers contained in the dosage form is 30 to 100 wt.-%, more preferably 50 to 100 wt.-%, still more preferably 60 to 95 wt.-% or 100 wt.-%, yet more preferably 70 to 90 wt.-% or 100 wt.-%, most preferably 80 to 90 wt.-% or 90 to 100 wt.-%, and in particular more than 95 wt.-% or more than 99 wt.-%.

In a preferred embodiment, the tamper-resistant pharmaceutical dosage form according to the invention is a capsule and comprises a single particle comprising a pharmacologically active ingredient and a physiologically acceptable polymer; having a breaking strength of at least 300 N; having a weight of at least 2 mg; and optionally, comprising a film-coating; wherein a) said single particle has a weight within the range of 250±210 mg, more preferably 250±180 mg, still more preferably 250±150 mg, yet more preferably 250±120 mg, even more preferably 250±90 mg, most preferably 250±60 mg, and in particular 250±30 mg; or said single particle has a weight within the range of 215±210 mg, more preferably 215±180 mg, still more preferably 215±150 mg, yet more preferably 215±120 mg, even more preferably 215±90 mg, most preferably 215±60 mg, and in particular 215±30 mg; and/or b) under in vitro conditions in 600 mL 0.1 N HCl, using the basket method according to Ph. Eur. at 75 rpm, after 1 h under physiological conditions, said tamper-resistant pharmaceutical dosage form has released at most 60%, more preferably at most 55%, still more preferably at most 50%, yet more preferably at most 45%, even more preferably at most 40%, most preferably at most 35% and in particular at most 30% of the pharmacologically active ingredient relative to the total amount of the pharmacologically active ingredient originally contained in the tamper-resistant pharmaceutical dosage form; and/or c) said physiologically acceptable polymer is preferably selected from the group consisting of polyalkylene oxides, nonionic acrylates, anionic acrylates or cationic acrylates; and/or d) physiologically acceptable polymer is preferably selected from the group consisting of polyalkylene oxides, nonionic acrylates, anionic acrylates or cationic acrylates; and/or e) said pharmacologically active ingredient is an opioid, more preferably selected from the group consisting of oxycodone, oxymorphone, hydromorphone, hydrocodone, morphine, tapentadol, tramadol, buprenorphine, and the physiologically acceptable salts thereof; and/or f) said tamper-resistant pharmaceutical dosage form comprises in addition to the capsule one or more further excipient(s).

In another preferred embodiment, the tamper-resistant pharmaceutical dosage form according to the invention is a capsule and comprises n particles with n>1, preferably n particles with n=2, 3 or 4, each comprising a pharmacologically active ingredient and a physiologically acceptable polymer; having a breaking strength of at least 300 N; having a weight of at least 2 mg; and optionally, comprising a film-coating; wherein a) each of said n particles has a weight within the range of (250±210)/n mg, more preferably (250±180)/n mg, still more preferably (250±150)/n mg, yet more preferably (250±120)/n mg, even more preferably (250±90)/n mg, most preferably (250±60)/n mg, and in particular (250±35)/n mg or (250±30)/n mg; wherein n is preferably 2, 3, 4; and/or b) under in vitro conditions in 600 mL 0.1 N HCl, using the basket method according to Ph. Eur. at 75 rpm, after 1 h under physiological conditions, said tamper-resistant pharmaceutical dosage form has released at most 60%, more preferably at most 55%, still more preferably at most 50%, yet more preferably at most 45%, even more preferably at most 40%, most preferably at most 35% and in particular at most 30% of the pharmacologically active ingredient relative to the total amount of the pharmacologically active ingredient originally contained in the tamper-resistant pharmaceutical dosage form; and/or c) physiologically acceptable polymer is preferably selected from the group consisting of polyalkylene oxides, nonionic acrylates, anionic acrylates or cationic acrylates; and/or d) said pharmacologically active ingredient is an opioid, more preferably selected from the group consisting of oxycodone, oxymorphone, hydromorphone, hydrocodone, morphine, tapentadol, tramadol, buprenorphine, and the physiologically acceptable salts thereof; and/or e) said tamper-resistant pharmaceutical dosage form comprises one or more further pharmacologically active ingredients, preferably an analgesic, more preferably selected from the group consisting of paracetamol (acetaminophen) or ibuprofen; and/or f) said tamper-resistant pharmaceutical dosage form comprises in addition to the capsule one or more further excipient(s).

In a preferred embodiment, the tamper-resistant pharmaceutical dosage form according to the invention is a tablet and comprises a single particle comprising a pharmacologically active ingredient and a physiologically acceptable polymer; having a breaking strength of at least 300 N; having a weight of at least 2 mg; and optionally, comprising a film-coating; wherein a) said single particle has a weight within the range of 250±210 mg, more preferably 250±180 mg, still more preferably 250±150 mg, yet more preferably 250±120 mg, even more preferably 250±90 mg, most preferably 250±60 mg, and in particular 250±30 mg; or said single particle has a weight within the range of 215±210 mg, more preferably 215±180 mg, still more preferably 215±150 mg, yet more preferably 215±120 mg, even more preferably 215±90 mg, most preferably 215±60 mg, and in particular 215±30 mg; and/or b) under in vitro conditions in 600 mL 0.1 N HCl, using the basket method according to Ph. Eur. at 75 rpm, after 1 h under physiological conditions, said tamper-resistant pharmaceutical dosage form has released at most 60%, more preferably at most 55%, still more preferably at most 50%, yet more preferably at most 45%, even more preferably at most 40%, most preferably at most 35% and in particular at most 30% of the pharmacologically active ingredient relative to the total amount of the pharmacologically active ingredient originally contained in the tamper-resistant pharmaceutical dosage form; and/or c) physiologically acceptable polymer is preferably selected from the group consisting of polyalkylene oxides, non-ionic acrylates, anionic acrylates or cationic acrylates; and/or d) said pharmacologically active ingredient is an opioid, more preferably selected from the group consisting of oxycodone, oxymorphone, hydromorphone, hydrocodone, morphine, tapentadol, tramadol, buprenorphine, and the physiologically acceptable salts thereof; and/or e) said tamper-resistant pharmaceutical dosage form comprises one or more further pharmacologically active ingredients, preferably an analgesic, more preferably selected from the group consisting of paracetamol (acetaminophen) or ibuprofen; and/or f) said tamper-resistant pharmaceutical dosage form comprises one or more excipient(s).

In another preferred embodiment, the tamper-resistant pharmaceutical dosage form according to the invention is a tablet and comprises n particles with n>1, preferably n particles with n=2, 3 or 4, each comprising a pharmacologically active ingredient and a physiologically acceptable polymer; having a breaking strength of at least 300 N; having a weight of at least 2 mg; and optionally, comprising a film-coating; wherein a) each of said n particles has a weight within the range of (250±210)/n mg, more preferably (250±180)/n mg, still more preferably (250±150)/n mg, yet more preferably (250±120)/n mg, even more preferably (250±90)/n mg, most preferably (250±60)/n mg, and in particular (250±35)/n mg or (250±30)/n mg; wherein n is preferably 2, 3, 4; and/or b) under in vitro conditions in 600 mL 0.1 N HCl, using the basket method according to Ph. Eur. at 75 rpm, after 1 h under physiological conditions, said tamper-resistant pharmaceutical dosage form has released at most 60%, more preferably at most 55%, still more preferably at most 50%, yet more preferably at most 45%, even more preferably at most 40%, most preferably at most 35% and in particular at most 30% of the pharmacologically active ingredient relative to the total amount of the pharmacologically active ingredient originally contained in the tamper-resistant pharmaceutical dosage form; and/or c) physiologically acceptable polymer is preferably selected from the group consisting of polyalkylene oxides, non-ionic acrylates, anionic acrylates or cationic acrylates; and/or d) said pharmacologically active ingredient is an opioid, preferably selected from the group consisting of oxycodone, oxymorphone, hydromorphone, hydrocodone, morphine, tapentadol, tramadol, buprenorphine, and the physiologically acceptable salts thereof; and/or e) said tamper-resistant pharmaceutical dosage form comprises one or more further pharmacologically active ingredients preferably an analgesic, more preferably selected from the group consisting of paracetamol (acetaminophen) or ibuprofen; and/or f) said tamper-resistant pharmaceutical dosage form comprises one or more excipient(s).

In the above definitions, the features (a), (b), (c) . . . (f) are linked with "and/or". For the purpose of specification, this means that the tamper-resistant pharmaceutical dosage form according to the invention preferably realizes all of said features (a), (b), (c) . . . (f) or merely a subgroup of said features (a), (b), (c) . . . (f). Preferred tamper-resistant pharmaceutical dosage forms according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f);

In a preferred embodiment, the pharmaceutical dosage form according to the invention is adapted for administration once daily. In another preferred embodiment, the pharmaceutical dosage form according to the invention is adapted for administration once daily, preferably orally. In another preferred embodiment, the pharmaceutical dosage form according to the invention is adapted for administration twice daily, preferably orally. In still another preferred embodiment, the pharmaceutical dosage form according to the invention is adapted for administration thrice daily, preferably orally. In yet another preferred embodiment, the pharmaceutical dosage form according to the invention is adapted for administration more frequently than thrice daily, for example 4 times daily, 5 times daily, 6 times daily, 7 times daily or 8 times daily, in each case preferably orally.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

The pharmaceutical dosage forms according to the invention may be used in medicine, e.g. as an analgesic. The pharmaceutical dosage forms are therefore particularly suitable for the treatment or management of pain. In such pharmaceutical dosage forms, the pharmacologically active ingredients and preferably are analgesically effective.

A further aspect of the invention relates to the pharmaceutical dosage form as described above for use in the treatment of pain.

A further aspect of the invention relates to the use of the pharmacologically active ingredient for the manufacture of a pharmaceutical dosage form as described above for treating pain.

A further aspect of the invention relates to a method of treating pain comprising the administration of the pharmaceutical dosage form as described above to a subject in need thereof.

A further aspect according to the invention relates to the use of a pharmaceutical dosage form as described above for avoiding or hindering the abuse of the pharmacologically active ingredient contained therein.

A further aspect according to the invention relates to the use of a pharmaceutical dosage form as described above for avoiding or hindering the unintentional overdose of the pharmacologically active ingredient contained therein.

In this regard, the invention also relates to the use of a pharmaceutical dosage form as described above for the prophylaxis and/or the treatment of a disorder, thereby preventing an overdose of the pharmacologically active ingredient, particularly due to comminution of the pharmaceutical dosage form by mechanical action.

EXAMPLES

The following examples further illustrate the invention but are not to be construed as limiting its scope Cut Rods CR1 to CR3:

Cut rods of different weight but the following identical composition were manufactured:

| Component | wt.-% |
|---|---|
| Oxycodone HCL | 18.60 |
| Polyethylene oxide 7.000.000 | 56.80 |
| Hypromelose 100,000 mPas*s Ph. Eur | 10.00 |
| Macrogol 6000 Ph.Eur. | 13.56 |
| Alpha-Tocopherol Ph.Eur. | 0.20 |
| Citric acid anhydrous Ph.Eur. | 0.84 |
| Total | 100 |

The cut rods were produced using a 5 mm nozzle by weighing the ingredients, sieving (Mesh size 1.0 mm), blending in a Bohle LM 40 MC 20, followed by extrusion using a twin-screw extruder Leistritz ZSE 27 Micro PH 40 D (melt temperature 124° C., screw rotation speed 100 rpm, die diameter 5.0 mm, melt pressure ca. 80 bar) equipped with 6 cooling injectors.

The weight of cut rods CR1, CR2 and CR3 was chosen such that the total weight of one cut rod CR1 corresponded to the total weight of two cut rods CR2 and three cut rods CR3, respectively. The extruded strands were cut with a Combi Cutting unit CC 250. Cut rods (CR1-CR3) of an average weight of 267 mg (CR1), 133 mg (CR2) and 89 mg (CR3) were obtained. Minimum, maximum and mean values of length, weight, and diameter of a total of 10 cut rods were evaluated:

| | | Weight [mg] | Length [mm] | Diameter [mm] |
|---|---|---|---|---|
| CR1 | Min | 262 | 10.36 | 3.31 |
| | Max | 270 | 10.46 | 5.39 |
| | Mean | 267 | 10.41 | 5.35 |
| CR2 | Min | 125 | 4.87 | 5.32 |
| | Max | 140 | 5.37 | 5.45 |
| | Mean | 133 | 5.16 | 5.37 |
| CR3 | Min | 85 | 3.23 | 5.29 |
| | Max | 93 | 3.61 | 5.45 |
| | Mean | 89 | 3.37 | 5.36 |

Lactose Tablets LT1 and LT2:

Round-shaped tablets of a diameter of 9 mm were manufactured from the following compositions using a tablet press EK0:

| tablet | weight [mg] lactose | weight [mg] magnesium stearate |
|---|---|---|
| LT1 | 310.86 | 3.14 |
| LT2 | 410 | 0 |

Capsules A1 to A8 and Comparative Tablet A9:

The following hard gelatine capsules were employed:

| size | weight [mg] |
|---|---|
| 000 | 162 |
| 0 | 95 |
| 1 | 75 |

Capsules A1 to A8 were prepared by filling the empty capsules with 1 to 3 cut rods and optionally with lactose tablets. Additionally a comparative tablet (A9) having the same composition as the cut rods was prepared by shaping a single, hot-melt extruded cut rod into tablet shape such that the pharmaceutical dosage form (=tablet) consisted of the cut rod and due to the absence of any further excipient(s), did not have a greater total weight than the cut rod as such:

| | Capsule size | Cut rod | Number of cut rods | Number of lactose tablets | Type of lactose tablet |
|---|---|---|---|---|---|
| A1 | 0 | CR1 | 1 | 0 | — |
| A2 | 0 | CR2 | 2 | 0 | — |
| A3 | 0 | CR3 | 3 | 0 | — |
| A4 | 000 | CR1 | 1 | 0 | — |
| A5 | 000 | CR2 | 2 | 1 | LT1 |
| A6 | 000 | CR3 | 3 | 2 | LT1 |
| A7 | 0 | CR1 | 1 | 0 | — |
| A8 | 0 | CR1 | 1 | 0 | LT2 |
| A9 | 6 × 15 mm tablet | — | — | — | — |

FIG. 9 depicts the visual appearance of the comparative tablets A9: imperfect shaping is marked with "I". It becomes clear that in the course of shaping the outer silhouette of the tablet already was not perfectly formed and rounded. The outer edges of several tablets were not parallel to one another and the radius of curvature of the opposing front faces was different, not symmetric.

Dissolution Tests:

The release profiles of oxycodone HCl (average over n=3 measurements) from the capsules A1 were determined under in vitro conditions over a period of 12 hours in 0.1N HCl using the basket method, the Labswiss sinkers method and the Sotax sinkers method according to Ph. Eur. The table here below shows how the measured release profile depends on the method:

| | dissolution [%] (0.1 N HCl) | | |
|---|---|---|---|
| t [min] | (basket) | (Labswiss sinker) | (Sotax sinker) |
| 60 | 18 | 21 | 22 |
| 120 | 30 | 34 | 36 |
| 480 | 79 | 83 | 86 |
| 600 | 88 | 92 | 94 |
| 720 | 95 | 94 | 95 |

FIG. 3 illustrates the dependence of the dissolution profile on the method of measuring drug release (basket, Labswiss sinker, Sotax sinker)

The table here below shows how the release profile (basket method) depends on the number of cut rods in the capsule in 0.1N HCl:

| | dissolution [%] (0.1 N HCl) | | |
|---|---|---|---|
| filling t [min] | A1 1 CR1 | A2 2 CR2 | A3 3 CR3 |
| 60 | 20 | 21 | 22 |
| 120 | 34 | 35 | 37 |
| 480 | 83 | 87 | 88 |
| 600 | 90 | 92 | 93 |
| 720 | 94 | 96 | 96 |

FIG. 4 shows the dissolution profiles of capsules A1, A2, and A3 in 0.1N HCl.

It becomes clear from the above data that when dividing the single cut rod CR1 of capsule A1 into 2 pieces of corresponding total weight (2 cut rods CR2 of capsule A2) and 3 pieces of corresponding total weight (3 cut rods CR3 of capsule A3), respectively, this does not significantly alter the release profile. This is particularly surprising, as one would usually expect that the smaller the particle size the faster the release profile.

The table below shows how the release profile (basket method) depends on the number of cut rods and lactose tablets in the capsule:

| | dissolution [%] (0.1 N HCl) | | |
|---|---|---|---|
| filling t [min] | A4 1 CR1 | A5 2 CR2 + 1 LT1 | A6 3 CR3 + 2 LT1 |
| 60 | 22 | 27 | 34 |
| 120 | 36 | 44 | 54 |
| 480 | 83 | 84 | 97 |
| 600 | 90 | 98 | 98 |
| 720 | 95 | 100 | 99 |

FIG. 5 shows the dissolution profiles of capsules A4, A5, and A6 in 0.1N HCl.

It appears that the lactose tablet serves as a barricade to avoid sticking of the cut rods. In the presence of the lactose tablets LT1, the release profile is accelerated. This effect is directly attributable to the presence of the lactose tablets, as it becomes clear from FIG. 4 that splitting up the number of particles from 1 (capsule A1) to 2 particles of the corresponding total weight (capsule A2) and 3 particles of the corresponding total weight (capsule A3), respectively, does not significantly alter the release profile.

The table below shows how the release profile (basket method) depends on the aqueous dissolution medium:

| | Dissolution [%] | | | | | | | | |
|---|---|---|---|---|---|---|---|---|---|
| | A7 | | | A8 | | | A9 | | |
| | | | | type/filling | | | | | |
| | 1 CR1 | | | 1 CR1 + 1 LT2 | | | comparative tablet | | |
| | | | | medium | | | | | |
| | 0.1N HCl | SIFsp, pH 6.8 | 0.1N HCl + 40% ethanol | 0.1N HCl | SIFsp, pH 6.8 | 0.1N HCl + 40% ethanol | 0.1N HCl | SIFsp, pH 6.8 | 0.1N HCl + 40% ethanol |
| after 60 | 18 | 16 | 14 | 24 | 25 | 15 | 26 | 28 | 19 |
| after 120 | 30 | 30 | 25 | 37 | 41 | 26 | 40 | 43 | 29 |
| after 480 | 79 | 76 | 63 | 84 | 84 | 64 | 87 | 85 | 67 |
| after 600 | 88 | 84 | 72 | 91 | 90 | 72 | 92 | 91 | 76 |
| after 720 | 95 | 89 | 78 | 95 | 94 | 79 | 95 | 94 | 82 |

FIG. 6 shows the dissolution profiles of capsules A7 and A8 as well as of comparative tablet A9 in 0.1N HCl. FIG. 7 shows the dissolution profile of capsule A7 and A8 as well as of comparative tablet A9 in SIFsp, pH 6.8. FIG. 8 shows the dissolution profile of capsule A7 and A8 as well as of comparative tablet A9 in 0.1NHCl±40% ethanol.

Other Tests:

A core test battery for oral solids was used in accordance with the methods described in the general part of the description. Extraction from the intact dosage form was performed for 30 min in 30 ml water and in 30 ml 40% aqueous ethanol solution (obtained by mixing of boiling water and ethanol or by mixing of water at room temperature with ethanol). The results are summarized in the table here below:

| assay [%]* | A7 | A8 | A9 |
|---|---|---|---|
| type/filling | 1 CR1 | 1 CR1 + 1 LT2 | comparative tablet |
| intact dosage form | 96.5 | 96.5 | 96.7 |
| extraction water RT | 0.3 | 0.0 | 15.8 |
| extraction boiling water | 24.6 | 28.2 | 26.5 |

-continued

| assay [%]* | A7 | A8 | A9 |
|---|---|---|---|
| extraction 40% ethanol | 0.0 | 2.68** | 9.7 |
| i.v. injection | 33.2 | *** | 27.5 |

*n = 2
**n = 1
*** No analysis possible, too jelly

The capsules were subjected to different tests in order to assess the tamper-resistance with respect to the oxycodone HCl contained in the cut rods.

The hammer test was performed with a weight of 500 g falling from a height of 1000 mm.

The sieve analysis was performed after grinding 2 min with a coffee grinder.

Resistance to crushing was tested with a Zwick device.

The results are summarized in the tables here below:

Hammer Test:

|  | A7 | A8 | A9 |
|---|---|---|---|
| type/filling | 1 CR1 | 1 CR1 + 1 LT2 | comparative tablet |
| Falling weight [g] | 500 | 500 | 500 |
| Height of fall [mm] | 1000 | 1000 | 1000 |
| Category after hammer test | + | + | 0 |

Category: ++ = fully intact, + = intact, 0 = deformed, - = severely damaged, -- = destroyed.

Sieve Analysis after Grinding:

| | A7* 1 CR1 | | | A9* comparative tablet | | |
|---|---|---|---|---|---|---|
| Mesh size [mm] | Fraction [%] | Fraction [%] | Fraction [%] | Fraction [%] | Fraction [%] | Fraction [%] |
| <0.063 | −0.305 | −0.3 | −0.3 | −0.5 | −0.4 | −0.5 |
| 0.063-0.090 | −0.3 | −0.3 | −0.3 | −0.5 | −0.4 | −0.5 |
| 0.090-0.125 | 0.3 | 0.3 | 0.3 | 0.5 | 0.4 | 0.5 |
| 0.125-0.180 | 0.6 | 0.6 | −2.4 | 0.9 | 0.8 | 0.9 |
| 0.180-0.250 | −1.2 | 1.8 | 1.8 | −1.8 | 2.4 | −1.8 |
| 0.250-0.355 | 1.2 | 1.2 | 1.2 | 1.8 | 1.6 | 1.8 |
| 0.355-0.500 | 4.3 | 4.1 | 4.1 | 1.8 | 1.6 | 1.8 |
| 0.500-0.710 | 9.1 | 8.9 | 8.9 | 9.2 | 8.1 | 4.6 |
| 0.710-1.000 | 12.5 | 12.1 | 15.1 | 14.2 | 16.5 | 14.2 |
| 1.000-1.400 | 25.9 | 22.2 | 31.1 | 34.4 | 34.3 | 25.2 |
| 1.400-2.000 | 32.3 | 34.3 | 28.4 | 44.0 | 30.6 | 30.3 |
| 2.000-2.800 | 14.6 | 11.2 | 11.2 | 12.8 | 7.3 | 17.4 |
| 2.800-4.000 | 0.9 | 3.8 | 0.9 | −17.0 | −2.8 | 6.0 |
| >4.000 | 0.0 | 0.0 | 0.0 | 0.0 | 0.0 | 0.0 |

*The negative fraction sizes are for analytical reasons. The weight of the sieves is measured before and after sieving, and sieving results may deviate.

Less than 5% of the dosage forms could be ground to particles sizes of 355 mm or less, indicating a good resistance against the preparation of a nasal abusable powder. Sieve analysis was not performed for capsules A8 as it was considered useless, because a very high amount of fines is already incorporated by the lactose surrounding the cut rod in the capsule. Thereby the amount of fines is not representative for the tamper resistance of the drug product.

Resistance to Crushing with a Zwick

None of the capsules showed any sign of fracture, however, the measured $F_{max}$ is the highest measured force just below the measuring limit of 1500N.

Cut Rods CR 4:

Cut rods having a total weight of 215 mg were produced according to the procedure disclosed above and having the composition as summarized in the table below:

| | m per capsule [mg] | wt.-% |
|---|---|---|
| Oxycodone HCl | 5.00 | 2.33 |
| Polyethylene oxide 7.000.000 | 150.51 | 70.00 |
| Hypromellose 100000 mPa * s Ph.Eur | 21.50 | 10.00 |
| Macrogol 6000 Ph.Eur. | 35.75 | 16.63 |
| α-Tocopherol Ph.Eur. | 0.43 | 0.20 |
| Critic acid anhydrous Ph.Eur. | 1.81 | 0.84 |
| Total | 215.00 | 100.00 |

The breaking strength (resistance to crushing) was measured using a Sotax HT 100 (DEAC- IN-00705). The cut rods displayed a breaking strength of 1000 N (mean value; n = 3, with measured values $b_1 = b_2 = b_3 = 1000$ N).

FIG. 10 shows the release profiles of one cut rod determined under in vitro conditions (n=3) using the basket method with sinker according to Ph. Eur. at 75 rpm in 600 mL of SGF (pH 1.2) and SGF (pH 1.2)+40% ethanol, respectively.

Cut Rods CR 5:

Cut rods having a total weight of 107.5 mg were produced according to the procedure disclosed above and having the composition as summarized in the table below:

| | m per capsule [mg] | wt.-% |
|---|---|---|
| Oxycodone HCl | 2.50 | 2.33 |
| Polyethylene oxide 7.000.000 | 75.255 | 70.00 |
| Hypromellose 100000 mPa *s Ph.Eur | 10.75 | 10.00 |
| Macrogol 6000 Ph.Eur. | 17.875 | 16.63 |
| α-Tocopherol Ph.Eur. | 0.215 | 0.20 |
| Critic acid anhydrous Ph.Eur. | 0.905 | 0.84 |
| Total | 107.50 | 100.00 |

FIG. 11 shows the release profiles of two cut rods determined under in vitro conditions (n=3) using the basket method with sinker according to Ph. Eur. (one sinker per cut rod) at 75 rpm in 600 mL of SGF (pH 1.2) and SGF (pH 1.2)+40% ethanol, respectively.

Capsule A 10:

Capsules comprising one cut rod were produced according to the procedure disclosed above. One cut rod (215 mg) was filled in a capsule (size 1). The composition of the capsule is summarized in the table below:

| | m per capsule [mg] | wt.-% |
|---|---|---|
| Oxycodone HCl | 5.00 | 1.72 |
| Polyethylene oxide 7.000.000 | 150.51 | 51.90 |

| | A7 | | | A8 | | | A9 | | |
|---|---|---|---|---|---|---|---|---|---|
| type/filling | 1 CR1 | | | 1 CR1 + 1 LT2 | | | comparative tablet | | |
| $F_{max}$ [N] | 1502.2 | 1498.1 | 1494.1 | 1495.4 | 1494.2 | 1497.0 | 1492.9 | 1494.5 | 1493.7 |
| $S_{max}$ [mm] | 16.8 | 16.6 | 16.7 | 16.9 | 16.8 | 16.60 | 10.2 | 10.1 | 10.0 |

|  | m per capsule [mg] | wt.- % |
|---|---|---|
| Hypromellose 100000 mPa * s Ph.Eur | 21.50 | 7.41 |
| Macrogol 6000 Ph.Eur. | 35.75 | 12.33 |
| α-Tocopherol Ph.Eur. | 0.43 | 0.15 |
| Critic acid anhydrous Ph.Eur. | 1.81 | 0.62 |
| empy capsule size 1 | 75.00 | 25.86 |
| Total | 290.00 | 100.00 |

The breaking strength (resistance to crushing) was measured using a Sotax HT 100 (DEAC- IN-00705). The capsules displayed a breaking strength of 63 N (mean value; n = 3*; with measured values $b_1$ = 50 N; $b_2$ = 76 N; $b_3$ = 1000 N*).
*The measured value $b_3$ was not included in the mean value of the breaking strength because it was obtained from an incorrect measurement (the capsule was crushed and the breaking strength of the cut rod was measured instead).

FIG. 12 shows the release profiles of one cut rod in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Capsule A 11:

Capsules comprising two cut rods and a lactose tablet were produced according to the procedure disclosed above. Two cut rods (107.5 mg each) and a lactose tablet (72 mg) as spacer were filled in a capsule (size 1). The composition of the capsule is summarized in the table below:

|  | m per capsule [mg] | wt.- % |
|---|---|---|
| Oxycodone HCl | 5.00 | 1.38 |
| Polyethylene oxide 7.000.000 | 150.51 | 41.58 |
| Hypromellose 100000 mPa * s Ph.Eur | 21.50 | 5.94 |
| Macrogol 6000 Ph.Eur. | 35.75 | 9.88 |
| α-Tocopherol Ph.Eur. | 0.43 | 0.12 |
| Critic acid anhydrous Ph.Eur. | 1.81 | 0.50 |
| empy capsule size 1 | 75.00 | 20.72 |
| Lactose tablet | 72.00 | 19.89 |
| Total | 362.00 | 100.00 |

The breaking strength (resistance to crushing) was measured using a Sotax HT 100 (DEAC- IN-00705). The capsules displayed a breaking strength of 38 N (mean value; n = 3*; with measured values $b_1$ = 1000 N*; $b_2$ = 31 N; $b_3$ = 45 N).
*The measured value $b_1$ was not included in the mean value of the breaking strength because it was obtained from an incorrect measurement (the capsule was crushed and the breaking strength of the cut rod was measured instead).

FIG. 13 shows the release profiles of two cut rods and a lactose tablet in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Mantle Tablet M 1:

Layer-core-tablets (mantle-core-tablets) (9×21 mm, oblong) were produced using one cut rod (215 mg) as the core and an MCC-based mixture as the mantle. The MCC-based mixture was a mixture of microcrystalline cellulose (MCC) with 2 wt.-% maize starch as disintegrant and 1 wt.-% magnesium stearate. The composition of the mantle-core-tablets is summarized in the table below:

|  | m per capsule [mg] | wt.- % |
|---|---|---|
| Oxycodone HCl | 5.00 | 0.61 |
| Polyethylene oxide 7.000.000 | 150.51 | 18.47 |
| Hypromellose 100000 mPa * s Ph.Eur | 21.50 | 2.64 |
| Macrogol 6000 Ph.Eur. | 35.75 | 4.39 |
| α-Tocopherol Ph.Eur. | 0.43 | 0.05 |
| Critic acid anhydrous Ph.Eur. | 1.81 | 0.22 |
| MCC | 582.00 | 71.41 |
| Maize starch | 12.00 | 1.47 |
| Magnesium stearate | 6.00 | 0.74 |
| Total | 815.00 | 100.00 |

The breaking strength (resistance to crushing) was measured using a Sotax HT 100 (DEAC- IN-00705). The mantle tablets displayed a breaking strength of 65 N (mean value; n = 3; with measured values $b_1$ = 63 N; $b_2$ = 58 N; $b_3$ = 73 N).

FIG. 14 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

Mantle Tablet M2:

Layer-core-tablets (mantle-core-tablets) (9×21 mm, oblong) were produced using two cut rods and a lactose tablet (72 mg) as cores and an MCC-based mixture as the mantle. The MCC-based mixture was a mixture of microcrystalline cellulose (MCC) with 2 wt.-% maize starch as disintegrant and 1 wt.-% magnesium stearate. The composition of the mantle-core-tablets is summarized in the table below:

|  | m per capsule [mg] | wt.- % |
|---|---|---|
| Oxycodone HCl | 5.00 | 0.64 |
| Polyethylene oxide 7.000.000 | 150.51 | 19.12 |
| Hypromellose 100000 mPa * s Ph.Eur | 21.50 | 2.73 |
| Macrogol 6000 Ph.Eur. | 35.75 | 4.54 |
| α-Tocopherol Ph.Eur. | 0.43 | 0.05 |
| Critic acid anhydrous Ph.Eur. | 1.81 | 0.23 |
| Lactose tablet | 72.00 | 9.15 |
| MCC | 485.00 | 61.63 |
| Maize starch | 10.00 | 1.27 |
| Magnesium stearate | 5.00 | 0.64 |
| Total | 787.00 | 100.00 |

The breaking strength (resistance to crushing) was measured using a Sotax HT 100 (DEAC-IN-00705). The mantle tablets displayed a breaking strength of 19 N (mean value; n = 3; with measured values $b_1$ = 18 N; $b_2$ = 21 N; $b_3$ = 17 N).

FIG. 15 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

FIGS. 16 to 20

FIGS. 16 to 20 show combinations of the release profiles obtained from CR4, CR5, A10, A11, M1 and M2.

Figure 16:
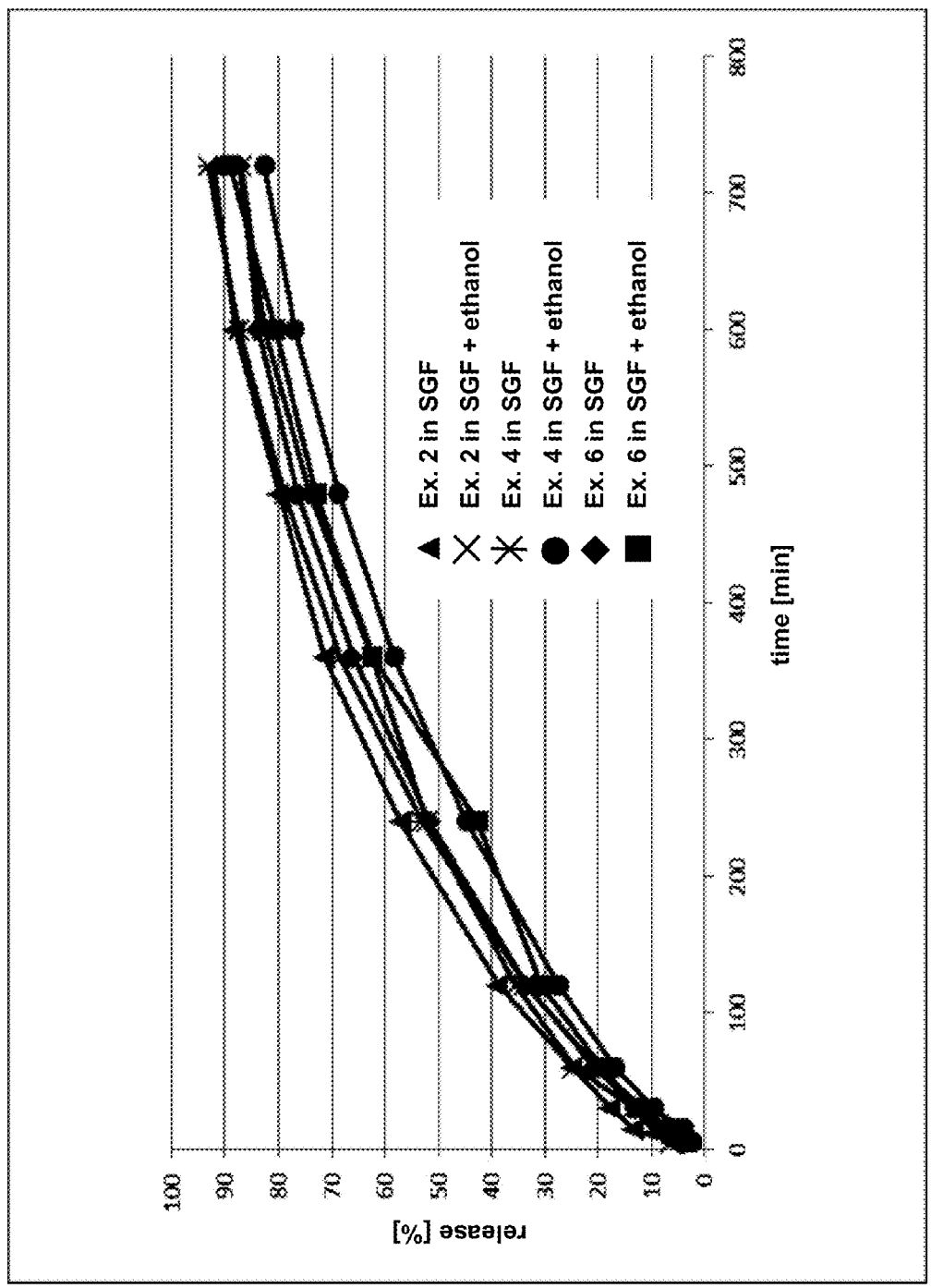

FIG. 16 shows the release profiles of the cut rod (m=215 mg) as such (CR4, FIG. 10), in a capsule (A10, FIG. 12), and in form of a mantle tablet (M1, FIG. 14).

Figure 17:
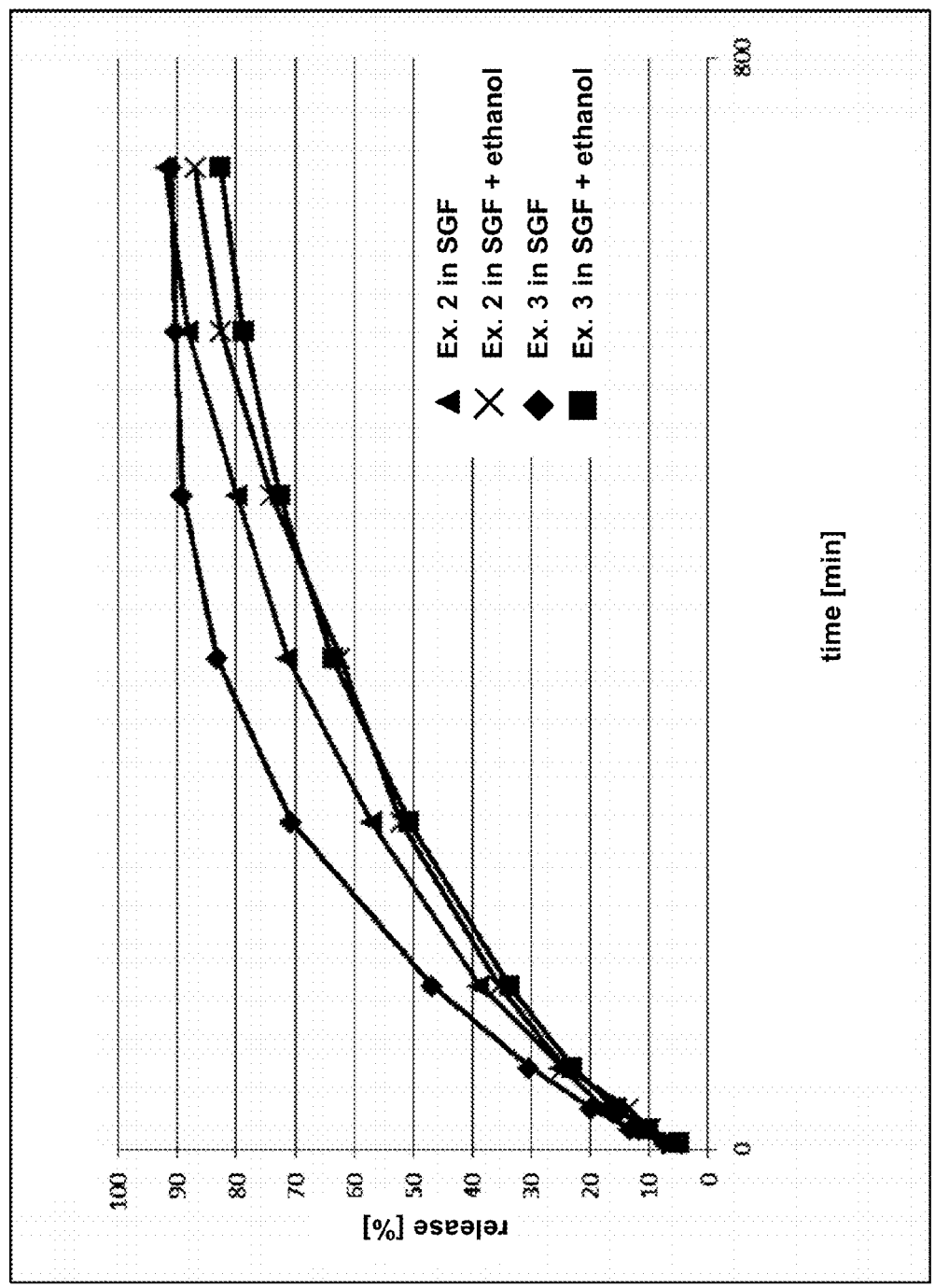

FIG. 17 shows the release profiles of one cut rod (m=215 mg) (CR4, FIG. 10) and two cut rods (m=107.5 mg) (CR5, FIG. 11).

Figure 18:
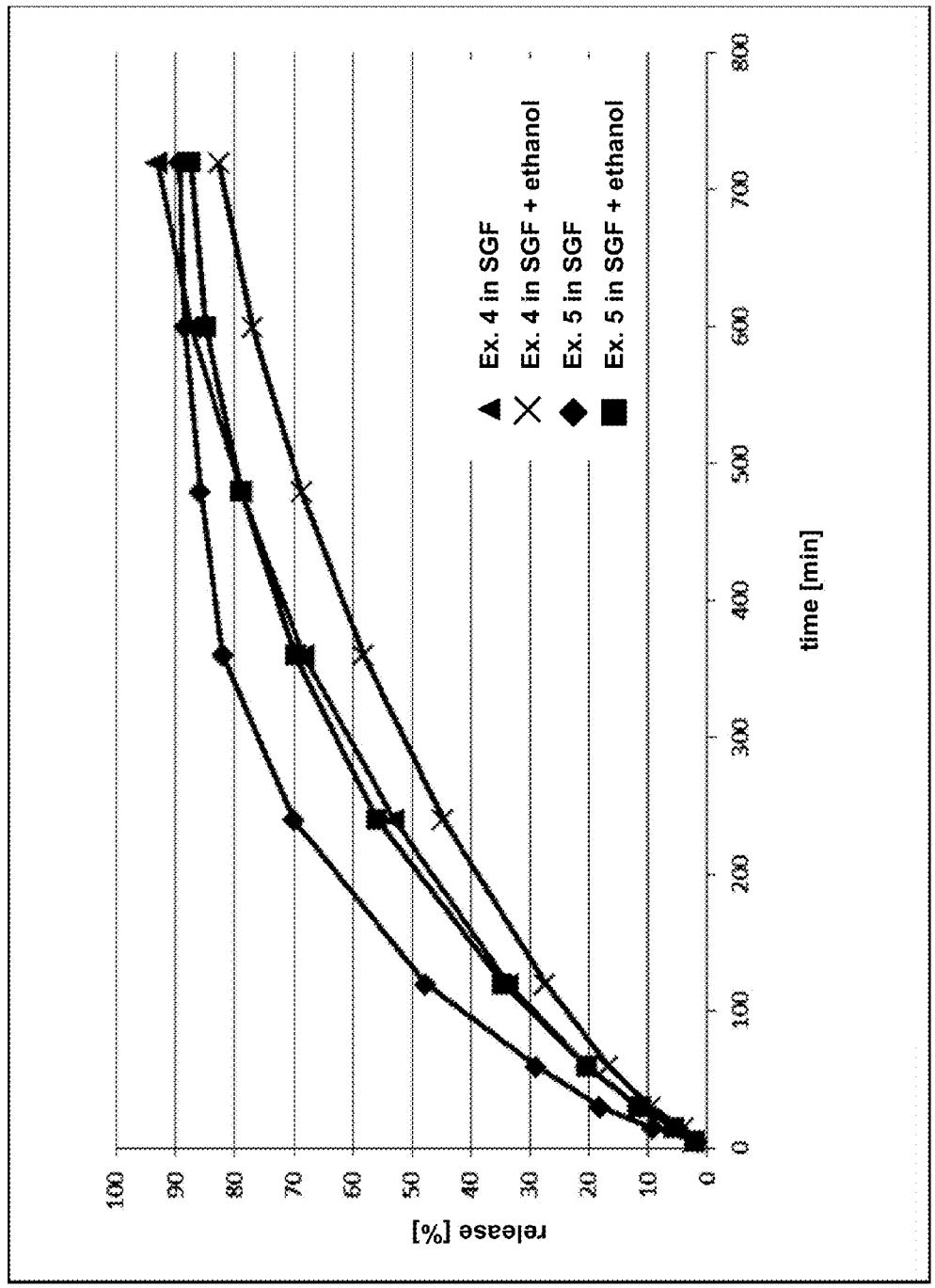

FIG. 18 shows the release profile of a capsule containing one cut rod (A10, FIG. 12) and a capsule containing two cut rods (A11, FIG. 13).

Figure 19:
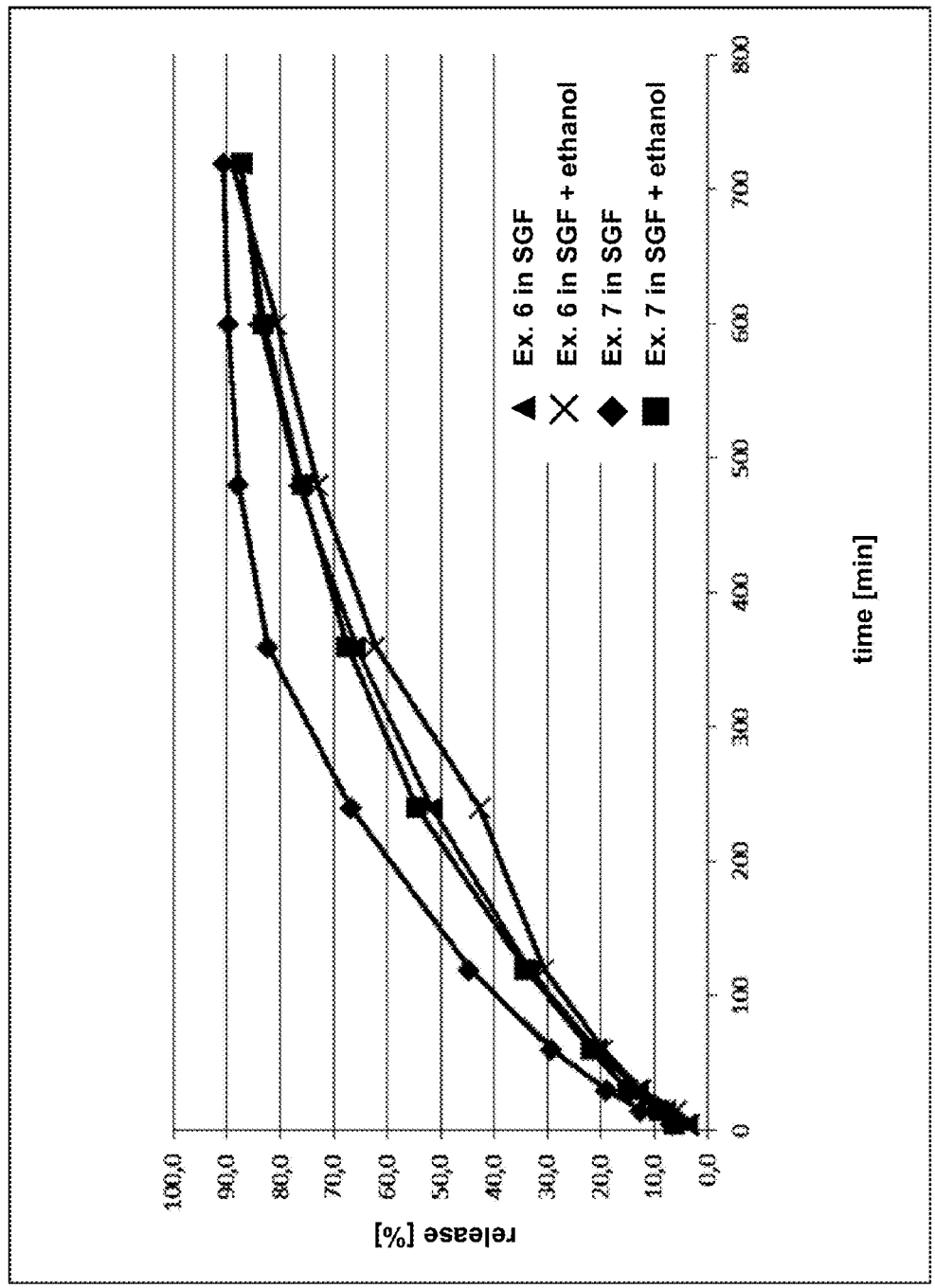

FIG. 19 shows the release profiles of a mantle tablet containing one cut rod (M1, FIG. 14) and a mantle tablet containing two cut rods (M2, FIG. 15).

Figure 20:
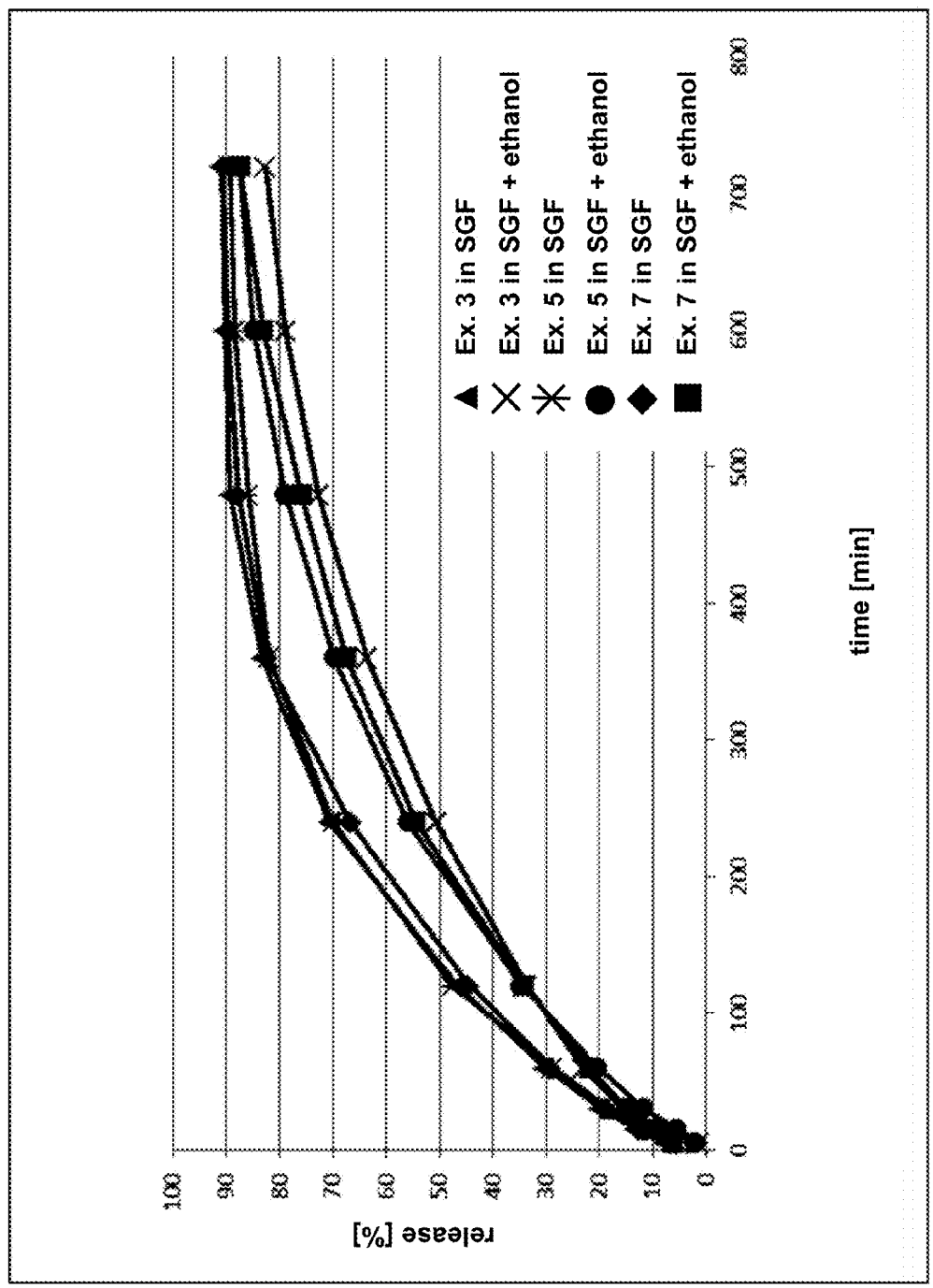

FIG. 20 shows the release profiles of two cut rods (m=107.5 mg) as such (CR5, FIG. 11), in a capsule (A11, FIG. 13), and in form of a mantle tablet (M2, FIG. 15).

The invention claimed is:

1. A tamper-resistant pharmaceutical dosage form for oral administration, said pharmaceutical dosage form being a capsule comprising:
   (a) one or more prolonged release particles, wherein each of said one or more particles:
      (i) comprises a pharmacologically active ingredient selected from the group consisting of stimulants;
      (ii) comprises a physiologically acceptable polymer selected from the group consisting of acrylic polymers and polyalkylene oxides, wherein the physiologically acceptable polymer has a weight average molecular weight of at least 200,000 g/mol, wherein the physiologically acceptable polymer is present in a content of at least 30 wt.-% relative to a total weight of the one or more particles, and wherein the pharmacologically active ingredient is embedded in a matrix comprising the physiologically acceptable polymer;
      (iii) has a breaking strength of at least 300 N;
      (iv) has a weight of at least 100 mg; and
      (v) optionally comprises a film-coating; and
   (b) one or more additional particles having a weight of less than 2 mg;
   wherein the pharmaceutical dosage form has a total weight greater than a combined weight of the particles (a) and (b);
   wherein the pharmaceutical dosage form contains no aversive agent and contains no antagonist; and
   wherein the pharmaceutical composition can be chewed without significantly deteriorating tamper-resistance and without significantly altering drug release.

2. The pharmaceutical dosage form according to claim 1, wherein the total volume of the pharmaceutical dosage form is greater than the total volume of the one or more particles.

3. The pharmaceutical dosage form according to claim 1, wherein the breaking strength of the pharmaceutical dosage form is below the breaking strength of the one or more particles.

4. The pharmaceutical dosage form according to claim 1, wherein the content of the pharmacologically active ingredient is at least 1.0 wt.-%, based on the total weight of one of the one or more particles.

5. The pharmaceutical dosage form according to claim 1, which has released at most 50% of the pharmacologically active ingredient after 60 min measured under in vitro conditions and in accordance with Ph. Eur.

6. The pharmaceutical dosage form according to claim 1, wherein the pharmacologically active ingredient is embedded in a matrix material comprising the physiologically acceptable polymer.

7. The pharmaceutical dosage form according to claim 1, wherein the total amount of the pharmacologically active ingredient that is contained in the pharmaceutical dosage form is contained in the one or more particles.

8. The pharmaceutical dosage form according to claim 1, wherein the physiologically acceptable polymer is selected from the group consisting of polyalkylene oxides, non-ionic acrylates, anionic acrylates and cationic acrylates.

9. The pharmaceutical dosage form according to claim 1, wherein the content of the physiologically acceptable polymer is at least 25 wt.-%, based on the total weight of one of the one or more particles.

10. The pharmaceutical dosage form according to claim 1, which contains at least two particles that are identical or differ from one another.

11. The pharmaceutical dosage form according to claim 1, wherein the one or more particles are of cylindrical shape.

12. The pharmaceutical dosage form according to claim 1, wherein the one or more particles are melt-extruded.

13. The pharmaceutical dosage form according to claim 1, wherein each of said one or more particles has a weight of at least 260 mg.

14. The pharmaceutical dosage form according to claim 1, wherein each of said one or more particles has a weight of at least 300 mg.

15. The pharmaceutical dosage form according to claim 1, which under in vitro conditions in 600 mL 0.1 N HCl, using the basket method according to Ph. Eur. at 75 rpm, after 1 h, has released at most 60% of the pharmacologically active ingredient relative to the total amount of the pharmacologically active ingredients originally contained in the pharmaceutical dosage form.

16. The pharmaceutical dosage form according to claim 1, wherein the pharmaceutically acceptable active ingredient is selected from the group consisting of amphetamine, amphetaminil, lisdeamfetamine dimesylate, and metamphetamine, and the physiologically acceptable salts thereof, and combinations thereof.

17. The pharmaceutical dosage form according to claim 16, wherein the pharmaceutically acceptable active ingredient is selected from the group consisting of amphetamine and the physiologically acceptable salts thereof.

18. The pharmaceutical dosage form according to claim 1, wherein the pharmaceutically acceptable active ingredient is selected from the group consisting of methylphenidate and the physiologically acceptable salts thereof.

19. A tamper-resistant pharmaceutical dosage form for oral administration, said pharmaceutical dosage form being a capsule comprising:
   (a) one or more prolonged release particles, wherein each of said one or more particles:
      (i) comprises a first pharmacologically active ingredient selected from the group consisting of stimulants;
      (ii) comprises a physiologically acceptable polymer selected from the group consisting of acrylic polymers and polyalkylene oxides, wherein the physiologically acceptable polymer has a weight average molecular weight of at least 200,000 g/mol, wherein the physiologically acceptable polymer is present in a content of at least 30 wt-% relative to a total weight of the one or more particles, and wherein the pharmacologically active ingredient is embedded in a matrix comprising the physiologically acceptable polymer;
      (iii) has a breaking strength of at least 300 N;
      (iv) has a weight of at least 100 mg; and
      (v) optionally comprises a film-coating; and
   (b) one or more additional particles having a weight of less than 2 mg;
   wherein the pharmaceutical dosage form has a total weight greater than a combined weight of the particles (a) and (b); and
   wherein the pharmaceutical dosage form does not contain a second pharmacologically active ingredient; and
   wherein the pharmaceutical composition can be chewed without significantly deteriorating tamper-resistance and without significantly altering drug release.

20. The pharmaceutical dosage form according to claim 18, which under in vitro conditions in 600 mL 0.1 N HCl, using the basket method according to Ph. Eur. at 75 rpm, after 1 h, has released at most 60% of the pharmacologically active ingredient relative to the total amount of the pharmacologically active ingredients originally contained in the pharmaceutical dosage form.

21. A tamper-resistant pharmaceutical dosage form for oral administration, said pharmaceutical dosage form being a capsule comprising:
(a) one or more particles, wherein each of said one or more particles:
 (i) comprises a prolonged release pharmacologically active ingredient selected from the group consisting of stimulants;
 (ii) comprises a physiologically acceptable polymer selected from the group consisting of acrylic polymers and polyalkylene oxides, wherein the physiologically acceptable polymer has a weight average molecular weight of at least 200,000 g/mol, wherein the physiologically acceptable polymer is present in a content of at least 30 wt.-% relative to a total weight of the one or more particles, and wherein the pharmacologically active ingredient is embedded in a matrix comprising the physiologically acceptable polymer;
 (iii) has a breaking strength of at least 300 N;
 (iv) has a weight of at least 20 mg; and
 (v) optionally comprises a film-coating; and
(b) one or more additional particles having a weight of less than 2 mg;
wherein the pharmaceutical dosage form has a total weight greater than a combined weight of the particles (a) and (b);
wherein the one or more particles number "n," where n=1, 2, 3 or 4, and each of said n particles has a weight within the range of $(250\pm150)/n$ mg;
wherein the pharmaceutical dosage form contains no aversive agent and contains no antagonist; and
wherein the pharmaceutical composition can be chewed without significantly deteriorating tamper-resistance and without significantly altering drug release.

22. The pharmaceutical dosage form according to claim 21, which under in vitro conditions in 600 mL 0.1 N HCl, using the basket method according to Ph. Eur. at 75 rpm, after 1 h, has released at most 60% of the pharmacologically active ingredient relative to the total amount of the pharmacologically active ingredients originally contained in the pharmaceutical dosage form.

* * * * *